US012721715B2

(12) United States Patent
Grabinsky et al.

(10) Patent No.: US 12,721,715 B2
(45) Date of Patent: Sep. 1, 2026

(54) MEDICAL IMPLANT DELIVERY SYSTEM AND RELATED METHODS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Jessica Marie Grabinsky, Melrose, MA (US); Jeffrey Louis Barnes, Medford, MA (US); Nathaniel Zenz-Olson, Ham Lake, MN (US); Nathaniel Van Tran, Lakeville, MN (US); Jamal James Akid, Pawtucket, RI (US)

(73) Assignees: Smith & Nephew, Inc.; Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 628 days.

(21) Appl. No.: 18/141,724

(22) Filed: May 1, 2023

(65) Prior Publication Data

US 2023/0263615 A1 Aug. 24, 2023

Related U.S. Application Data

(63) Continuation of application No. PCT/US2021/063083, filed on Dec. 13, 2021.

(Continued)

(51) Int. Cl.

| | |
|---|---|
| ***A61F 2/02*** | (2006.01) |
| ***A61B 17/12*** | (2006.01) |
| ***A61F 2/00*** | (2006.01) |

(52) U.S. Cl.

CPC ........ *A61F 2/02* (2013.01); *A61B 2017/1205* (2013.01); *A61F 2002/0072* (2013.01)

(58) Field of Classification Search

CPC ................ A61F 2/02; A61F 2002/0072; A61F 2220/0075; A61F 2/0805; A61F 2/0811;

(Continued)

(56) References Cited

U.S. PATENT DOCUMENTS

| | | | |
|---|---|---|---|
| 511,238 | A | 12/1893 | Hieatzman et al. |
| 765,793 | A | 7/1904 | Ruckel |

(Continued)

FOREIGN PATENT DOCUMENTS

| | | | |
|---|---|---|---|
| CA | 2390508 | A1 | 5/2001 |
| CA | 2404647 | A1 | 8/2002 |

(Continued)

OTHER PUBLICATIONS

"Rotator Cuff Tear," Wikipedia, the free encyclopedia, 14 pages, Downloaded on Dec. 6, 2012.

(Continued)

*Primary Examiner* — Yashita Sharma
(74) *Attorney, Agent, or Firm* — Seager, Tufte & Wickhem LLP

(57) ABSTRACT

An implant delivery system is disclosed. The implant delivery system includes a delivery shaft and a detachable frame longitudinally advanceable relative to a delivery sheath. A tether is secured to the detachable frame and extends through a lumen of the delivery shaft to a handle. The tether may be secured to a connection assembly, including a tack member, a tack disk and a collar. The connection assembly may be attached to the detachable frame. The handle may include a tether clamp to secure the tether relative to the handle.

7 Claims, 33 Drawing Sheets

Related U.S. Application Data

(60) Provisional application No. 63/126,458, filed on Dec. 16, 2020.

(58) Field of Classification Search
CPC ...... A61F 2002/0068; A61F 2002/0817; A61F 2002/0858; A61F 2002/0882; A61F 2220/0016; A61F 2230/0006; A61F 2230/0008; A61B 2017/1205; A61B 17/068; A61B 2017/0647; A61B 17/064; A61B 17/0642; A61B 17/10; A61B 2017/00964
See application file for complete search history.

(56) References Cited

U.S. PATENT DOCUMENTS 1,728,316 A 9/1929 Von Wachenfeldt
1,855,546 A 4/1932 File
1,868,100 A 7/1932 Goodstein
1,910,688 A 5/1933 Goodstein
1,940,351 A 12/1933 Howard
2,034,785 A 3/1936 Wappler
2,075,508 A 3/1937 Davidson
2,131,321 A 9/1938 Hart
2,154,688 A 4/1939 Matthews et al.
2,158,242 A 5/1939 Maynard
2,199,025 A 4/1940 Conn
2,201,610 A 5/1940 Dawson, Jr.
2,254,620 A 9/1941 Miller
2,277,931 A 3/1942 Moe
2,283,814 A 5/1942 La Place
2,316,297 A 4/1943 Southerland et al.
2,421,193 A 5/1947 Gardner
2,571,813 A 10/1951 Austin
2,630,316 A 3/1953 Foster
2,684,070 A 7/1954 Kelsey
2,744,251 A 5/1956 Vollmer
2,790,341 A 4/1957 Keep et al.
2,817,339 A 12/1957 Sullivan
2,825,162 A 3/1958 Flood
2,881,762 A 4/1959 Lowrie
2,910,067 A 10/1959 White
3,068,870 A 12/1962 Levin
3,077,812 A 2/1963 Dietrich
3,103,666 A 9/1963 Bone
3,123,077 A 3/1964 Alcamo
3,209,754 A 10/1965 Brown
3,221,746 A 12/1965 Noble
3,470,834 A 10/1969 Bone
3,527,223 A 9/1970 Shein
3,570,497 A 3/1971 Lemole
3,577,837 A 5/1971 Bader, Jr.
3,579,831 A 5/1971 Stevens et al.
3,643,851 A 2/1972 Green et al.
3,687,138 A 8/1972 Jarvik
3,716,058 A 2/1973 Tanner, Jr.
3,717,294 A 2/1973 Green
3,757,629 A 9/1973 Schneider
3,777,538 A 12/1973 Weatherly et al.
3,837,555 A 9/1974 Green
3,845,772 A 11/1974 Smith
3,875,648 A 4/1975 Bone
3,960,147 A 6/1976 Murray
3,976,079 A 8/1976 Samuels et al.
4,014,492 A 3/1977 Rothfuss
4,127,227 A 11/1978 Green
4,259,959 A 4/1981 Walker
4,263,903 A 4/1981 Griggs
4,265,226 A 5/1981 Cassimally
4,317,451 A 3/1982 Cerwin et al.
4,400,833 A 8/1983 Kurland
4,422,567 A 12/1983 Haynes
4,454,875 A 6/1984 Pratt et al.
4,480,641 A 11/1984 Failla et al.
4,485,816 A 12/1984 Krumme
4,526,174 A 7/1985 Froehlich
4,549,545 A 10/1985 Levy
4,570,623 A 2/1986 Ellison et al.
4,595,007 A 6/1986 Mericle
4,624,254 A 11/1986 McGarry et al.
4,627,437 A 12/1986 Bedi et al.
4,632,100 A 12/1986 Somers et al.
4,635,637 A 1/1987 Schreiber
4,669,473 A 6/1987 Richards et al.
4,696,300 A 9/1987 Anderson
4,719,917 A 1/1988 Barrows et al.
4,738,255 A 4/1988 Goble et al.
4,741,330 A 5/1988 Hayhurst
4,762,260 A 8/1988 Richards et al.
4,799,495 A 1/1989 Hawkins et al.
4,809,695 A 3/1989 Gwathmey et al.
4,851,005 A 7/1989 Hunt et al.
4,858,608 A 8/1989 McQuilkin
4,884,572 A 12/1989 Bays et al.
4,887,601 A 12/1989 Richards
4,924,866 A 5/1990 Yoon
4,930,674 A 6/1990 Barak
4,968,315 A 11/1990 Gatturna
4,976,715 A 12/1990 Bays et al.
4,994,073 A 2/1991 Green
4,997,436 A 3/1991 Oberlander
5,002,563 A 3/1991 Pyka et al.
5,013,316 A 5/1991 Goble et al.
5,015,249 A 5/1991 Nakao et al.
5,037,422 A 8/1991 Hayhurst et al.
5,041,129 A 8/1991 Hayhurst et al.
5,046,513 A 9/1991 Gatturna et al.
5,053,047 A 10/1991 Yoon
5,059,206 A 10/1991 Winters
5,062,563 A 11/1991 Green et al.
5,100,417 A 3/1992 Cerier et al.
5,102,421 A 4/1992 Anspach, Jr.
5,116,357 A 5/1992 Eberbach
5,122,155 A 6/1992 Eberbach
5,123,913 A 6/1992 Wilk et al.
RE34,021 E 8/1992 Mueller et al.
5,141,515 A 8/1992 Eberbach
5,141,520 A 8/1992 Goble et al.
5,156,609 A 10/1992 Nakao et al.
5,156,616 A 10/1992 Meadows et al.
5,167,665 A 12/1992 McKinney
5,171,259 A 12/1992 Inoue
5,174,295 A 12/1992 Christian et al.
5,174,487 A 12/1992 Rothfuss et al.
5,176,682 A 1/1993 Chow
5,176,692 A 1/1993 Wilk et al.
5,203,787 A 4/1993 Noblitt et al.
5,217,472 A 6/1993 Green et al.
5,224,946 A 7/1993 Hayhurst et al.
5,238,004 A 8/1993 Sahatjian et al.
5,242,457 A 9/1993 Akopov et al.
5,246,441 A 9/1993 Ross et al.
5,251,642 A 10/1993 Handlos
5,261,914 A 11/1993 Warren
5,269,753 A 12/1993 Wilk
5,269,783 A 12/1993 Sander
5,282,829 A 2/1994 Hermes
5,289,963 A 3/1994 McGarry et al.
5,290,217 A 3/1994 Campos
5,304,187 A 4/1994 Green et al.
5,333,624 A 8/1994 Tovey
5,342,396 A 8/1994 Cook
5,350,400 A 9/1994 Esposito et al.
5,352,229 A 10/1994 Goble et al.
5,354,292 A 10/1994 Braeuer et al.
5,364,408 A 11/1994 Gordon
5,366,460 A 11/1994 Eberbach
5,370,650 A 12/1994 Tovey et al.
5,372,604 A 12/1994 Trott
5,380,334 A 1/1995 Torrie et al.
5,383,477 A 1/1995 DeMatteis
5,397,332 A 3/1995 Kammerer et al.
5,403,326 A 4/1995 Harrison et al.
5,405,360 A 4/1995 Tovey

(56) References Cited

U.S. PATENT DOCUMENTS 5,411,522 A 5/1995 Trott
5,411,523 A 5/1995 Goble
5,417,691 A 5/1995 Hayhurst
5,417,712 A 5/1995 Whittaker et al.
5,425,490 A 6/1995 Goble et al.
5,441,502 A 8/1995 Bartlett
5,441,508 A 8/1995 Gazielly et al.
5,453,090 A 9/1995 Martinez et al.
5,456,720 A 10/1995 Schultz et al.
5,464,403 A 11/1995 Kieturakis et al.
5,478,354 A 12/1995 Tovey et al.
5,482,864 A 1/1996 Knobel
5,486,197 A 1/1996 Le et al.
5,497,933 A 3/1996 DeFonzo et al.
5,500,000 A 3/1996 Feagin et al.
5,501,695 A 3/1996 Anspach, Jr. et al.
5,503,623 A 4/1996 Tilton, Jr.
5,505,735 A 4/1996 Li
5,507,754 A 4/1996 Green et al.
5,520,700 A 5/1996 Beyar et al.
5,522,817 A 6/1996 Sander et al.
5,545,180 A 8/1996 Le et al.
5,560,532 A 10/1996 DeFonzo et al.
5,562,689 A 10/1996 Green et al.
5,569,306 A 10/1996 Thal
5,582,616 A 12/1996 Bolduc et al.
5,584,835 A 12/1996 Greenfield
5,618,314 A 4/1997 Harwin et al.
5,622,257 A 4/1997 Deschenes et al.
5,628,751 A 5/1997 Sander et al.
5,643,319 A 7/1997 Green et al.
5,643,321 A 7/1997 McDevitt
5,647,874 A 7/1997 Hayhurst
5,649,963 A 7/1997 McDevitt
5,662,683 A 9/1997 Kay
5,667,513 A 9/1997 Torrie et al.
5,674,245 A 10/1997 Ilgen
5,681,342 A 10/1997 Benchetrit
5,702,215 A 12/1997 Li
5,713,903 A 2/1998 Sander et al.
5,720,753 A 2/1998 Sander et al.
5,725,541 A 3/1998 Anspach, III et al.
5,741,282 A 4/1998 Anspach, III et al.
5,766,246 A 6/1998 Mulhauser et al.
5,782,864 A 7/1998 Lizardi
5,797,909 A 8/1998 Michelson
5,797,931 A 8/1998 Bito et al.
5,797,963 A 8/1998 McDevitt
5,807,403 A 9/1998 Beyar et al.
5,830,221 A 11/1998 Stein et al.
5,836,961 A 11/1998 Kieturakis et al.
5,868,762 A 2/1999 Cragg et al.
5,873,891 A 2/1999 Sohn
5,885,258 A 3/1999 Sachdeva et al.
5,885,294 A 3/1999 Pedlick et al.
5,893,856 A 4/1999 Jacob et al.
5,904,696 A 5/1999 Rosenman
5,919,184 A 7/1999 Tilton, Jr.
5,922,026 A 7/1999 Chin
5,928,244 A 7/1999 Tovey et al.
5,948,000 A 9/1999 Larsen et al.
5,957,939 A 9/1999 Heaven et al.
5,957,953 A 9/1999 Dipoto et al.
5,968,044 A 10/1999 Nicholson et al.
5,980,557 A 11/1999 Iserin et al.
5,989,265 A 11/1999 Bouquet De La Joliniere et al.
5,997,552 A 12/1999 Person et al.
6,063,088 A 5/2000 Winslow
6,099,518 A 8/2000 Adams et al.
6,156,045 A 12/2000 Ulbrich et al.
6,179,840 B1 1/2001 Bowman
6,193,731 B1 2/2001 Oppelt et al.
6,193,733 B1 2/2001 Adams
6,245,072 B1 6/2001 Zdeblick et al.
6,302,885 B1 10/2001 Essiger
6,312,442 B1 11/2001 Kieturakis et al.
6,315,789 B1 11/2001 Cragg
6,318,616 B1 11/2001 Pasqualucci et al.
6,322,563 B1 11/2001 Cummings et al.
6,325,805 B1 12/2001 Ogilvie et al.
6,387,113 B1 5/2002 Hawkins et al.
6,391,333 B1 5/2002 Li et al.
6,413,274 B1 7/2002 Pedros
6,425,900 B1 7/2002 Knodel et al.
6,436,110 B2 8/2002 Bowman et al.
6,447,522 B2 9/2002 Gambale et al.
6,447,524 B1 9/2002 Knodel et al.
6,478,803 B1 11/2002 Kapec et al.
6,482,178 B1 11/2002 Andrews et al.
6,482,210 B1 11/2002 Skiba et al.
6,506,190 B1 1/2003 Walshe
6,508,803 B1 1/2003 Horikawa et al.
6,511,499 B2 1/2003 Schmieding et al.
6,517,564 B1 2/2003 Grafton et al.
6,524,316 B1 2/2003 Nicholson et al.
6,527,795 B1 3/2003 Lizardi
6,530,933 B1 3/2003 Yeung et al.
6,540,769 B1 4/2003 Miller, III
6,551,333 B2 4/2003 Kuhns et al.
6,554,852 B1 4/2003 Oberlander
6,569,186 B1 5/2003 Winters et al.
6,575,976 B2 6/2003 Grafton
6,599,286 B2 7/2003 Campin et al.
6,620,185 B1 9/2003 Harvie et al.
6,629,988 B2 10/2003 Weadock
6,638,297 B1 10/2003 Huitema
6,638,312 B2 10/2003 Plouhar et al.
6,639,365 B2 10/2003 Pruett
6,648,893 B2 11/2003 Dudasik
6,666,672 B1 12/2003 Steffens
6,666,872 B2 12/2003 Barreiro et al.
6,673,094 B1 1/2004 McDevitt et al.
6,685,728 B2 2/2004 Sinnott et al.
6,692,506 B1 2/2004 Ory et al.
6,723,099 B1 4/2004 Goshert
6,726,704 B1 4/2004 Loshakove et al.
6,726,705 B2 4/2004 Peterson et al.
6,740,100 B2 5/2004 Demopulos et al.
6,746,472 B2 6/2004 Frazier et al.
6,764,500 B1 7/2004 Muijs Van De Moer et al.
6,770,073 B2 8/2004 McDevitt et al.
6,779,701 B2 8/2004 Bailly et al.
6,800,081 B2 10/2004 Parodi
6,835,206 B2 12/2004 Jackson
6,849,078 B2 2/2005 Durgin et al.
6,887,259 B2 5/2005 Lizardi
6,926,723 B1 8/2005 Mulhauser et al.
6,932,834 B2 8/2005 Lizardi et al.
6,939,365 B1 9/2005 Fogarty et al.
6,946,003 B1 9/2005 Wolowacz et al.
6,949,117 B2 9/2005 Gambale et al.
6,964,685 B2 11/2005 Murray et al.
6,966,916 B2 11/2005 Kumar
6,972,027 B2 12/2005 Fallin et al.
6,984,241 B2 1/2006 Lubbers et al.
6,991,597 B2 1/2006 Gellman et al.
7,008,435 B2 3/2006 Cummins
7,021,316 B2 4/2006 Leiboff
7,025,772 B2 4/2006 Gellman et al.
7,033,379 B2 4/2006 Peterson
7,037,324 B2 5/2006 Martinek
7,048,171 B2 5/2006 Thornton et al.
7,063,711 B1 6/2006 Oshakove et al.
7,083,638 B2 8/2006 Foerster
7,087,064 B1 8/2006 Hyde
7,112,214 B2 9/2006 Peterson et al.
7,118,581 B2 10/2006 Fridén
7,141,072 B2 11/2006 Geistlich et al.
7,144,403 B2 12/2006 Booth
7,144,413 B2 12/2006 Wilford et al.
7,144,414 B2 12/2006 Harvie et al.
7,150,750 B2 12/2006 Damarati
7,153,314 B2 12/2006 Laufer et al.
7,160,314 B2 1/2007 Sgro et al.

(56) References Cited

U.S. PATENT DOCUMENTS 7,160,326 B2 1/2007 Ball
7,163,551 B2 1/2007 Anthony et al.
7,163,563 B2 1/2007 Schwartz et al.
7,169,157 B2 1/2007 Kayan
7,189,251 B2 3/2007 Kay
7,201,754 B2 4/2007 Stewart et al.
7,214,232 B2 5/2007 Bowman et al.
7,226,469 B2 6/2007 Benavitz et al.
7,229,452 B2 6/2007 Kayan
7,247,164 B1 7/2007 Ritchart et al.
7,303,577 B1 12/2007 Dean
7,309,337 B2 12/2007 Colleran et al.
7,320,692 B1 1/2008 Bender et al.
7,320,701 B2 1/2008 Haut et al.
7,322,935 B2 1/2008 Palmer et al.
7,326,231 B2 2/2008 Phillips et al.
7,343,920 B2 3/2008 Toby et al.
7,368,124 B2 5/2008 Chun et al.
7,377,934 B2 5/2008 Lin et al.
7,381,213 B2 6/2008 Lizardi
7,390,329 B2 6/2008 Westra et al.
7,399,304 B2 7/2008 Gambale et al.
7,404,824 B1 7/2008 Webler et al.
7,416,554 B2 8/2008 Lam et al.
7,452,368 B2 11/2008 Liberatore et al.
7,460,913 B2 12/2008 Kuzma et al.
7,463,933 B2 12/2008 Wahlstrom et al.
7,465,308 B2 12/2008 Sikora et al.
7,481,832 B1 1/2009 Meridew et al.
7,485,124 B2 2/2009 Kuhns et al.
7,497,854 B2 3/2009 Gill et al.
7,500,972 B2 3/2009 Voegele et al.
7,500,980 B2 3/2009 Gill et al.
7,500,983 B1 3/2009 Kaiser et al.
7,503,474 B2 3/2009 Hillstead et al.
7,506,791 B2 3/2009 Omaits et al.
7,559,941 B2 7/2009 Zannis et al.
7,572,276 B2 8/2009 Lim et al.
7,585,311 B2 9/2009 Green et al.
7,766,208 B2 8/2010 Epperly et al.
7,771,440 B2 8/2010 Ortiz et al.
7,776,057 B2 8/2010 Laufer et al.
7,780,685 B2 8/2010 Hunt et al.
7,785,255 B2 8/2010 Malkani
7,799,089 B2 9/2010 Plouhar et al.
7,807,192 B2 10/2010 Li et al.
7,819,880 B2 10/2010 Zannis et al.
7,846,171 B2 12/2010 Kullas et al.
7,867,222 B1 1/2011 Tilton, Jr. et al.
7,918,879 B2 4/2011 Yeung et al.
8,114,101 B2 2/2012 Criscuolo et al.
8,197,837 B2 6/2012 Jamiolkowski et al.
8,221,440 B2 7/2012 Kullas et al.
8,585,773 B1 11/2013 Kucklick
8,668,718 B2 3/2014 Euteneuer et al.
8,763,878 B2 7/2014 Euteneuer et al.
8,815,594 B2 8/2014 Harris et al.
8,821,536 B2 9/2014 Euteneuer et al.
8,821,537 B2 9/2014 Euteneuer et al.
8,840,642 B2 9/2014 Euteneuer et al.
8,864,780 B2 10/2014 Euteneuer et al.
8,894,661 B2 11/2014 McDevitt et al.
8,906,045 B2 12/2014 Levin et al.
8,920,464 B2 12/2014 Euteneuer et al.
8,968,329 B2 3/2015 Cabrera
9,005,224 B2 4/2015 Euteneuer et al.
9,027,819 B2 5/2015 Euteneuer et al.
9,033,201 B2 5/2015 Euteneuer
9,095,337 B2 8/2015 Euteneuer et al.
9,101,460 B2 8/2015 Euteneuer et al.
9,107,661 B2 8/2015 Euteneuer et al.
9,113,977 B2 8/2015 Euteneuer et al.
9,125,650 B2 9/2015 Euteneuer et al.
9,179,910 B2 11/2015 Euteneuer et al.
9,179,961 B2 11/2015 Euteneuer et al.
9,198,750 B2 12/2015 Van Kampen et al.
9,198,751 B2 12/2015 Euteneuer et al.
9,204,940 B2 12/2015 Euteneuer et al.
9,247,978 B2 2/2016 Euteneuer et al.
9,259,220 B2 2/2016 Euteneuer et al.
9,271,726 B2 3/2016 Euteneuer
9,314,314 B2 4/2016 Euteneuer et al.
9,314,331 B2 4/2016 Euteneuer et al.
9,370,356 B2 6/2016 Euteneuer et al.
9,393,103 B2 7/2016 Van Kampen et al.
9,393,104 B2 7/2016 Kampen et al.
9,414,841 B2 8/2016 Euteneuer et al.
9,566,063 B2 2/2017 Euteneuer et al.
9,572,117 B2 2/2017 Cho et al.
9,572,649 B2 2/2017 Cohen
9,878,141 B2 1/2018 Kucklick
10,004,586 B2 6/2018 Derwin et al.
10,028,814 B2 7/2018 Levin et al.
10,034,961 B1 7/2018 Nie et al.
10,046,085 B2 8/2018 Imran et al.
10,314,689 B2 6/2019 Zenz-Olson et al.
10,568,622 B2 2/2020 Euteneuer et al.
10,835,368 B2 11/2020 Zenz-Olson et al.
10,874,503 B2 12/2020 Zenz-Olson et al.
10,987,210 B2 4/2021 Zenz-Olson et al.
2002/0013627 A1 1/2002 Geistlich et al.
2002/0038151 A1 3/2002 Plouhar et al.
2002/0077687 A1 6/2002 Ahn
2002/0090725 A1 7/2002 Simpson et al.
2002/0123767 A1 9/2002 Prestel
2002/0165559 A1 11/2002 Grant et al.
2003/0073979 A1 4/2003 Naimark et al.
2003/0125748 A1 7/2003 Li et al.
2003/0212456 A1 11/2003 Ipchitz et al.
2004/0059416 A1 3/2004 Murray et al.
2004/0073219 A1 4/2004 Skiba et al.
2004/0082969 A1 4/2004 Kerr
2004/0138705 A1 7/2004 Heino et al.
2004/0167519 A1 8/2004 Weiner et al.
2004/0220574 A1 11/2004 Pelo et al.
2005/0015021 A1 1/2005 Shiber
2005/0049618 A1 3/2005 Masuda et al.
2005/0051597 A1 3/2005 Toledano
2005/0059996 A1 3/2005 Bauman et al.
2005/0060033 A1 3/2005 Vacanti et al.
2005/0107807 A1 5/2005 Nakao
2005/0113736 A1 5/2005 Orr et al.
2005/0171569 A1 8/2005 Girard et al.
2005/0177249 A1 8/2005 Kladakis et al.
2005/0187576 A1 8/2005 Whitman et al.
2005/0240222 A1 10/2005 Shipp
2005/0274768 A1 12/2005 Cummins et al.
2006/0074423 A1 4/2006 Alleyne et al.
2006/0178743 A1 8/2006 Carter
2006/0235442 A1 10/2006 Huitema
2006/0293760 A1 12/2006 DeDeyne
2007/0078477 A1 4/2007 Heneveld et al.
2007/0083236 A1 4/2007 Sikora et al.
2007/0112361 A1 5/2007 Schonholz et al.
2007/0179531 A1 8/2007 Thornes
2007/0185506 A1 8/2007 Jackson
2007/0190108 A1 8/2007 Datta et al.
2007/0219558 A1 9/2007 Deutsch
2007/0260324 A1 11/2007 Joshi et al.
2007/0270804 A1 11/2007 Chudik
2007/0288023 A1 12/2007 Pellegrino et al.
2008/0027470 A1 1/2008 Hart et al.
2008/0051888 A1 2/2008 Ratcliffe et al.
2008/0065153 A1 3/2008 Allard et al.
2008/0090936 A1 4/2008 Fujimura et al.
2008/0125644 A1 5/2008 Lubock et al.
2008/0125766 A1 5/2008 Lubock et al.
2008/0125869 A1 5/2008 Paz et al.
2008/0135600 A1 6/2008 Hiranuma et al.
2008/0173691 A1 7/2008 Mas et al.
2008/0188874 A1 8/2008 Henderson
2008/0188936 A1 8/2008 Ball et al.
2008/0195119 A1 8/2008 Ferree
2008/0200949 A1 8/2008 Hiles et al.

(56) References Cited

U.S. PATENT DOCUMENTS

2008/0241213 A1 10/2008 Chun et al.
2008/0255561 A1 10/2008 Tormala et al.
2008/0272173 A1 11/2008 Coleman et al.
2008/0294174 A1 11/2008 Bardsley et al.
2008/0306408 A1 12/2008 Lo
2009/0001122 A1 1/2009 Prommersberger et al.
2009/0012521 A1 1/2009 Axelson, Jr. et al.
2009/0018655 A1 1/2009 Brunelle et al.
2009/0030434 A1 1/2009 Paz et al.
2009/0069806 A1 3/2009 De La Mora Levy et al.
2009/0076541 A1 3/2009 Chin et al.
2009/0105535 A1 4/2009 Green et al.
2009/0112085 A1 4/2009 Eby
2009/0134198 A1 5/2009 Knodel et al.
2009/0156986 A1 6/2009 Trenhaile
2009/0156997 A1 6/2009 Trenhaile
2009/0182245 A1 7/2009 Zambelli
2009/0242609 A1 10/2009 Kanner
2009/0299401 A1 12/2009 Tilson
2010/0145367 A1 6/2010 Ratcliffe
2010/0147922 A1 6/2010 Olson
2010/0163598 A1 7/2010 Belzer
2010/0191332 A1 7/2010 Euteneuer et al.
2010/0241227 A1 9/2010 Euteneuer et al.
2010/0249801 A1 9/2010 Sengun et al.
2010/0256675 A1 10/2010 Romans
2010/0274278 A1 10/2010 Fleenor et al.
2010/0292715 A1 11/2010 Nering et al.
2010/0292791 A1 11/2010 Lu et al.
2010/0312250 A1 12/2010 Euteneuer et al.
2010/0312275 A1 12/2010 Euteneuer et al.
2010/0327042 A1 12/2010 Amid et al.
2011/0000950 A1 1/2011 Euteneuer et al.
2011/0004221 A1 1/2011 Euteneuer et al.
2011/0011407 A1 1/2011 Townsend et al.
2011/0011917 A1 1/2011 Loulmet
2011/0034942 A1 2/2011 Levin et al.
2011/0040310 A1 2/2011 Levin et al.
2011/0040311 A1 2/2011 Levin et al.
2011/0054485 A1 3/2011 Kullas et al.
2011/0066166 A1 3/2011 Levin et al.
2011/0106154 A1 5/2011 DiMatteo et al.
2011/0114700 A1 5/2011 Baxter, III et al.
2011/0224702 A1 9/2011 Van Kampen et al.
2011/0264149 A1 10/2011 Pappalardo et al.
2012/0100200 A1 4/2012 Belcheva et al.
2012/0160893 A1 6/2012 Harris et al.
2012/0193391 A1 8/2012 Michler et al.
2012/0209401 A1 8/2012 Euteneuer et al.
2012/0211543 A1 8/2012 Euteneuer
2012/0248171 A1 10/2012 Bailly et al.
2012/0316608 A1 12/2012 Foley
2013/0035704 A1 2/2013 Dudai
2013/0053825 A1 2/2013 Moulton et al.
2013/0103100 A1 4/2013 Ruffieux
2013/0110156 A1 5/2013 Nakayama et al.
2013/0153627 A1 6/2013 Euteneuer et al.
2013/0153628 A1 6/2013 Euteneuer
2013/0158554 A1 6/2013 Euteneuer et al.
2013/0158587 A1 6/2013 Euteneuer et al.
2013/0158661 A1 6/2013 Euteneuer et al.
2013/0172920 A1 7/2013 Euteneuer et al.
2013/0172997 A1 7/2013 Euteneuer et al.
2013/0184716 A1 7/2013 Euteneuer et al.
2013/0240598 A1 9/2013 Euteneuer et al.
2013/0245627 A1 9/2013 Euteneuer et al.
2013/0245682 A1 9/2013 Euteneuer et al.
2013/0245683 A1 9/2013 Euteneuer et al.
2013/0245706 A1 9/2013 Euteneuer et al.
2013/0245707 A1 9/2013 Euteneuer et al.
2013/0245762 A1 9/2013 Van Kampen et al.
2013/0245774 A1 9/2013 Euteneuer et al.
2013/0325108 A1 12/2013 Imran et al.
2014/0161841 A1 6/2014 Harris et al.
2014/0188161 A1 7/2014 Euteneuer et al.
2014/0288593 A1 9/2014 Euteneuer et al.
2014/0371853 A1 12/2014 Kampen et al.
2015/0025630 A1 1/2015 Euteneuer et al.
2015/0112370 A1 4/2015 Euteneuer et al.
2015/0182326 A1 7/2015 Euteneuer et al.
2015/0209127 A1 7/2015 Cohen
2015/0230792 A1 8/2015 Euteneuer et al.
2015/0238190 A1 8/2015 Euteneuer
2015/0250477 A1 9/2015 Euteneuer et al.
2015/0272573 A1 10/2015 Euteneuer et al.
2015/0313705 A1 11/2015 Euteneuer et al.
2015/0320543 A1 11/2015 Zenz-Olson
2015/0327858 A1 11/2015 Euteneuer et al.
2015/0327975 A1 11/2015 Euteneuer et al.
2016/0030150 A1 2/2016 Euteneuer et al.
2016/0030157 A1 2/2016 Euteneuer et al.
2016/0051300 A1 2/2016 Euteneuer et al.
2016/0058534 A1 3/2016 Derwin et al.
2016/0058535 A1 3/2016 Euteneuer et al.
2016/0100935 A1 4/2016 Euteneuer et al.
2016/0113644 A1 4/2016 Diduch et al.
2016/0120538 A1 5/2016 Westling et al.
2016/0120542 A1 5/2016 Westling et al.
2016/0128693 A1 5/2016 Euteneuer et al.
2016/0135806 A1 5/2016 Euteneuer
2016/0256254 A1 9/2016 Kucklick
2016/0256258 A1 9/2016 Euteneuer et al.
2016/0262747 A1 9/2016 Euteneuer et al.
2016/0262780 A1 9/2016 Kucklick
2016/0296318 A1 10/2016 Van Kampen et al.
2016/0317147 A1 11/2016 Euteneuer et al.
2016/0317281 A1 11/2016 Van Kampen et al.
2016/0324616 A1 11/2016 Zenz-Olson et al.
2016/0361155 A1 12/2016 Van Kampen
2017/0181830 A1 6/2017 Felix et al.
2017/0181832 A1 6/2017 Felix et al.
2017/0181833 A1 6/2017 Felix et al.
2017/0189164 A1 7/2017 Zenz-Olson et al.
2018/0085493 A1 3/2018 Lee
2018/0193519 A1 7/2018 Nie et al.
2018/0333246 A1 11/2018 Levin et al.
2019/0030211 A1 1/2019 Nam et al.
2019/0110885 A1 4/2019 Zenz-Olson et al.
2019/0175328 A1 6/2019 Zenz-Olson et al.
2019/0314142 A1 10/2019 Zenz-Olson et al.
2020/0237499 A1 7/2020 Zenz-Olson et al.
2021/0052366 A1 2/2021 Zenz-Olson et al.
2021/0100648 A1 4/2021 Zenz-Olson et al.
2021/0113243 A1 4/2021 Zenz-Olson et al.
2023/0058024 A1 2/2023 Zenz-Olson et al.

FOREIGN PATENT DOCUMENTS

CA 2945821 A1 11/2015
CN 108236533 A 7/2018
CN 110225726 A 9/2019
EP 0142225 A1 5/1985
EP 0298400 A1 1/1989
EP 0390613 A1 10/1990
EP 0543499 A1 5/1993
EP 0548998 A1 6/1993
EP 0557963 A1 9/1993
EP 0589306 A2 3/1994
EP 0908152 A1 4/1999
EP 1114618 A2 7/2001
EP 1491157 A1 12/2004
EP 1559379 A1 8/2005
EP 2030576 A2 3/2009
EP 2097021 A2 9/2009
GB 2154688 A 9/1985
GB 2397240 A 7/2004
JP 58188442 A 11/1983
JP 2005586122 A 3/2005
JP 2006515774 A 6/2006
JP 2007175297 A 7/2007
JP 2012528703 A 11/2012
JP 2014524333 A 9/2014
JP 2024501797 A 1/2024
WO 8505025 A1 11/1985

(56) References Cited

FOREIGN PATENT DOCUMENTS

| | | | |
|---|---|---|---|
| WO | 0176456 | A2 | 10/2001 |
| WO | 0191644 | A1 | 12/2001 |
| WO | 0234140 | A2 | 5/2002 |
| WO | 2003105670 | A2 | 12/2003 |
| WO | 2004000138 | A1 | 12/2003 |
| WO | 2004093690 | A1 | 11/2004 |
| WO | 2005016389 | A2 | 2/2005 |
| WO | 2006086679 | A1 | 8/2006 |
| WO | 2007014910 | A1 | 2/2007 |
| WO | 2007030676 | A2 | 3/2007 |
| WO | 2007078978 | A2 | 7/2007 |
| WO | 2007082088 | A2 | 7/2007 |
| WO | 2008063636 | A2 | 5/2008 |
| WO | 2008111073 | A2 | 9/2008 |
| WO | 2008111078 | A2 | 9/2008 |
| WO | 2008139473 | A2 | 11/2008 |
| WO | 2009079211 | A1 | 6/2009 |
| WO | 2009143331 | A1 | 11/2009 |
| WO | 2010081029 | A1 | 7/2010 |
| WO | 2010141906 | A1 | 12/2010 |
| WO | 2011095890 | A2 | 8/2011 |
| WO | 2011128903 | A2 | 10/2011 |
| WO | 2011140382 | A1 | 11/2011 |
| WO | 20130101638 | A1 | 7/2013 |
| WO | 2014070903 | A2 | 5/2014 |
| WO | 2017117415 | A1 | 7/2017 |
| WO | 2017213893 | A1 | 12/2017 |
| WO | 2018144887 | A1 | 8/2018 |
| WO | 2021202888 | A1 | 10/2021 |
| WO | 2022031511 | A1 | 2/2022 |
| WO | 2022132634 | A1 | 6/2022 |

OTHER PUBLICATIONS

Alexander et al., "Ligament and tendon repair with an absorbable polymer-coated carbon fiber stent," Bulletin of the Hospital for Joint Diseases Orthopaedic Institute, 46(2):155-173, 1986.

Bahler et al., "Trabecular bypass stents decrease intraocular pressure in cultured himan anterior segments," Am. J. Opthamology, 138(6):988-994, Dec. 2004.

Chamay et al., "Digital contracture deformity after implantation of a silicone prosthesis: Light and electron microscopic study," The Journal of Hand Surgery, 3(3):266-270, May 1978.

D'Ermo et al., "Our results of the operation of ab externo," Opthalmologica, 168: 347-355, 1971.

France et al., "Biomechanical evaluation of rotator cuff fixation methods," The American Journal of Sports Medicine, 17(2), 1989.

Goodship et al., "An assessment of filamentous carbon fibre for the treatment of tendon injury in the horse," Veterinary Record, 106: 217-221, Mar. 8, 1980.

Hunter et al., "Flexor-tendon reconstruction in severely damaged hands," The Journal of Bone and Joint Surgery (American Volume), 53-A(5): 329-358, Jul. 1971.

Johnstone et al., "Microsurgery of Schlemm's canal and the human aqueous outflow system," Am. J. Opthamology, 76(6): 906-917, Dec. 1973.

Kowalsky et al., "Evaluation of suture abrasion against rotator cuff tendon and proximal humerus bone," Arthroscopy: The Journal of Arthroscopic and Related Surgery, 24(3):329-334, Mar. 2008.

Lee et al., "Aqueous-venous and intraocular pressure. Preliminary report of animal studies," Investigative Opthalmology, 5(1): 59-64, Feb. 1966.

Maepea et al., "The pressures in the episcleral veins, Schlemm's canal and the trabecular meshwork in monkeys: Effects of changes in intraocular pressure," Exp. Eye Res., 49:645-663, 1989.

Nicolle et al., "A silastic tendon prosthesis as an adjunct to flexor tendon grafting: An experimental and clinical evaluation," British Journal of Plastic Surgery, 22(3-4):224-236, 1969.

Rubin et al., "The use of acellular biologic tissue patches in foot and ankle surgery," Clinics in Podiatric Medicine and Surgery, 22:533-552, 2005.

Schultz, "Canaloplasty procedure shows promise for open-angle glaucoma in European study," Ocular Surgery News, 34-35, Mar. 1, 2007.

Spiegel et al., "Schlemm's canal implant: a new method to lower intraocular pressure in patients with POAG," Opthalmic Surgery and Lasers, 30(6):492-494, Jun. 1999.

Stenson et al., "Arthroscopic treatment of partial rotator cuff tears," Operative Techniques in Sports Medicine, 12 (2):135-148, Apr. 2004.

Valdez et al., "Repair of digital flexor tendon lacerations in the horse, using carbon fiber implants," JAYMA, 177(5):427-435, Sep. 1, 1980.

Hewitt et al., "The Mechanical Properties of Human Hip Capsule Ligaments," The Journal of Arthroplasty, vol. 17 No. 1, 8 pages, 2002.

Hewitt et al., "Regional Material Properties of the Human Hip Joint Capsule Ligaments," Journal of Orthopaedic Research vol. 19, pp. 359-364, 2001.

Stewart et al., "Spatial Distribution of Hip Capsule Structural and Material Properties," Journal of Biomechanics vol. 35, pp. 1491-1498, 2002.

Kuhns et al., "Capsular Management in Hip Arthroscopy: An Anatomic, Biomechanical, and Technical Review," Frontiers in Surgery, vol. 3 Article 13, 10 pages, Mar. 2016.

Rakhra et al.,"Is the Hip Capsule Thicker in Diseased Hips?", Bone Joint Res 2016; vol. 5, No. 11, pp. 586-593, Nov. 2016.

Schleifenbaum et al.,"Tensile Properties fo the Hip Joint Ligament are Largely Variable and Age-Dependent—An In-Vitro Analysis in an Age Range of 14-93 years," Journal of Biomechanics, vol. 49, pp. 3437-3443, 2016.

International Search Report and Written Opinion dated Aug. 12, 2021 for International Application No. PCT/US2021/021935.

Dyrna et al., "Human Subacromial Bursal Cells Display Superior Engraftment Versus Bone Marrow Stromal Cells in Murine Tendon Repair," Am J Sports Med. 46 (14), pp. 3511-3520, Dec. 2018.

International Search Report and Written Opinion for Application No. PCT/US2016/069261, 24 pages, date mailed Mar. 29, 2017.

International Search Report and Written Opinion for Application No. PCT/US2021/063083, 20 pages, date mailed Jun. 8, 2022.

Office Action Application No. 2017-556679, 10 pages, dated Jun. 19, 2018.

Notification of Transmittal of the International Search Report and the Written Opinion of the International Searching Authority, or the Declaration for Application No. PCT/US2016/030949, 17 pages, dated Oct. 4, 2016.

Invitation to Pay Additional Fees, for International Application No. PCT/US2016/030949, 7 pages, dated Aug. 10, 2016.

146
142
168
150
158
160
166
164a
156
162a
164b
154
165a
164c
150
165b
144
162b
152
182
167b
152
167a
164c 82
316
317
319
322
82

82
616
600
620b
615
614
607
620a
612
32
34

MEDICAL IMPLANT DELIVERY SYSTEM AND RELATED METHODS

CROSS REFERENCE TO RELATED APPLICATIONS

This application is a continuation of International Application PCT/US2021/063083 filed on Dec. 13, 2021, which claims the benefit of U.S. Patent Application Ser. No. 63/126,458 filed on Dec. 16, 2020, the disclosures of which are incorporated herein by reference.

TECHNICAL FIELD

The present disclosure pertains generally, but not by way of limitation, to orthopedic implants, implant delivery systems, and methods of treatment. More particularly, the present disclosure relates to a tendon repair implant delivery device for arthroscopic placement of a sheet-like tissue implant over or in the area of a full or partial thickness tear of a tendon, such as the supraspinatus tendon of the shoulder.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. There is an ongoing need to deliver and adequately position medical implants during an arthroscopic procedure in order to treat injuries to the rotator cuff, rotator cuff tendons, or other soft tissue or tendon injuries throughout a body.

BRIEF SUMMARY

This disclosure provides design, material, manufacturing method, and use alternatives for medical devices.

A first example includes an implant delivery system. The implant delivery system includes a delivery shaft and a detachable frame. The delivery shaft includes a proximal portion and a distal portion. The detachable frame is coupled to the distal portion of the delivery shaft. The detachable frame includes a body portion and a plurality of attachment arms extending away from the body portion. The body portion further includes a first support strut positioned adjacent to a second support strut. The first support strut converges with the second support strut at a first convergence region. A first attachment arm of the plurality of attachment arms extends away from the first convergence region.

Additionally or alternatively, the first support strut and the second support strut are arranged in a substantially triangular geometry.

Additionally or alternatively, the body portion further includes a third support strut positioned adjacent to a fourth support strut. The third support strut converges with the fourth support strut at a second convergence region. A second attachment arm of the plurality of attachment arms extends away from the second convergence region.

Additionally or alternatively, the second support strut converges with the fourth support strut.

Additionally or alternatively, the plurality of attachment arms are configured to be attached to an implant.

Additionally or alternatively, the first attachment arm and the second attachment arm extend away from one another.

Another example includes an implant delivery system. The implant delivery system includes a delivery shaft and a connection assembly. The delivery shaft includes a proximal end region and a distal end region. The connection assembly is coupled to the delivery shaft. The connection assembly includes a tack member attached to a tack disk. The tack disk is further attached to a collar. The collar is configured to extend into and engage the distal end region of the delivery shaft.

Additionally or alternatively, the distal end region of the delivery shaft includes a lumen having a first profile, and wherein the connection member includes a cross-section having a second profile, and wherein the first profile is configured to mate with the second profile.

Additionally or alternatively, the cross-sectional profile of the connection member is ovular.

Additionally or alternatively, the connection member is designed to disengage from the distal end region of the delivery shaft.

Additionally or alternatively, the tack member includes a distal end region and a proximal end region. The distal end region is coupled to the tack disk and the distal end region includes a pointed tip.

Additionally or alternatively, the implant delivery system includes a detachable frame having a plurality of connector legs, wherein at least one the plurality of connector legs is disposed between the tack disk and the collar.

Additionally or alternatively, the implant delivery system includes a tether attached to the connection assembly. At least a portion of the tether extends within a portion of a lumen of the delivery shaft. The tether remains attached to the connection assembly when the collar is disengaged from the delivery shaft.

Additionally or alternatively, the tether is designed to be retracted within the lumen of the delivery shaft, and wherein retraction of the tether is designed to release a detachable frame from an implant.

Another example is an implant delivery system. The implant delivery system includes a handle, a delivery shaft, and a tether. The handle has a distal end and a proximal end. The delivery shaft has a distal end, a proximal end and a lumen extending therein. The proximal end attaches to a portion of the handle. The tether extends within at least a portion of both the handle and the lumen of the delivery shaft. The handle has a proximal end and a distal end. The distal end of the tether is coupled to a connection assembly and the proximal end of the tether extends from the handle.

Additionally or alternatively, the handle further includes a tether clamp configured to lock the tether to the handle.

Additionally or alternatively, locking the tether to the handle prevents the tether from translating with respect to the handle, the delivery shaft or both the handle and the delivery shaft.

Additionally or alternatively, unlocking the tether clamp permits the tether to translate with respect to the handle, the delivery shaft or both the handle and the delivery shaft.

Additionally or alternatively, the connection assembly further includes a tack member, and wherein the distal end of the tether is attached to the tack member.

Additionally or alternatively, the implant delivery system includes a detachable frame coupled to the connection assembly.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
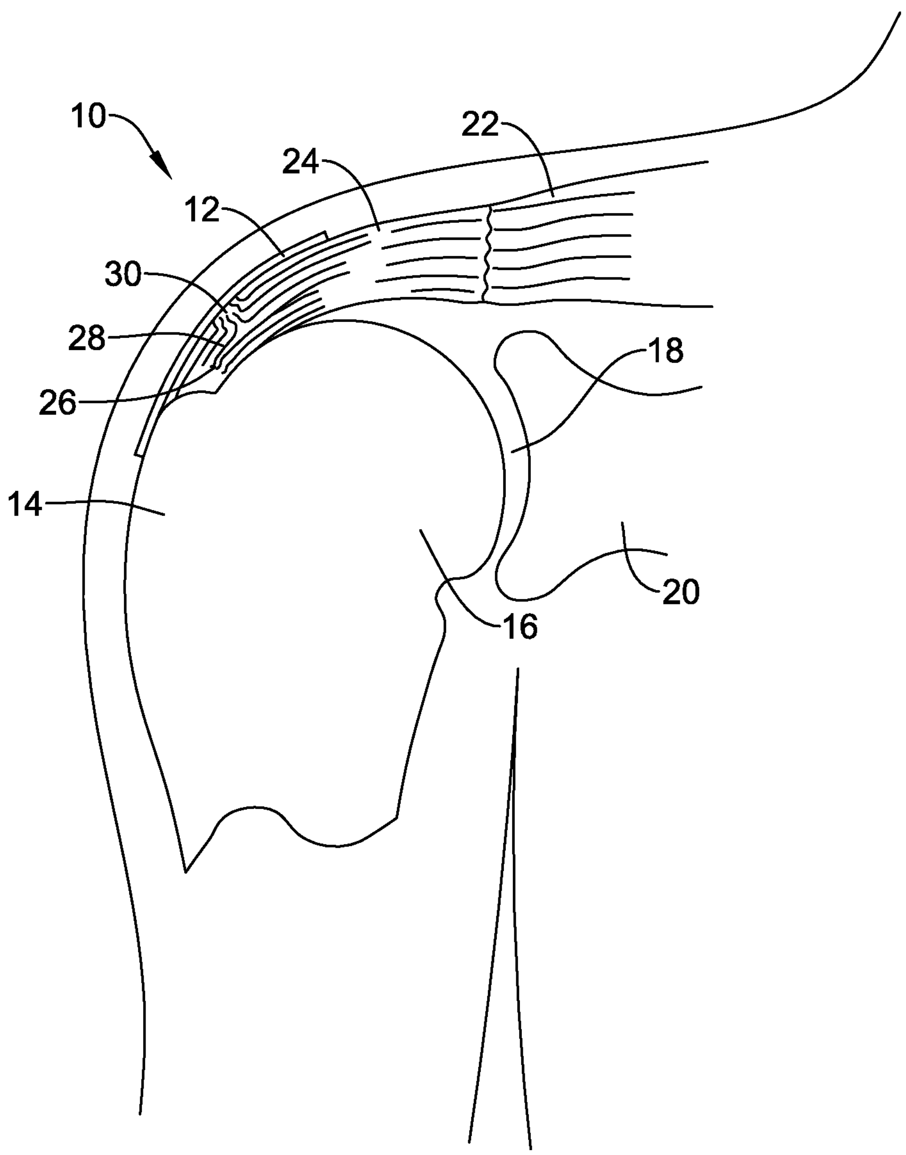
FIG. 1 illustrates a cross-section of an anterior view of a shoulder of a patient.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. An accepted treatment for rotator cuff tears may include reattaching the torn tendon to the humeral head using sutures. Additionally, in treating rotator cuff tears, an accepted practice may also include the placement of a scaffold over the repaired tendon to mechanically reinforce the repaired tendon and/or promote tissue reformation. Therefore, there is an ongoing need to deliver and adequately position medical implants during an arthroscopic procedure in order to treat injuries to the rotator cuff, rotator cuff tendons, or other soft tissue or tendon injuries throughout a body.

FIG. 1 shows a cross-sectional view of a shoulder 10 including an example implant 12. The shoulder 10 further shows a head 14 of the humerus 16 mating with a glenoid fossa 18 of the scapula 20. The glenoid fossa 18 comprises a shallow depression in the scapula 20. A supraspinatus tendon 22 is also shown. These muscles (along with others) control the movement of the humerus 16 relative to the scapula 20. A distal tendon 24 of the supraspinatus tendon 22 meets the humerus 16 at an insertion point 26.

In FIG. 1, the tendon 24 includes a damaged portion 28 located near the insertion point 26. The damaged portion 28 includes a tear 30 extending partially through the tendon 24. The tear 30 may be referred to as a partial thickness tear. The depicted partial thickness tear 30 is on the bursal side of the tendon, however, the tear may also be on the opposite or articular side of the tendon 24 and/or may include internal tears to the tendon 24 not visible on either surface.

FIG. 1 further illustrates that the tendon repair implant 12 has been placed over the partial thickness tear 30. In this example, the tendon repair implant 12 is placed on the bursal side of the tendon regardless of whether the tear is on the bursal side, articular side or within the tendon. Further, the tendon repair implant 12 may overlay multiple tears.

In some instances, delivery of an implant 12 (e.g., a sheet-like implant) to a target site of a patient may require a physician to create an incision in the patient sufficient to access the target implant site. After creating this access site, the physician may insert an implant delivery system through the access site and position the distal end of the implant delivery system adjacent the target implant site. The physician may then manipulate the implant delivery system to deploy an implant out of a delivery sheath adjacent the target implant site.

Figure 2:
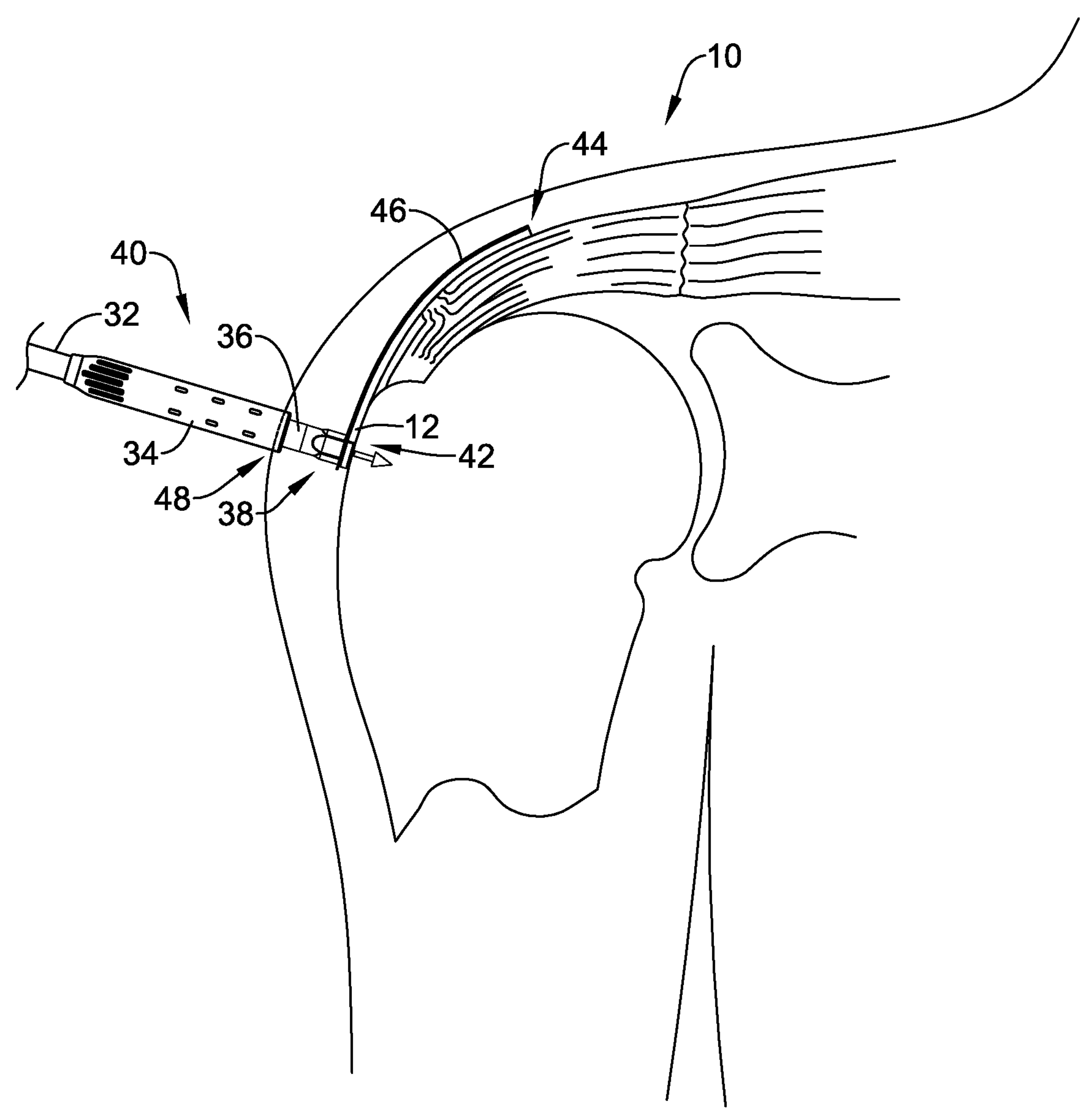
FIG. 2 illustrates a shoulder including a head of the humerus mating with the glenoid fossa of the scapula at a glenohumeral joint and an implant being affixed to a tendon using an implant delivery device.

For example, FIG. 2 provides a perspective view of an implant delivery system 40 extending through the shoulder 10 of a patient. FIG. 2 shows the implant delivery system deployed adjacent a target site (e.g., a tear in the supraspinatus tendon). In at least some embodiments, the implant delivery system 40 may include an outer shaft 32 (e.g., a cannula) including a proximal end (not shown), a distal end and a lumen extending within at least a portion of the outer shaft 32. In some examples, the distal end of the outer shaft 32 may be attached to a delivery sheath 34. In other words, the delivery sheath 34 may extend away from the distal end of the outer shaft 32 whereby the distal end of the outer shaft 32 may be attached to a proximal end of the delivery sheath 34. In some examples, the delivery sheath 34 may resemble a substantially cylindrical sheath, a portion of which may be over-molded onto the distal end of the outer shaft 32. As will be described in greater detail below, the delivery sheath 34 may be designed to house the tendon implant 12 in a rolled state as the implant delivery system 40 is advanced to the target site.

FIG. 2 further illustrates that the implant delivery system 40 may include an inner shaft 36 extending within the lumen of the outer shaft 32 and longitudinally movable relative thereto. The inner shaft 36 may include a proximal end (not shown) extending out of the proximal end of the outer shaft 32 and/or otherwise manipulatable relative to the outer shaft 32 by a user. Additionally, in some examples the proximal end of the inner shaft 36 and/or the outer shaft 32 may be coupled to a handle member (not shown). The handle member may be utilized to manipulate the inner shaft 36 relative to the outer shaft 32 and delivery sheath 34. For example, the handle member may be utilized to impart a rotational force to the inner shaft 36 and/or longitudinal movement of the inner shaft 36 relative to the outer shaft 32 and delivery sheath 34.

Additionally, the inner shaft 36 may include a distal end region 38 which is shown extending out of the distal end of the delivery sheath 34 in FIG. 2. Further, the inner shaft 36 may include a lumen extending therein. The lumen of the inner shaft 36 may extend along a portion or the entire length of the inner shaft 36 (e.g., from the distal end region 38 to the proximal end of the inner shaft 36).

The delivery system 40 may further include a frame 46 attached (e.g., detachably attached) to the distal end region 38 of the inner shaft 36. In some instances, the frame 46 may be detachable from the inner shaft 36 in vivo, as described herein. As shown in FIG. 2, the detachable frame 46 may be attached to an implant 12 (e.g., a sheet-like implant) for delivery and deployment at the target site. For purposes of the discussion herein, the combined structure including the frame 46 and the implant 12 may be defined as having a proximal end 42 and a distal end 44 as illustrated in FIG. 2.

When initially positioning the frame 46 and the implant 12 adjacent a target site, a clinician may orient the frame 46 and the implant 12 (for example, via a handle member attached to a proximal portion of the inner shaft 36) such that the proximal portion 42 may be adjacent (e.g., overlaid) on a portion of the humerus (e.g., on the bone), while the distal portion 44 of the frame 46 and the implant 12 may overlay the tendon 24.

As described above, delivery of the implant delivery system 40 may include the insertion of the outer shaft 32 and delivery sheath 34 through an access site (e.g., incision) and advancement to a target site with the detachable frame 46 and the implant 12 contained within a distal portion of the lumen of the delivery sheath 34. After positioning the distal end 48 of the delivery sheath 34 proximate the target site, a clinician may deploy the detachable frame 46 in combination with the implant 12 out of the lumen of the delivery sheath 34, such as by retracting the outer shaft 32 and delivery sheath 34 relative to the inner shaft 36 and the frame 46, and positioning the implant 12 and the frame 46 over the target site. The frame 46 and the implant 12 may automatically expand to an open state when unconstrained by the delivery sheath 34. As will be illustrated and described in greater detail below, in some examples, the frame 46 may be "shape set" such that its deployed configuration may generally match the curvature of the humeral head. In other words, the frame 46 may expand to a substantially curved configuration which matches the curvature of the humeral head when unconstrained by the delivery sheath 34.

As discussed above, prior to deployment, the detachable frame 46 and the implant 12 combination may be contained (e.g., housed) within the lumen of the delivery sheath 34 for subsequent deployment distally out the distal opening of the delivery sheath 34. The combination of the detachable frame 46 and the implant 12 may wrap and/or fold upon itself such that it may be positioned within the lumen of the delivery sheath 34. Alternatively, the detachable frame 46 and the implant 12 may wrap and/or fold around the implant inner shaft 36 while disposed within the delivery sheath 34.

Figure 3:
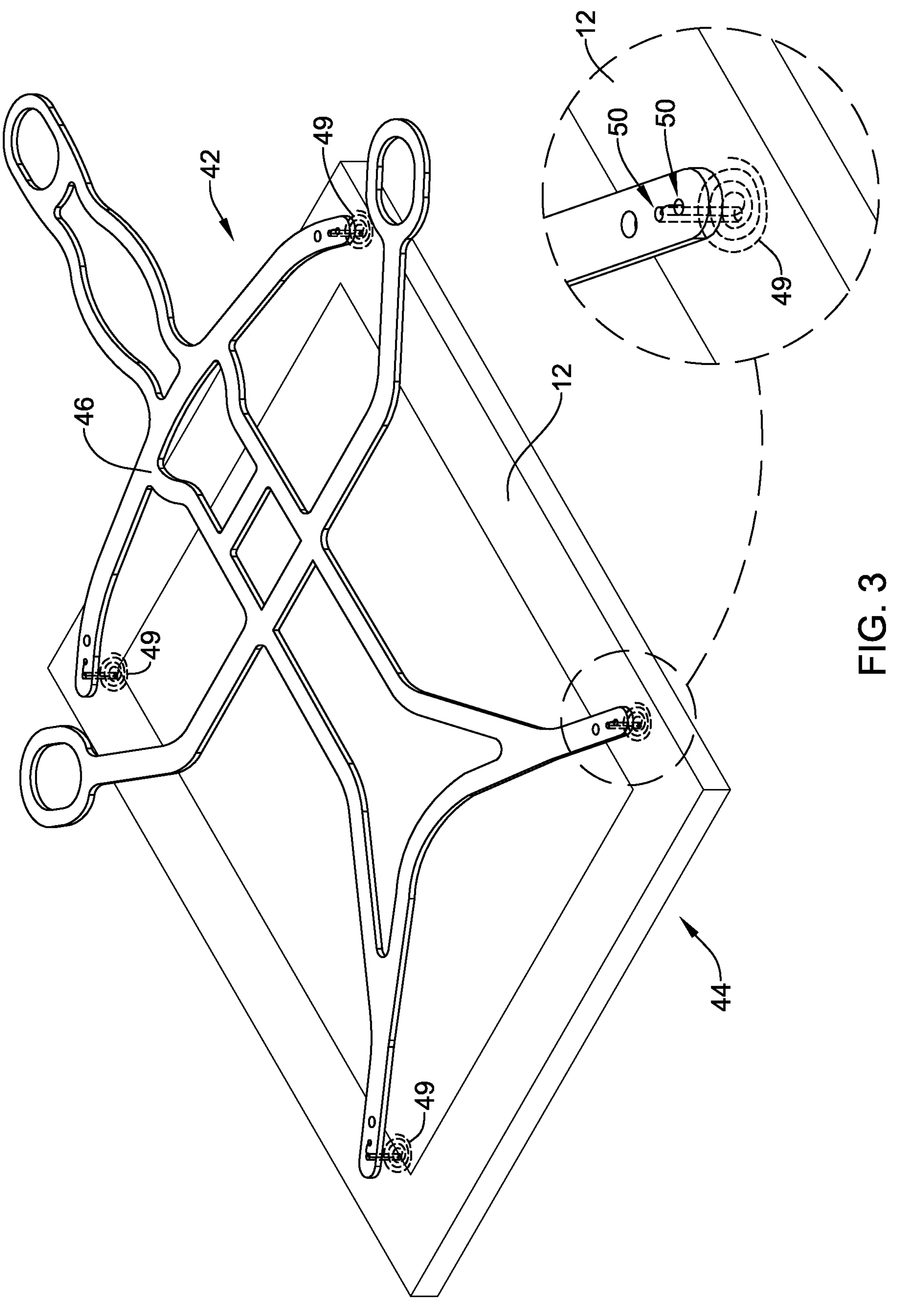
FIG. 3 illustrates an example implant delivery device attached to an implant.

FIG. 3 shows an example detachable frame 46 attached to an example implant 12. As stated above with reference to FIG. 2, the detachable frame 46 and the implant 12 may have a proximal portion 42 which, for purposes of discussion herein, may be adjacent the connection to the inner shaft 36 and be configured to be positioned adjacent the humerus 16.

Further, the detachable frame 46 and the implant 12 may have a distal portion 44 which, for purposes of discussion herein, may extend away from the deliver shaft 36 and be configured to be positioned adjacent the tendon 24.

Figure 5:
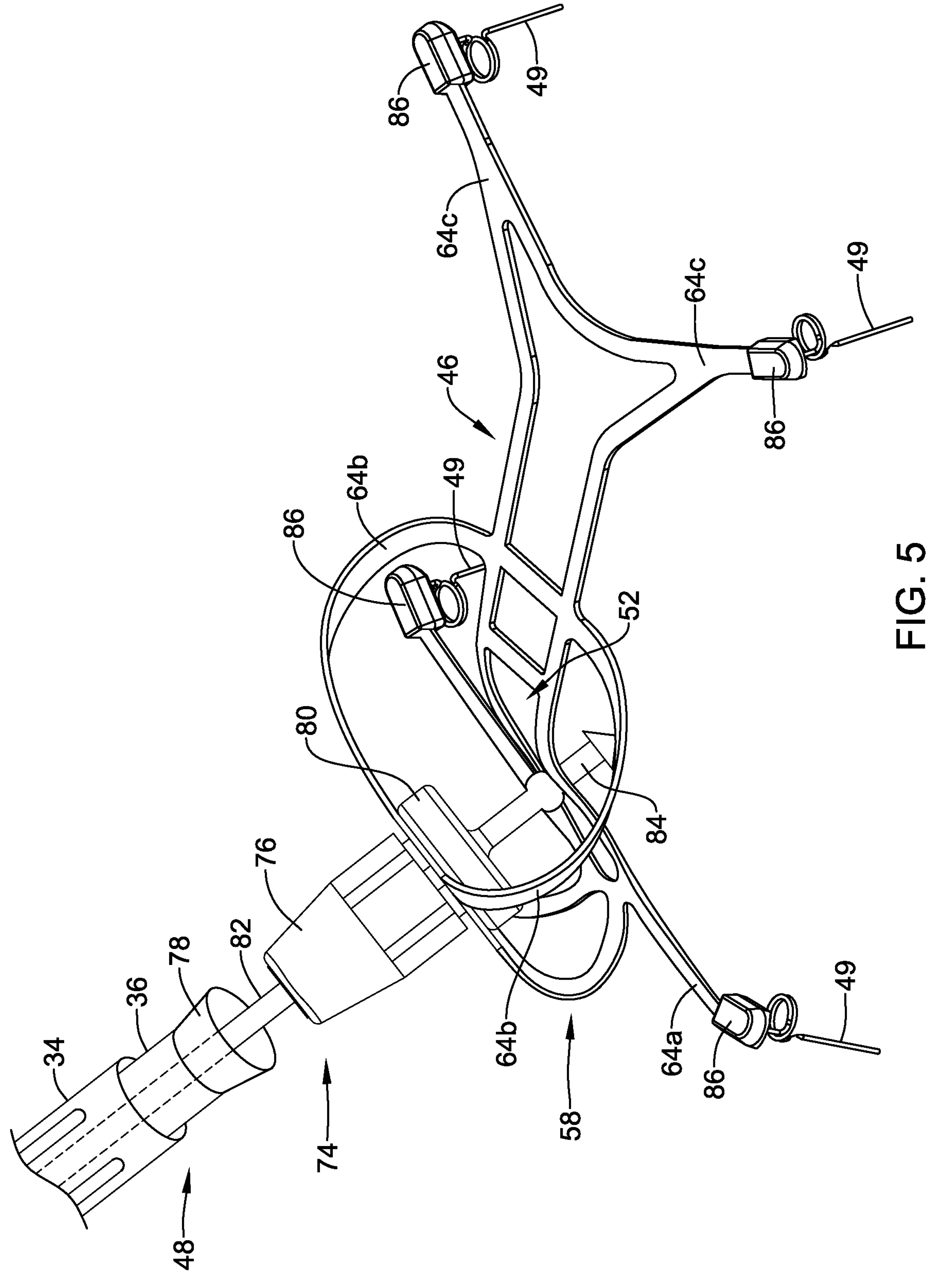
FIG. 5 illustrates the implant delivery device of FIG. 4 attached to an example implant delivery system.

As will be discussed in greater detail below with respect to FIG. 5, FIG. 3 illustrates that the frame 46 may include one or more coil attachment members 49 which may be utilized to releasably couple the frame 46 to the implant 12. FIG. 3 illustrates that the frame 46 may be attached to the implant 12 using four attachment members 49, however, it is contemplated that more (or less) than four attachment members 49 may be utilized to releasably attach the frame 46 to the implant 12. It can be further appreciated from the detailed view in FIG. 3 that a first portion of the coil attachment member 49 may be threaded through one or more of the attachment apertures 50 located on the frame 46 while a second portion of the attachment member 49 may be coiled on the bottom side of the implant 12, whereby the implant 12 is sandwiched between the coiled portion of the attachment member 49 and the frame 46. A more detailed discussion of the attachment members 49 is set forth below with respect to FIG. 5.

Figure 4:
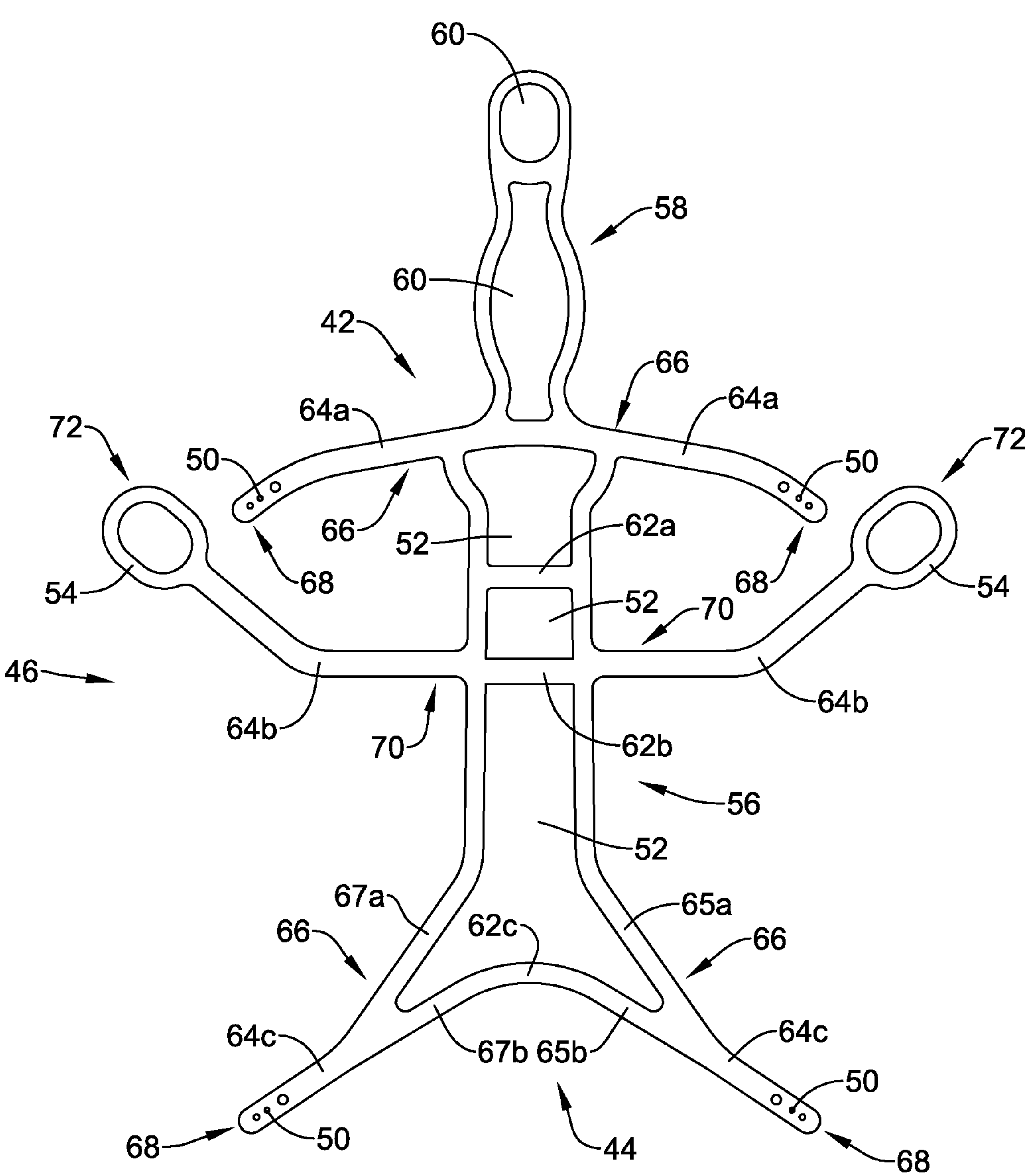
FIG. 4 illustrates an example implant delivery device.

FIG. 4 shows an example detachable frame 46. As shown in FIG. 4, the frame 46 may include a body portion 56. In some examples, the body portion 56 may be understood to define a square, rectangular, circular, ovular, or similarly shaped framework from which other members may extend. For example, the body portion 56 of the frame 46 may bear some resemblance to an elongated rectangle having a proximal portion 42 and a distal portion 44. The body portion 56 may include a first elongated strut spaced apart from a second elongated strut. The body portion 56 may include one or more apertures 52 defined between the struts of the body portion 56. For example, the body portion 56 may include first and second apertures 52 having a stiffening member 62*a* extending transversely across the body portion between the first and second elongated struts to define the first and second apertures 52. For example, the transverse stiffening member 62*a* may be located between the first and second apertures 52. The body portion 56 may be positioned along a central portion of the implant 12 when attached thereto. Further, the frame 46 may include a head portion 58 extending away from the proximal portion 42. The head portion 58 may include one or more apertures 60.

As shown in FIG. 4, the detachable frame 46 may include one or more sets of proximal attachment arms 64*a* and distal attachment arms 64*c* extending away from body portion 56. It can be appreciated each of the attachment arms 64*a*/64*c*, as described herein, may be attached to the implant 12. Further, each respective attachment arm 64*a*/64*c* may include a first, proximal end 66 and a second, distal end 68. The first end 66 of each of the attachment arms 64*a*/64*c* may be a base end of the attachment arm 64*a*/64*c* rigidly attached to the body portion 56, while the opposite, second end 68 may be a free end of the attachment arm 64*a*/64*c* spaced away from the body portion 56. In some examples, (such as that shown in FIG. 4), the attachment arms 64*a*/64*c* and the head portion 58 may form a monolithic structure with body portion 56. In other words, in some examples the body portion 56, the head portion 58 and the attachment arms 64*a*/64*c* may be formed (e.g., machined, cut, shaped, stamped, printed, laser-cut, etc.) as a unitary structure from a single piece of material. In some instances, the detachable frame 46 may be a monolithic structure formed of a super-elastic metal material, such as nitinol. However, the above discussion is not intended to be limiting. Rather, it is contemplated that detachable frame 46 may be constructed using alternative materials and/or manufacturing methodologies. For example, the frame 46, or portions thereof, may be constructed from a polymeric material, a ceramic material and/or other various materials. Additionally, the frame 46 may be manufactured via an injection molding or alternative polymer manufacturing methodologies. Alternatively, the frame 46 may be formed through a 3-D printing process, if desired. Further, different portions of the frame 46 (as described above, for example), may be made from a variety of materials and combined using alternative methodologies. For example, the attachment arms 64*a*/64*c* may be made from a polymer material and combined with a central frame member constructed from a metal material. Variations of combining different materials with different portions of the frame 46 are contemplated.

FIG. 4 further illustrates that the attachment arms 64*a*/64*c* may include a variety of shapes. For example, in some instances, the attachment arms 64*a*/64*c* may include a bow and/or general curvilinear shape.

Additionally, FIG. 4 illustrates that the detachable frame 46 may include one or more sets of connector legs 64*b*. Each respective connector leg 64*b* may include a first, proximal end 70 and a second, distal end 72. The first end 70 of each of the connector leg 64*b* may be a base end of the connector leg 64*b* rigidly attached to the body portion 56, while the opposite, second end 72 may be a free end of the connector leg 64*b* spaced away from the body portion 56. Further, as will be described in greater detail below, the one or more sets of connector legs 64*b*, in combination with the head portion 58, may attach the detachable frame 46 to a portion of the delivery system. Additionally, the connector legs 64*b* may include one or more features which assist in attaching the frame 46 to the delivery system 40. For example, FIG. 4 illustrates that the connector legs 64*b* may include an annular portion 54 positioned adjacent the distal ends 72 of each of the connector legs 64*b*. In some examples, the annular portion 54 may include an aperture positioned in a central region of the annular portion 54. As will be described above, the annular portion 54 of each of the connector legs 64*b* may be utilized to attach to a portion of the delivery system 40.

In some examples, the frame 46 may include a variety of shapes and/or geometric arrangements. For example, the frame 46 may include one or more stiffening members 62*a*/62*b*/62*c* extending throughout the frame 46. Further, the stiffening members 62*a*/62*b*/62*c* may be arranged within the frame 46 (e.g., within the body portion 56) such that they create the one or more apertures 52. The number, shape, configuration and/or arrangement of the stiffening members 62*a*/62*b*/62*c* and/or apertures 52 may depend on the particular performance characteristics desired to be imparted to the detachable frame 46. For example, additional stiffening members 62*a*/62*b*/62*c* may be added to frame 46 to provide increased stiffness to frame 46. In other instances, stiffening members 62*a*/62*b*/62*c* may take on particular geometries that increase the stiffness or flexibility in a particular direction while decreasing stiffness or flexibility in a different direction, for example.

The stiffening members 62*a*/62*b*/62*c* may be located (e.g., arranged) throughout the frame 46 in a variety of configurations to provide additional stiffness and/or structural integrity to a particular frame shape. In other words, a wide variety of different shapes and/or arrangements of the stiffening members 62*a*/62*b*/62*c* may be included within the frame 46 in order to impart customized performance characteristics of the frame 46. For example, in some instances, it may be desirable to transfer rotational forces placed on the head portion 58 to one or more of the attachment arms 64*c* positioned at the distal portion of the frame 46. The addition of stiffening members 62*a*/62*b*/62*c* may permit transfer of those rotational forces throughout frame 46 (e.g., to the distal portion of frame 46) while minimizing the amount of force lost and/or dissipated throughout the frame 46 due to undesirable flexing of the frame members.

For example, FIG. 4 illustrates that the frame 46 may include a first support strut 65*a* (e.g., support beam, support member, stiffening strut, etc.) positioned adjacent to a second support strut 65*b*. Further, the first support strut 65*a* may converge with the second support strut 65*b* at the base of the distal attachment arm 64*c*. It can be further appreciated that the distal attachment arm 64*c* may extend away from the convergence point of the first support strut 65*a* and the second support strut 65*b* to a free end of the distal attachment arm 64*c*. Similarly, FIG. 4 illustrates that the frame 46 may include a third support strut 67*a* positioned adjacent to a fourth support strut 67*b*. Further, the third support strut 67*a* may converge with the fourth support strut 67*b* at the base of the distal attachment arm 64*c*. It can be further appreciated that the distal attachment arm 64*c* may extend away from the convergence point of the first support strut 67*a* and the second support strut 67*b* to a free end of the distal attachment arm 64*c*. Additionally, it can be appreciated that the second support strut 65*b* may converge with the fourth support strut 67*b* to form the stiffening member 62*c*. It can be appreciated that the combination of the first support strut 65*a*, the second support strut 65*b*, the third support strut 67*a* and the fourth support strut 67*b* may, collectively, increase the stiffness in the distal portion 44 of the body portion 56 of the frame 46. This increased stiffness may improve the ability of a clinician to control the movement of the frame 46 (when adjacent the target site) from a position outside the body (e.g., as when a clinician is maneuvering the handle from outside a patient's body).

As discussed above with respect to FIG. 3, FIG. 4 further illustrates that the frame 46 may include one or more attachment apertures 50 located along a distal portion 68 of the one or more attachment arms 64*a*/64*c*. For example, FIG. 4 shows the attachment apertures 50 positioned at a distal end 68 of the attachment arms 64*a*/64*c*. As will be discussed in greater detail below, the attachment apertures 50 may be utilized to attach the frame 46 to an example implant 12.

While FIG. 4 shows three attachment apertures 50 positioned along a distal portion 68 of each of the attachment arms 64*a*/64*c*, the illustrated number of the attachment apertures 50 is not intended to be limiting. In other embodiments, the attachment apertures 50 may be located along another region of the attachment arms 64*a*/64*c*, such as a proximal portion of the attachment arms 64*a*/64*c* proximate the body portion 56. In other words, it is contemplated that one or more attachment arm apertures 50 may be positioned along any portion of the frame 46. The number of attachment apertures 50 positioned along the frame 46 may be 1, 2, 3, 4, 5, 6, 7, 8, 9, 10, 15, 20 or more. In other instances, the attachment arms 64*a*/64*b*/64*c* may be devoid of attachment apertures. In such instances, the attachment arms 64*a*/64*c* may include an alternative attachment structure for attaching to the implant 12.

FIG. 5 shows the frame 46 coupled to various components of the example implant delivery system 40 (e.g., the implant delivery system 40 shown above with respect to FIG. 2). As shown in FIG. 2, FIG. 5 illustrates the inner shaft 36 extending through the lumen of the delivery sheath 34.

Further, FIG. 5 shows the inner shaft 36 may be coupled to the frame 46 via a connection assembly 74. The connection assembly 74 may include a first connection member 76 (e.g., collar) and a tack disk 80 coupled to the frame 46. Specifically, FIG. 5 illustrates that the collar 76 and the tack disk 80 may be coupled to both the head portion 58 and the two connector legs 64*b* of the frame 46. As shown in FIG. 5, the head portion 58 and the two connector legs 64*b* may be "sandwiched" between the collar 76 and the tack disk 80. In other words, the head portion 58 and the two connector legs 64*b* of the frame 46 may be constrained between the collar 76 and the tack disk 80 with a proximal portion of the tack disk 80 assembled through the aperture 60 (shown in FIG. 4) of the head portion 58 and the apertures in the annular portions 54 (shown in FIG. 4) of the connector legs 64*b*. The first collar 76 and tack disk 80 connection will be discussed in greater detail below.

FIG. 5 further illustrates that the connection assembly 74 may further include a second connection member 78 located at the distal end region 38 of inner shaft 36. It is noted that the connection member 78 shown in FIG. 5 is a simplified illustration (in both scale and shape) of the second connection member 78. As will be discussed below, the second connection member 78 may include a geometric shape which is designed to mate with and engage with the geometric shape of the collar 76. Both the second connection member 78 and the collar 76 may include a variety of geometric shapes.

While FIG. 5 does not show the collar 76 attached directly to the second connection member 78, it can be appreciated that the collar 76 and the second connection member 78 of the connection assembly 74 may form a mating connection. For example, in some instances, the collar 76 may form a male connection member while the second connection member 78 may form a mating female connection member matingly engageable with the collar 76 and disengageable therefrom. In other words, in some examples, the second connection member 78 may include a cavity which is configured to extend over/around and allow the collar 76 to be inserted therein. In other instances, the collar 76 may be a female connection member, while second connection member 78 may be a mating male connection member, if desired.

Additionally, as shown in FIG. 5, it is contemplated that the second connection member 78 may disengage or decouple from the collar 76. For example, in some instances the connection assembly 74 (including the collar 76 and the second connection member 78) may be defined as a "quick release" connection assembly, or otherwise decoupling connection assembly. It is further contemplated that a variety of design configurations may be employed to engage/disengage (i.e., couple/decouple) the collar 76 and the second connection member 78 from one another. For example, the collar 76 and the second connection member 78 may be coupled via a threaded connection, friction fit, spring loaded connection, bayonet connection, movable collar or other actuation mechanism, or the like. Further, the collar 76 and the second connection member 78 may be engaged/disengaged by an operator of the device.

It can be appreciated from the above discussion that the inner shaft 36 may be attached (via the collar 76, the second connection member 78 and the tack disk 80) to the head portion 58 and/or the two connector legs 64*b* of the frame 46. It can be further appreciated that the collar 76 and the tack disk 80 of the connection assembly 74 may attach to the head portion 58 via an aperture 60 (shown in FIG. 4) and attach the connector legs 64*b* via apertures in the annular portions 72.

FIG. 5 further illustrates that the implant delivery system 40 described herein may include a tack member 84 designed to "anchor" the delivery system 40 in place prior to a clinician affixing the implant 12 to the bone and/or tendon. For example, FIG. 5 illustrates the tack member 84 extending distally from the tack disk 80. As shown in FIG. 5, the tack member 84 may extend distally from the tack disk 80 and be substantially perpendicular to the implant 12 (not shown in FIG. 5) and/or frame 46. In some instances, the tack member 84 may extend generally parallel to the longitudinal axis of the outer shaft 32 and/or the inner shaft 36 with the frame 46 and implant 12 extending generally perpendicular to the longitudinal axis of outer shaft 32 and/or the inner shaft 36. However, this configuration is not intended to be limiting. Rather, it is contemplated that the tack member 84 may extend distally from the tack disk 80 and/or the frame 46 at an oblique angle to the longitudinal axis of the outer shaft 32, the inner shaft 36, and/or the frame 46, if desired.

Figure 9:
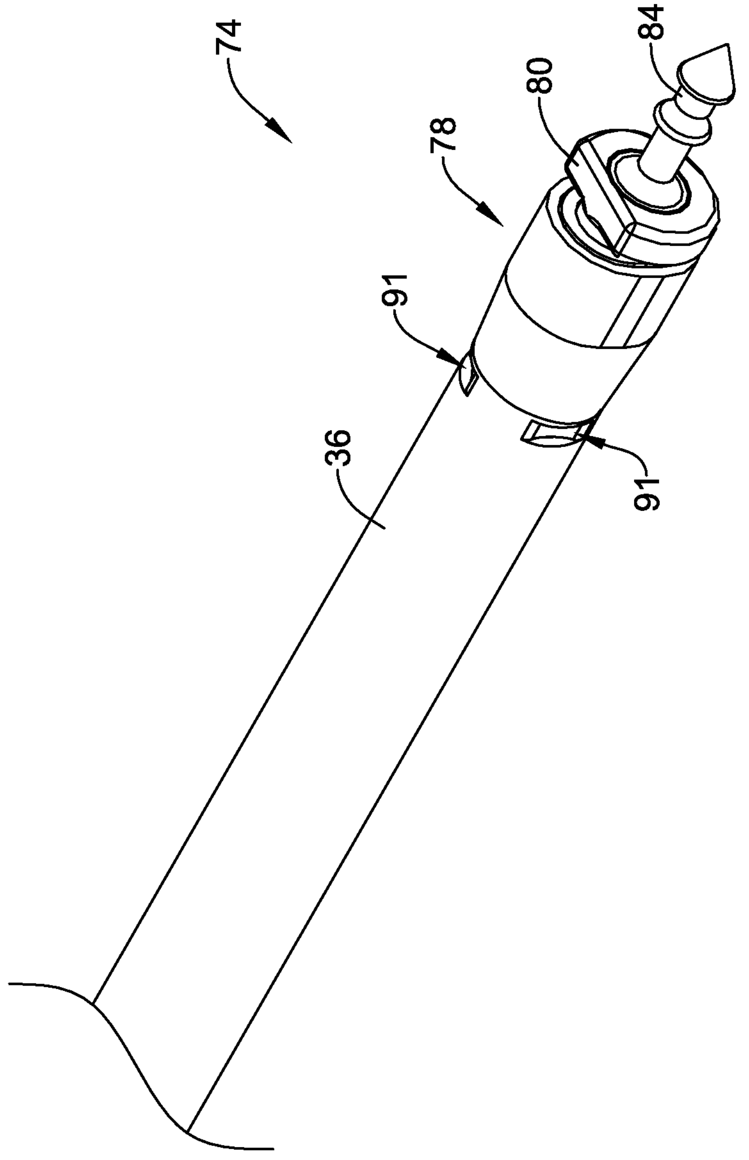
FIG. 9 illustrates a portion of an example implant delivery device.
Figure 10:
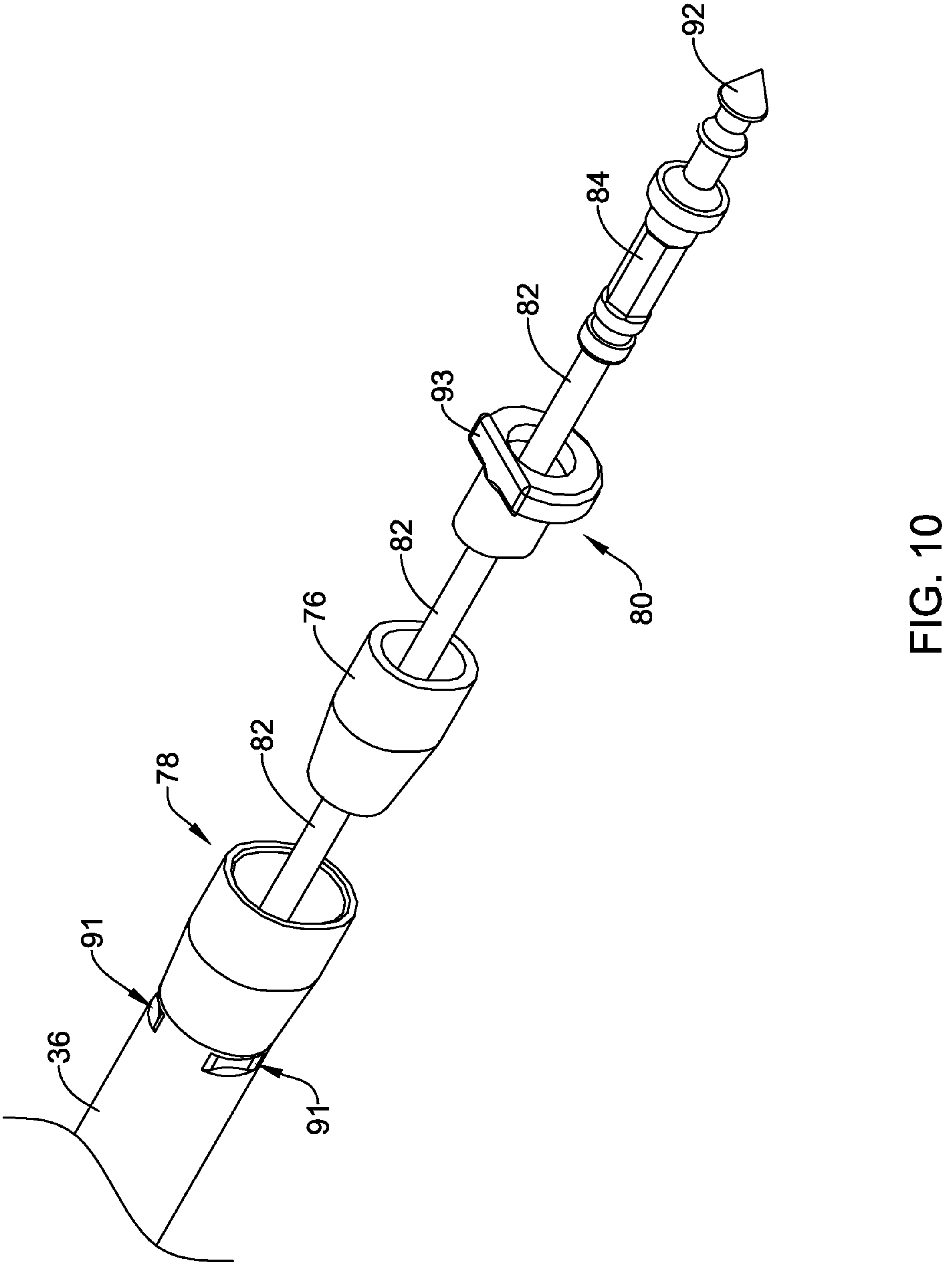
FIG. 10 is an exploded view of the implant delivery device shown in FIG. 9.
Figure 11:
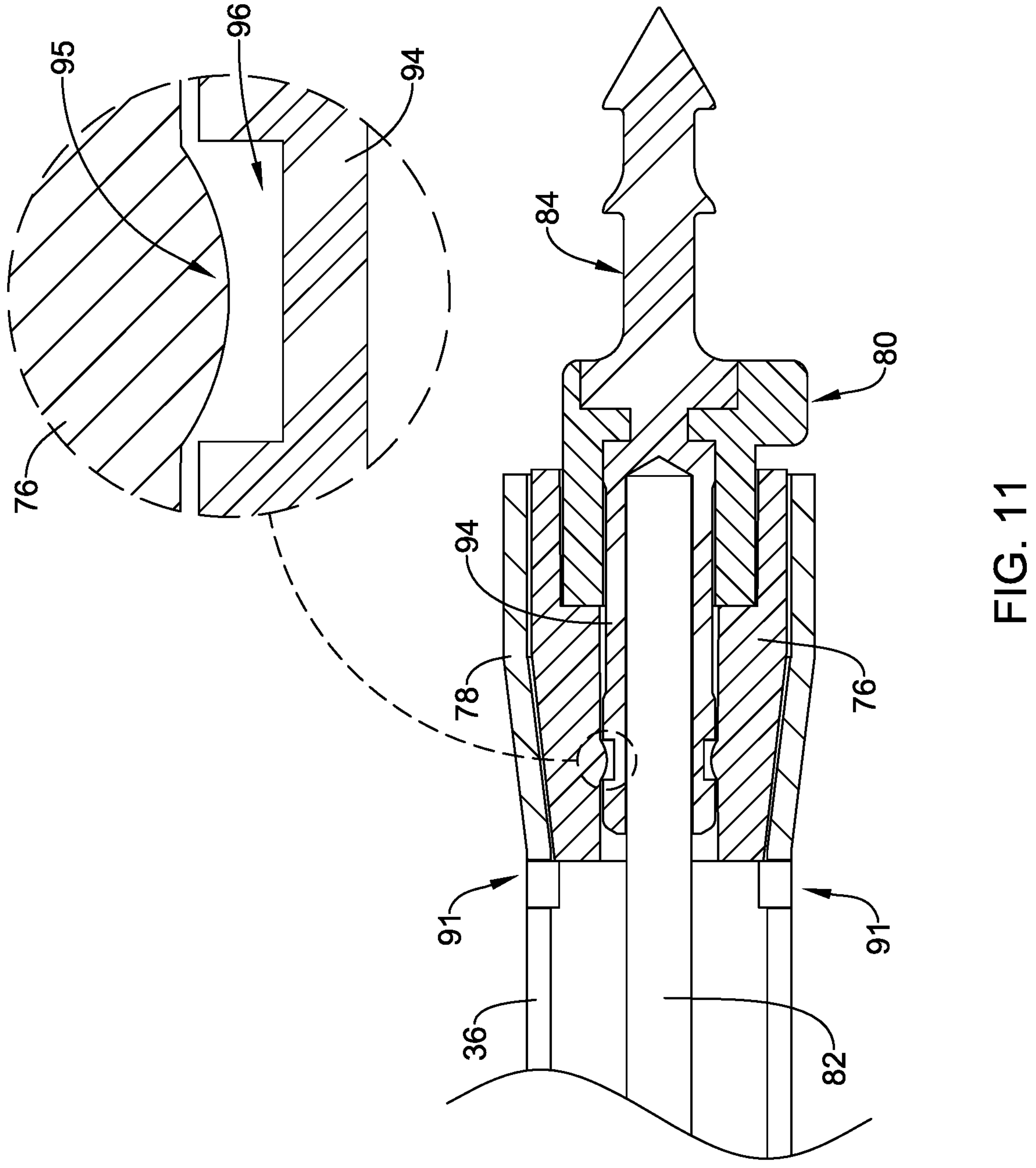
FIG. 11 is cross-section of a portion of the implant delivery device shown in FIG. 10.

In some instances, the tack member 84 may resemble a cylindrical pin or rod extending away from the frame 46 (the tack member 84 is shown in greater detail below with respect to FIGS. 9-11). Additionally, the tack member 84 may be designed to be rigid enough to be pounded and/or inserted into bone. For example, in some instances, a clinician may apply a force to a proximal portion of the implant delivery system 40 (e.g., inner shaft 36) such that the tack member 84 may be "hammered" into a body structure (e.g., bone). As shown in FIG. 5, the tack member 84 may include a tapered distal tip, which may be a sharpened or blunt tapered distal tip in some instances. Additional features of the tack member 84 are shown in FIGS. 9-11.

In some instances, the tack member 84 may be stationary (e.g., fixed in place) relative to the frame 46, the collar 76 and/or the tack disk 80 of the connection assembly 74. For example, the tack member 84 may extend distally from the tack disk 80 and away from the surface of the frame 46 which faces a target site.

The tack member 84 may extend through one of the apertures 52 defined in the body portion 56 when the frame 46 is in the deployed configuration of FIG. 5. The aperture 52 may be sized such that the distal tip of the tack member 84 may be prevented from passing proximally out through the aperture 52 when the frame 46 is flexed relative to the inner shaft 36, thus maintaining the distal tip of the tack member 84 on a distal side of the frame 46 for engagement with a bone during implantation of the implant 12. Furthermore, although not shown, the tack member 84 may extend through the implant 12 when attached to the frame 46 in the deployed configuration.

As discussed above, FIG. 5 illustrates that the frame 46 may include a coil attachment member 49 coupled to the distal end 68 of the two proximal attachment arms 64*a* and the two distal attachment arms 64*c*. Referring back to FIGS. 3-4, it can be appreciated that the coil attachment members 49 may be utilized to attach the frame 46 to the implant 12. It can be further appreciated that the coil attachment members 49 may be threaded through one or more of the attachment apertures 50 located on the distal end region 68 of the two proximal attachment arms 64*a* and the two distal attachment arms 64*c*.

Additionally, FIG. 5 further illustrates that the frame 46 may further include several attachment sleeves 86 (e.g., mittens) disposed along the distal end 68 of each of the attachment arms 64*a*/64*c*. Specifically, it can be appreciated from FIG. 5 that each of the attachment arms 64*a*/64*c* may include an attachment sleeve 86 which is positioned overtop a base portion of the coil attachment members 49 after the coil attachment members 49 are threaded through the attachment apertures 50, thereby securing the coil attachment members 49 to the frame 46.

As discussed above, it can be appreciated that the coil attachment members 49 may be utilized to attach the implant 12 to the frame 46. For example, each of the coil attachment members 49 may be inserted through the implant 12 whereby the coiled portion of each of the coil attachment members 49 may secure the implant 12 to the frame 46. In other words, after being inserted through the implant 12, the implant 12 may be positioned between the underside of the frame 12 and the coiled portion of each of the coil attachment members 49. The coil attachment members 49 may be a length of wire including a coiled portion, with a base portion of the wire secured to the frame 12 with the attachment sleeve 86.

Figure 6:
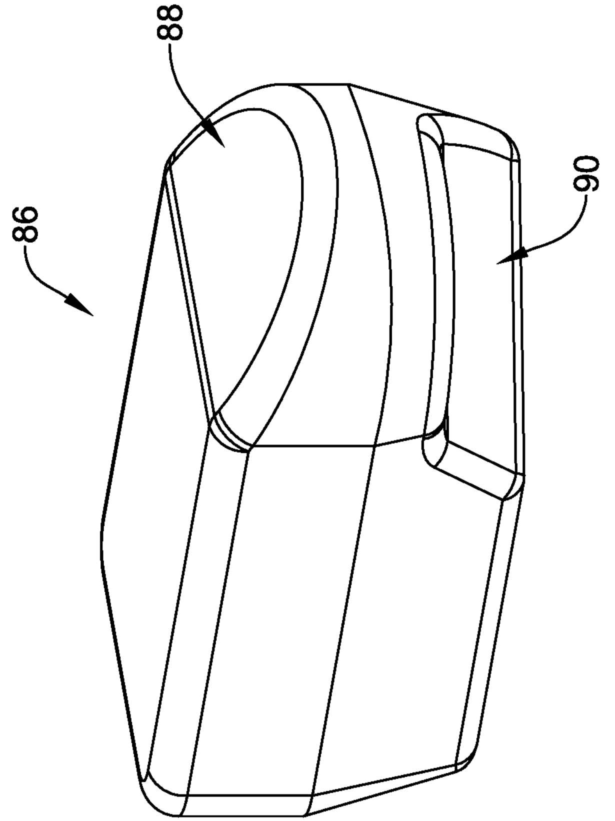
FIG. 6 illustrates a portion of the implant delivery device shown in FIG. 5.

FIG. 6 illustrates an example attachment sleeve 86. In some instances, the attachment sleeve 86 may be referred to as a mitten. As discussed above, the attachment sleeve 86 may be positioned overtop the base portion of the coil attachment members 49 after the coil attachment members 49 are threaded through the attachment apertures 50, thereby securing the coil attachment members 49 to the frame 46. In some examples, the attachment sleeve 86 may be overmolded onto the frame and attachment members 49, thereby fixedly securing the attachment members 49 to the frame 46. In other examples, the attachment sleeve 86 may be designed to be slid onto the frame 46 and attachment members 49, whereby the attachment sleeve 86 is fixedly attached to the frame 46 via a UV adhesive (or other similar glue or adhesive). It can be appreciated that when the attachment sleeve 86 is either overmolded or UV glued onto the frame 46 and the attachment members 49, the sleeve 86 may be configured to be permanently fixed to the frame 46. It can be appreciated that other attachment methodologies may be utilized to fixedly attach the attachment sleeve 86 to the frame 46. For example, the attachment sleeve 86 may be attached to the frame 46 utilizing press fitting, heat staking, crimping, or other similar methodologies.

FIG. 6 further illustrates that the attachment sleeve 86 may include a tapered portion 88 extending downward from a top surface of the attachment sleeve 86. Additionally, FIG. 6 shows that the attachment sleeve 86 may include a recessed cutout region 90.

Figure 7:
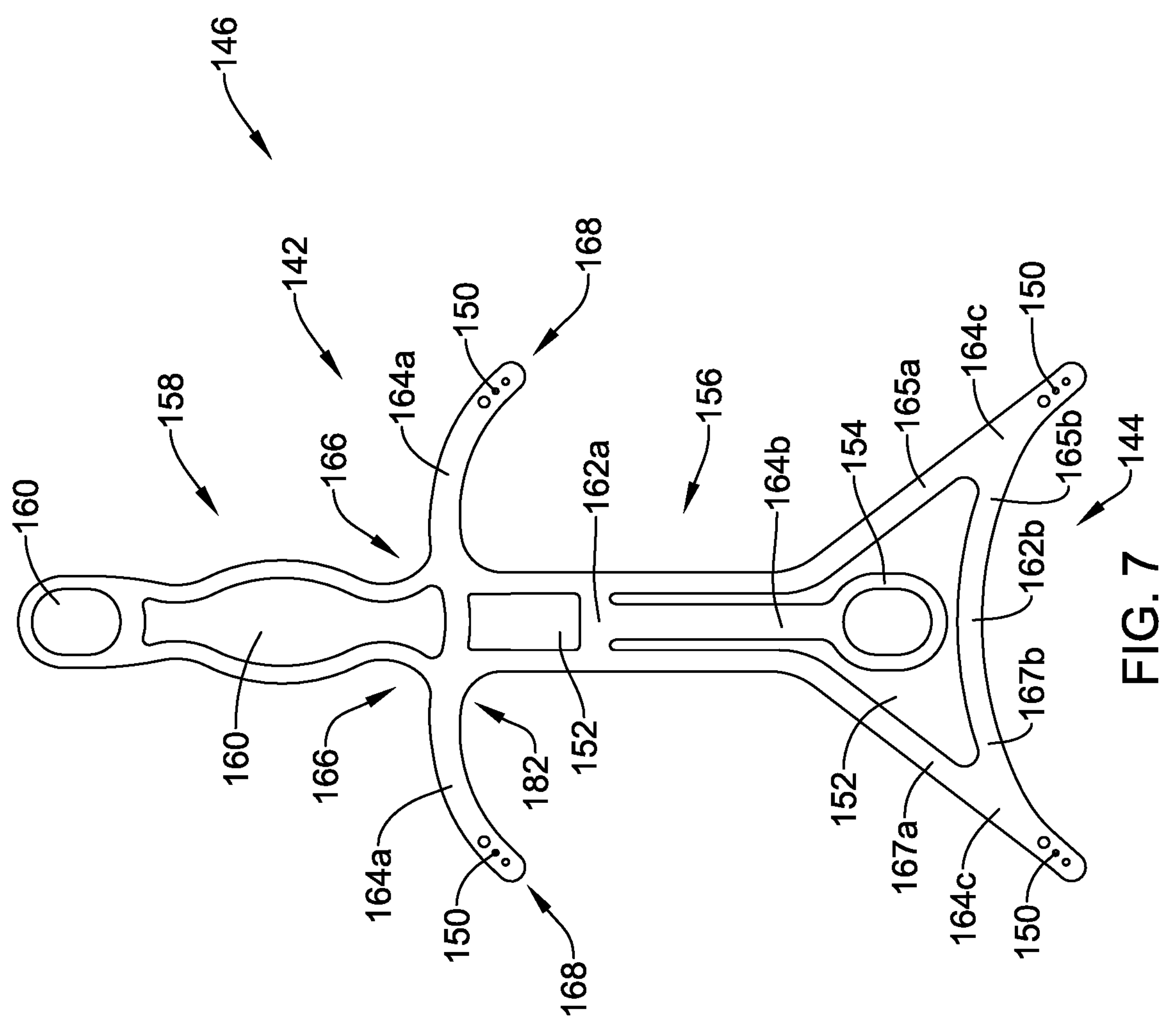
FIG. 7 illustrates another example implant delivery device.

FIG. 7 shows another example detachable frame 146. As shown in FIG. 7, the frame 146 may include a body portion 156. In some examples, the body portion 156 may be understood to define a square, rectangular, circular, ovular, or similarly shaped framework from which other members may extend. For example, the body portion 156 of the frame 146 may bear some resemblance to an elongated rectangle having a proximal portion 142 and a distal portion 144. The body portion 156 may include a first elongated strut spaced apart from a second elongated strut. The body portion 156 may include one or more apertures 152 defined between the struts of the body portion 156. For example, the body portion 156 may include first and second apertures 152 having a stiffening member 162*a* extending transversely across the body portion between the first and second elongated struts to define the first and second apertures 152. For example, the transverse stiffening member 162*a* may be located between the first and second apertures 152. The body portion 156 may be positioned along a central portion of the implant 12 when attached thereto. Further, the frame 146 may include a head portion 158 extending away from the proximal portion 142. The head portion 158 may include one or more apertures 160.

As shown in FIG. 7, the detachable frame 146 may include one or more sets of proximal attachment arms 164*a* and distal attachment arms 164*c* extending away from body portion 156. It can be appreciated each of the attachment arms 164*a*/164*c*, as described herein, may be attached to the implant 12. Further, each respective attachment arm 164*a*/164*c* may include a first, proximal end 166 and a second, distal end 168. The first end 166 of each of the attachment arms 164*a*/164*c* may be a base end of the attachment arm 164*a*/164*c* rigidly attached to the body portion 156, while the opposite, second end 168 may be a free end of the attachment arm 164*a*/164*c* spaced away from the body portion 156. In some examples, (such as that shown in FIG. 7), the attachment arms 164*a*/164*c* and the head portion 158 may form a monolithic structure with body portion 156. In other words, in some examples the body portion 156, the head portion 158 and the attachment arms 164*a*/164*c* may be formed (e.g., machined, cut, shaped, stamped, printed, laser-cut, etc.) as a unitary structure from a single piece of material. In some instances, the detachable frame 146 may be a monolithic structure formed of a superelastic metal material, such as nitinol. However, the above discussion is not intended to be limiting. Rather, it is contemplated that detachable frame 146 may be constructed using alternative materials and/or manufacturing methodologies. For example, the frame 146, or portions thereof, may be constructed from a polymeric material, a ceramic material and/or other various materials. Additionally, the frame 146 may be manufactured via an injection molding or alternative polymer manufacturing methodologies. Alternatively, the frame 146 may be formed through a 3-D printing process, if desired. Further, different portions of the frame 146 (as described above, for example), may be made from a variety of materials and combined using alternative methodologies. For example, the attachment arms 164*a*/164*c* may be made from a polymer material and combined with a central frame member constructed from a metal material. Variations of combining different materials with different portions of the frame 146 are contemplated.

FIG. 7 further illustrates that the attachment arms 164*a*/164*c* may include a variety of shapes. For example, in some instances, the attachment arms 164*a*/164*c* may include a bow and/or general curvilinear shape.

Additionally, FIG. 7 illustrates that the detachable frame 146 may include a connector leg 164*b*. The connector leg 164*b* may include a first end attached to the stiffening member 162*a*, while the opposite, second end of the connector leg 164*b* may be a free end. Further, as will be described in greater detail below, the connector leg 164*b*, in combination with the head portion 158, may attach the detachable frame 146 to a portion of the delivery system. Additionally, the connector leg 164*b* may include one or more features which assist in attaching the frame 146 to the delivery system 40. For example, FIG. 7 illustrates that the connector leg 164*b* may include an annular portion 154. In some examples, the annular portion 154 may include an aperture positioned in a central region of the annular portion 154. As will be described above, the annular portion 154 of the connector leg 164*b* may be utilized to attach to a portion of the delivery system 40.

In some examples, the frame 146 may include a variety of shapes and/or geometric arrangements. For example, the frame 146 may include one or more stiffening members 162*a*/162*b* extending throughout the frame 146. Further, the stiffening members 162*a*/162*b* may be arranged within the frame 146 (e.g., within the body portion 156) such that they create the one or more apertures 152. The number, shape, configuration and/or arrangement of the stiffening members 162*a*/162*b* and/or apertures 152 may depend on the particular performance characteristics desired to be imparted to the detachable frame 146. For example, additional stiffening members 162*a*/162*b* may be added to frame 146 to provide increased stiffness to frame 146. In other instances, stiffening members 162*a*/162*b* may take on particular geometries that increase the stiffness or flexibility in a particular direction while decreasing stiffness or flexibility in a different direction, for example.

The stiffening members 162*a*/162*b* may be located (e.g., arranged) throughout the frame 146 in a variety of configurations to provide additional stiffness and/or structural integrity to a particular frame shape. In other words, a wide variety of different shapes and/or arrangements of the stiffening members 162*a*/162*b* may be included within the frame 146 in order to impart customized performance characteristics of the frame 146. For example, in some instances, it may be desirable to transfer rotational forces placed on the head portion 158 to one or more of the attachment arms 164*c* positioned at the distal portion of the frame 146. The addition of stiffening members 162*a*/162*b* may permit transfer of those rotational forces throughout frame 146 (e.g., to the distal portion of frame 146) while minimizing the amount of force lost and/or dissipated throughout the frame 146 due to undesirable flexing of the frame members.

For example, FIG. 7 illustrates that the frame 146 may include a first support strut 165*a* (e.g., support beam, support member, stiffening strut, etc.) positioned adjacent to a second support strut 165*b*. Further, the first support strut 165*a* may converge with the second support strut 165*b* at the base of the attachment arm 164*c*. It can be further appreciated that the attachment arm 164*c* may extend away from the convergence point of the first support strut 165*a* and the second support strut 165*b* to a free end of the attachment arm 164*c*. Similarly, FIG. 7 illustrates that the frame 146 may include a third support strut 167*a* positioned adjacent to a fourth support strut 167*b*. Further, the third support strut 167*a* may converge with the fourth support strut 167*b* at the base of the attachment arm 164*c*. It can be further appreciated that the attachment arm 164*c* may extend away from the convergence point of the first support strut 167*a* and the second support strut 167*b* to a free end of the attachment arm 164*c*. Additionally, it can be appreciated that the second support strut 165*b* may converge with the fourth support strut 167*b* to form the stiffening member 162*b*. It can be appreciated that the combination of the first support strut 165*a*, the second support strut 165*b*, the third support strut 167*a* and the fourth support strut 167*b* may, collectively, increase the stiffness in the distal portion 144 of the body portion 156 of the frame 146. This increased stiffness may improve the ability of a clinician to control the movement of the frame 146 (when adjacent the target site) from a position outside the body (e.g., as when a clinician is maneuvering the handle from outside a patient's body).

FIG. 7 further illustrates that the frame 146 may include one or more attachment apertures 150 located along a distal portion 168 of the one or more attachment arms 164*a*/164*c*. For example, FIG. 7 shows the attachment apertures 150 positioned at a distal end 68 of the attachment arms 164*a*/164*c*. As will be discussed in greater detail below, the attachment apertures 150 may be utilized to attach the frame 146 to an example implant 12.

While FIG. 7 shows three attachment apertures 150 positioned along a distal portion 168 of each of the attachment arms 164*a*/164*c*, the illustrated number of the attachment apertures 150 is not intended to be limiting. In other embodiments, the attachment apertures 150 may be located along another region of the attachment arms 164*a*/164*c*, such as a proximal portion of the attachment arms 164*a*/164*c* proximate the body portion 156. In other words, it is contemplated that one or more attachment arm apertures 150 may be positioned along any portion of the frame 146. The number of attachment apertures 150 positioned along the frame 146 may be 1, 2, 3, 4, 5, 6, 7, 8, 9, 10, 15, 20 or more. In other instances, the attachment arms 164*a*/164*c* may be devoid of attachment apertures. In such instances, the attachment arms 164*a*/164*c* may include an alternative attachment structure for attaching to the implant 12.

Figure 8:
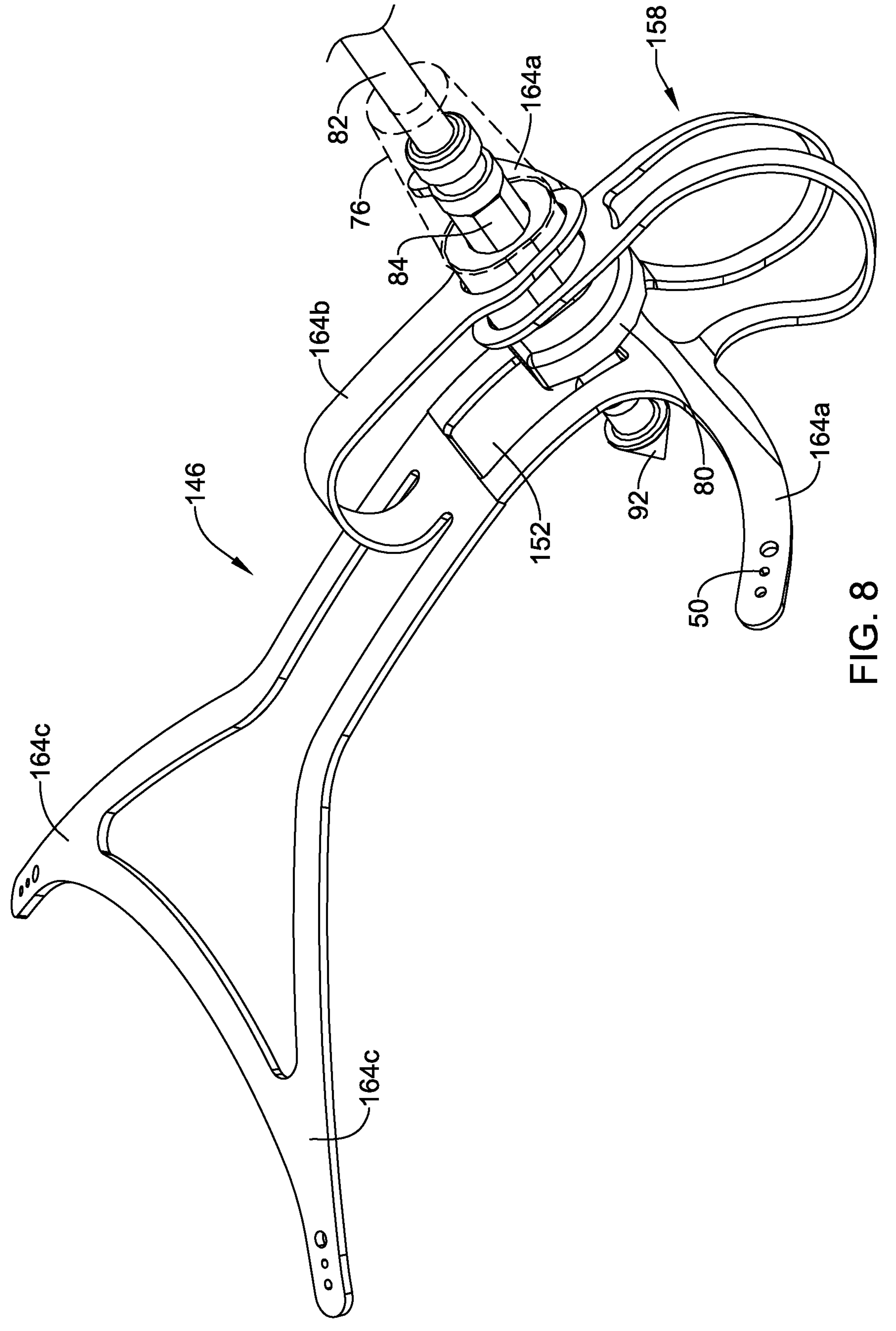
FIG. 8 illustrates the implant delivery device of FIG. 7 attached to an example implant delivery system.

Similar to FIG. 5 (which illustrates that frame 46 attached to various components of the example implant delivery system 40), FIG. 8 shows the frame 146 coupled to various components of the example implant delivery system 40 (e.g., the implant delivery system 40 shown above with respect to FIG. 2). It is noted that, for simplicity, the delivery sheath 34 and the inner shaft 36 have been omitted from FIG. 8. However, it can be appreciated that delivery system shown in FIG. 8 may include the inner shaft 36 (having a lumen through which the tether 82 may extend) and the delivery sheath 34 (within which the combination frame 146 and implant 12 may be nested as the delivery system is advanced to a target site). The inner shaft 36 and delivery sheath 34, which may be utilized with the various delivery system components illustrated and described in FIG. 8, may be similar in form and function with the inner shaft 36 and delivery sheath 34 illustrated and described with respect to FIG. 5. It is noted that the system shown in FIG. 8 may be similar in form and function to the system shown in FIG. 5 aside from the particular geometric shaped of the frame 146 (as compared to the frame 46 shown in FIG. 5).

FIG. 8 shows the tether 82 may be coupled to the frame 146 via the tack disk 80 (which is coupled to the tack member 84 as described above). As described above with respect to FIG. 5, the frame 146 may be coupled to the delivery system 40 via a connection assembly which may include a collar 76 and the tack disk 80. For clarity, the outline of the collar 76 is depicted with dotted lines. As discussed above with respect to FIG. 5, FIG. 8 illustrates that the tack disk 80 may be coupled to both the head portion 58 and the two connector legs 64*b* of the frame 46. In particular, as described above with respect to FIG. 5, the head portion 158 and the connector leg 164*b* may be "sandwiched" between a distal facing surface or rim of the collar 76 and a proximal facing surface or rim of the tack disk 80. In other words, the head portion 158 and the connector leg 164*b* of the frame 46 may be constrained between the collar 76 and the tack disk 80.

FIG. 9 illustrates a portion of the connection assembly 74 described above. Specifically, FIG. 9 illustrates the tack disk 80 and the tack member 84 coupled to the inner shaft 36 (the collar 76, which is part of the connection assembly 74, cannot be visualized in FIG. 9 as it is nested within the second connection member 78 of the inner shaft 36). In other words, FIG. 9 illustrates that the collar 76 may be coupled to the tack disk 80, which is in turn coupled to the tack member 84. As discussed above, the collar 76 may be designed to nest within the distal end of the inner shaft 36 (e.g., nest within the aperture or bore of the second connection member 78).

Figure 12:
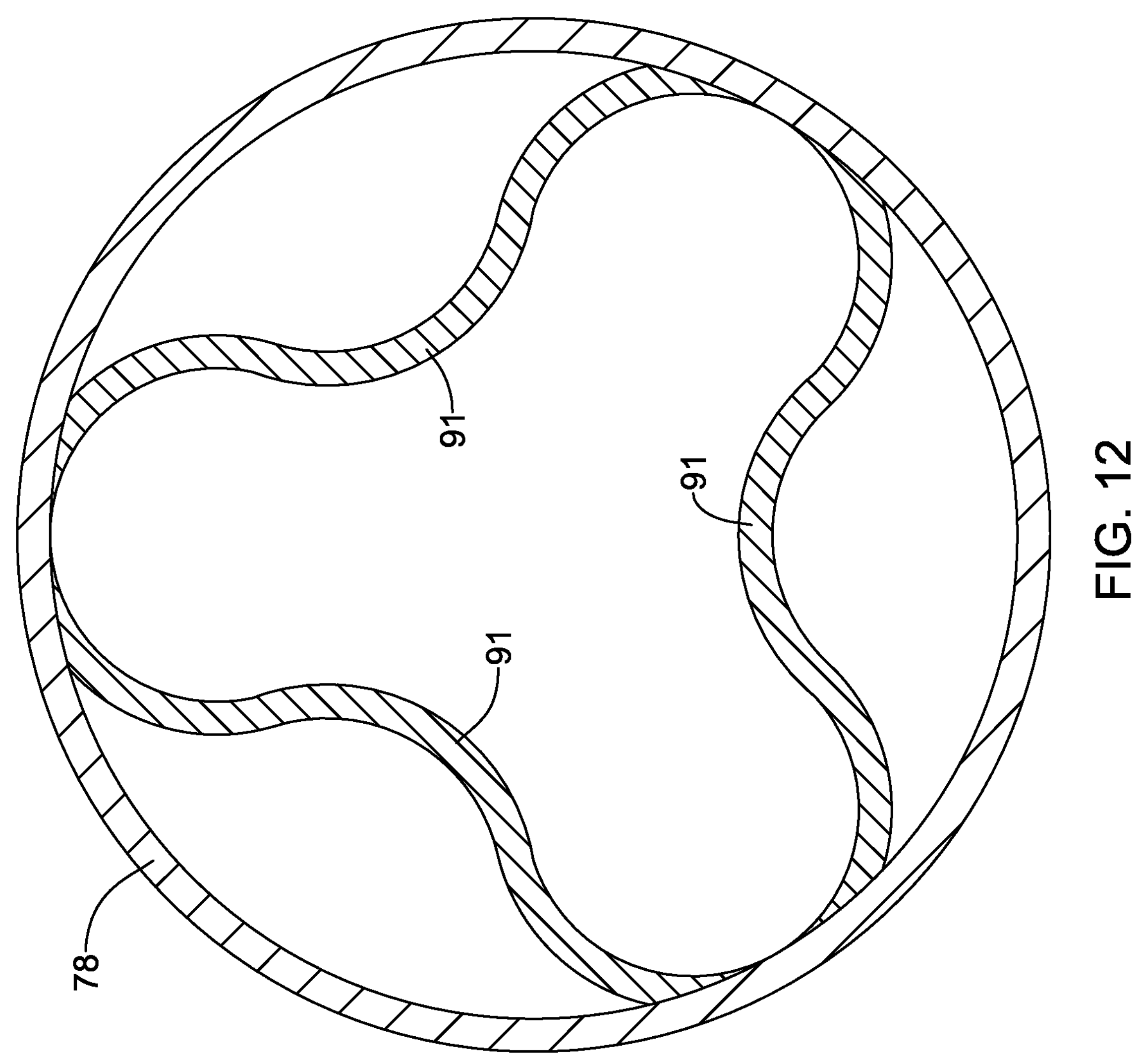
FIG. 12 is an end view of a component of the example implant delivery device shown in FIG. 11.

As will be described in greater detail below, FIG. 9 further illustrates that the inner shaft 36 may include one or more indentations which may be formed by punching the wall of the inner shaft 36 radially inward. A cross-sectional view of the indentations 91 is shown in FIG. 12. In other words, the indentations 91 may be formed by pushing a portion of the wall of the inner shaft 36 inward, toward the longitudinal axis of the inner shaft 36. As will be discussed below, the portion of the wall of the inner shaft 36 which extends radially inward to form the indentations 91 may create a positive stop which limits the extent to which the collar 76 may extend into the second connection member 78 of the inner shaft 36. In some examples, the indentations 91 may be formed via a stamping process. For example, the inner shaft 36 may be formed from a flat sheet which is cut and stamped to include the indentations 91. After punching out the indentations 91, the flat sheet may be rolled and welded in the oval shape of the inner shaft 36.

FIG. 10 illustrates an exploded view of the connection assembly 74 shown in FIG. 9. In particular, FIG. 10 illustrates the tack member 84 attached to the tether 82. The tether 82 may extend through an aperture in the tack disk 80, through another aperture in the collar 76 and extend through the lumen of the inner shaft 36. While not shown in FIG. 10, it can be appreciated that the tether 82 may extend through the lumen of the inner shaft 36 and terminate at a location (e.g., a handle member) where a clinician may be able to manipulate the tether 82 to release the frame 46 from the implant 12.

FIG. 10 further illustrates that the tack member 84 may include one or more features designed to improve its ability to penetrate the target site (e.g., bone) and remain anchored within the target site. For example, FIG. 10 illustrates the distal end of the tack member 84 may include a pointed (e.g., tapered, cone-shaped) tip 92.

Additionally, as will be discussed in greater detail below, the proximal end region of the tack member 84 may be crimped onto a distal end portion of the tether 82, thereby fixedly attaching the tack member 84 to the tether 82. It can be appreciated that the proximal end portion of the tack member 84 may initially be rounded prior to being crimped onto the tether 82, whereby the crimping process (which attaches the tack member 84 to the tether 82) may reshape the proximal portion of the tack member 84 to include one or more flat surfaces (such as the flat surfaces which form the hexagonal shape shown in FIG. 10).

Additionally, in some examples the tack disk 80 may be attached to a portion of the tack member 84. For example, the tack disk 80 may be over-molded onto a portion of the tack member 84, thereby fixedly attaching the tack disk 80 to the tack member 84. The alignment of the tack disk 80 with the tack member 84 will be illustrated and discussed further with respect to FIG. 11. Further, FIG. 10 further illustrates the tack disk 80 may include a flat portion 93 which is designed to serve as the backstop when the tack member 94 is malleted into bone. Further yet, the proximal end of the tack disk 80 may include a shaped (e.g., an oval shape) which is designed to mate with both the apertures in the annular portions 54/154 (shown in FIG. 4 and FIG. 7) and apertures 60/160 (shown in FIG. 4 and FIG. 7) of the frames 46/146 in addition to the inner profile of the lumen of the collar 76.

In other examples, the tack member 84 may be machined as a single component which would resemble the combination of the tack disk 80 and the tack member 84 after they are attached together via the over-molding process described above. For example, the tack disk 80 and the tack member

84 may be designed as a single monolithic component which includes the features of both the tack disk 80 and the tack member 84 (accordingly, if the tack member 84 was machined to include both the features of the tack member 84 and tack disk 80, the tack disk 80 would be obsolete and would not be shown in FIG. 10).

After attaching the tack disk 80 to the tack member 84 (e.g., via an over-molding process as described above), the tack member 84 may be attached to the collar 76. As will be described in greater detail below, a proximal portion of the tack member 84 may extend through an aperture (e.g., lumen) in the tack disk 80 and may snap into an inner surface feature of the collar 76, thereby fixedly attaching the tack member 84 to the collar 76. The alignment of the collar 76, the tack disk 80, and the tack member 84 is illustrated and discussed further with respect to FIG. 11. As discussed above (e.g., with respect to FIG. 5), the frame 46 may be positioned between a proximally facing surface or rim of the tack disk 80 and a distally facing surface or rim of the collar 76.

Additionally, it can be appreciated that the collar 76 (which, as described above, may be directly attached to the tack member 84 and indirectly attached to the tack disk 80), may be designed to engage the second connection member 78. For example, FIG. 10 further illustrates that, in some examples, the collar 76 may include a profile which matches the profile of the second connection member 78 of the inner shaft 36. For example, FIG. 10 illustrates that the collar 76 may include a non-circular cross-sectional shape, such as an oval cross-sectional shape, and the second connection member 78 of the inner shaft 36 may include a non-circular cross-sectional shape, such as an oval cross-sectional shape, whereby the oval cross-sectional shape of the second connection member 78 of the inner shaft 36 is designed to mate with the oval cross-sectional shape of the collar 76 when the collar 76 is inserted into the distal end of the second connection member 78. The profile of the collar 76 and the second connection member 78 may also be square, rectangular, round, triangular, polygonal, star-shaped, or any other similar geometric shape. Further, these components may be formed by stamping, swaging, machining, or otherwise shaping the mating portions of the collar 76 and the second connection member 78. Additionally, in some other examples, the second connection member 78 may be attached to the collar 76 via UV adhesive, press fit, heat stake, over-molding, screw threading, etc.

FIG. 11 is a cross-sectional view of tack member 84, the tack disk 80, the collar 76 and the second connection member 78 (which may be machined as a monolithic portion of the distal end portion of the inner shaft 36 or, in other examples, may be a separate component which is attached to the distal end of the inner shaft 36). FIG. 11 further illustrates that distal end region of the tether 82 which has been fixedly attached to the tack member 84, as described above. For example, FIG. 11 illustrates that the tack member 84 may include a proximal stem 94. The proximal stem 94 of the tack member 84 may include a bore within which the distal end region of the tether 82 may be inserted. As discussed above, the proximal stem 94 may be crimped onto the distal end region of the tether 82, thereby attaching the tack member 84 to the tether 82.

FIG. 11 further illustrates that the tack disk 80 may be fixedly attached to the tack member 84. For example, the tack disk 80 may be over-molded onto the tack member 84. FIG. 11 illustrates that the tack member 84 may include one or more rims, ledges, channel, grooves, etc. within which the material of the tack disk 80 may flow during the over-molding process, thereby fixedly attaching the tack disk 80 to the tack member 84 with an interference fit.

Additionally, FIG. 11 illustrates the combination tack disk 80 and tack member 84 positioned within the collar 76. The detailed view of FIG. 11 shows that, in some examples, the collar 76 may include one or more projections 95 (e.g., bumps, circumferential rim, etc.) which are designed to nest within one or more recesses 96 (e.g., cavities, circumferential groove, etc.) located on the stem 94 of the tack member 84. It can be appreciated that the one or more projections 95 extend away from an inner luminal surface of the collar 76 such that projections 95 project into the one or more recesses 96 located on the stem 94 of the tack member 84. Additionally, it can be appreciated the one or more projections 95 and the one or more recesses 96 are designed such that the projections 95 may flex and snap into the recesses 96 as the stem 94 of the tack member 84 is inserted into the lumen of the collar 76. It can be further appreciated that after the one or more projections 95 are snapped into the one or more recesses 96, the tack member 84 may be fixedly attached to the collar 76.

As discussed above, FIG. 11 further illustrates the indentations 91 formed along a portion of the distal end of the inner shaft 36. It can be appreciated from FIG. 11 that the indentations may be designed such that they provide a positive stop to limit the distance that the collar 76 may extend into the second connection member 78. If the collar 76 were to extend too far into the second connection member 78, it may become wedged within the second connection member 78 and may become difficult to release from the second connection member 78. Therefore, the indentations 91 may control the distance for which the collar 76 is inserted into the second connection member 78 and, accordingly, may indirectly control the removal force required to separate the collar 76 from the second connection member 78.

FIG. 12 illustrates an end view of the second connection member 78. FIG. 12 illustrates the indentations 91 (formed from the wall of the second connection member 78) extending radially inward toward the central longitudinal axis of the inner shaft 36. It can be appreciated from FIG. 12 that the indentations 91 may provide a positive stop, beyond which the collar 76 cannot be advanced into the lumen of the second connection member 78. Indentations 91 may have a radially inwardmost extent that is less than the outermost extent of the collar 76 at a proximal end of the collar 76 to prevent the collar 76 from passing proximally of the indentations 91.

Figure 13:
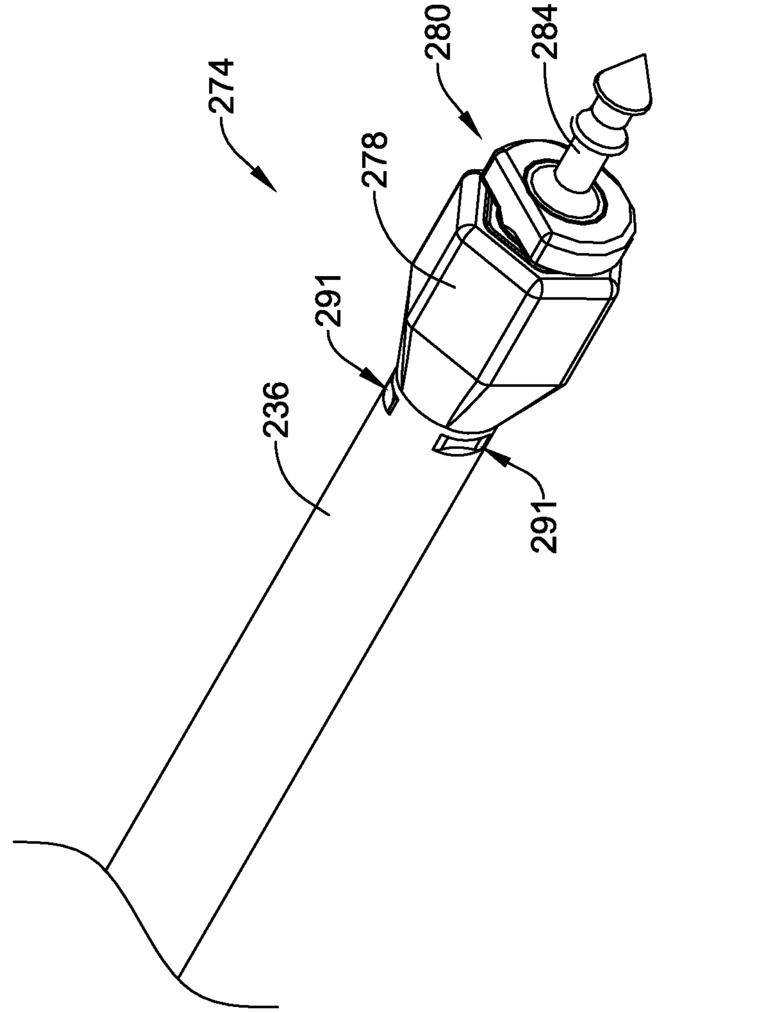
FIG. 13 illustrates a portion of another example implant delivery device.

FIG. 13 illustrates another example connection assembly 274. The connection assembly 274 may be similar in form and function to the connection assembly 74 described above. Specifically, FIG. 13 illustrates the tack disk 280 and the tack member 284 coupled to an inner shaft 236 (the collar 276, which is part of the connection assembly 274, cannot be visualized in FIG. 13 as it is nested within the second connection member 278 of the inner shaft 236). In other words, FIG. 13 illustrates that the collar 276 may be coupled to the tack disk 280, which is in turn coupled to the tack member 284. As discussed above, the collar 276 may be designed to nest within the distal end of the inner shaft 236 (e.g., nest within the aperture or bore of the second connection member 278).

Figure 14:
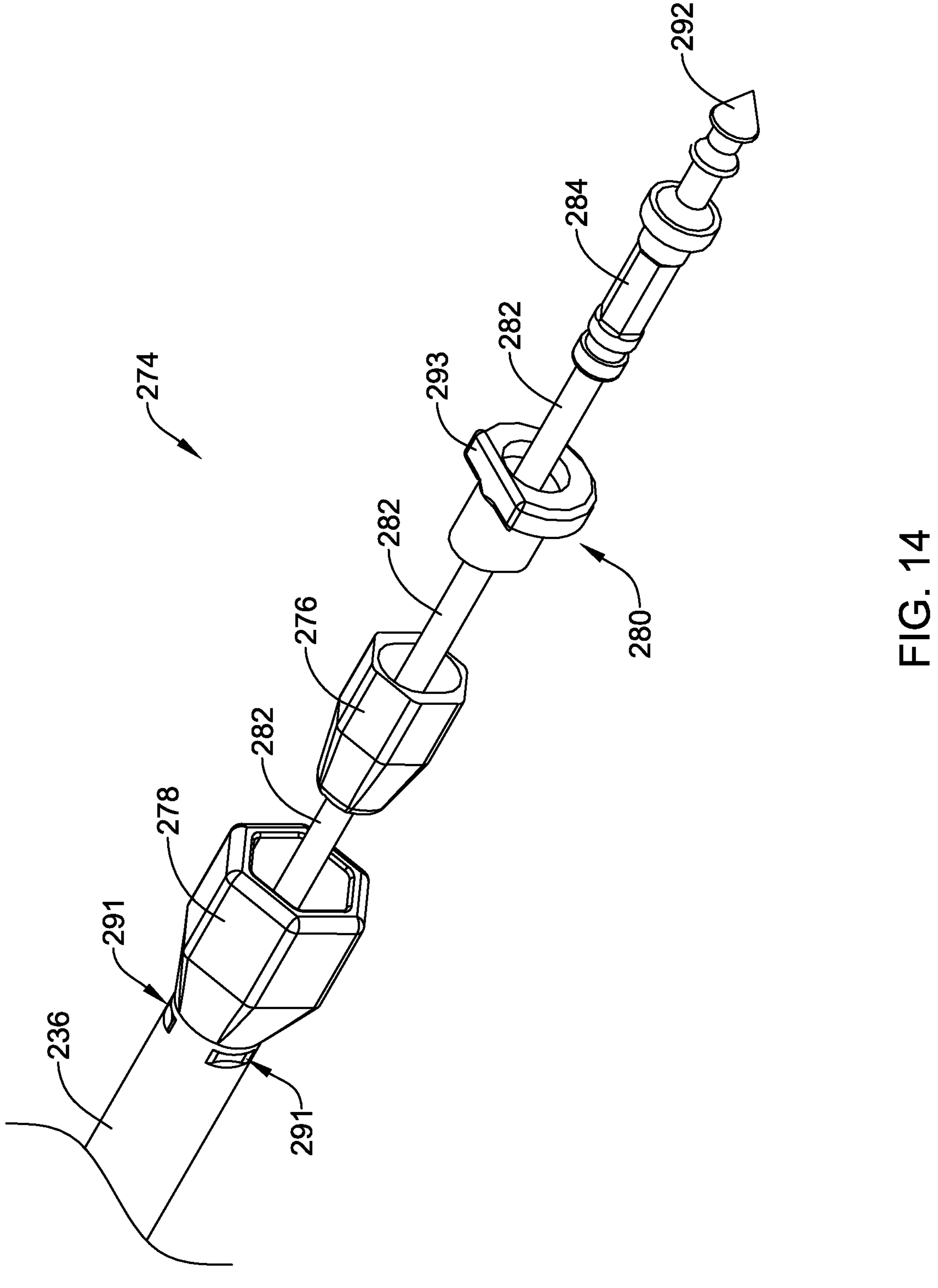
FIG. 14 is an exploded view of the implant delivery device shown in FIG. 13.

FIG. 14 illustrates an exploded view of the connection assembly 274 shown in FIG. 13. For purposes of the discussion herein, it can be appreciated that tack member 284 (including the tapered distal tip 292), the tack disk 280 (including the flat portion 293), the tether 282 and the inner shaft 236 (including the indentations 291) may be similar in form and function to the tack member 84 (including the tapered distal tip 92), the tack disk 80 (including the flat portion 93), the tether 82 and the inner shaft 36 (including the indentations 91) described above.

However, FIG. 14 further illustrates that, in some examples, the second connection member 278 may include a non-circular cross-sectional shape, such as a hexagonal cross-sectional shape, whereby the hexagonal cross-sectional shape of the second connection member 278 is designed to mate with a non-circular cross-sectional shape, such as the hexagonal cross-sectional shape, of the collar 276 when the collar 276 is inserted into the lumen of the second connection member 278. It can be appreciated that, aside of the different cross-sectional shape of the second connection member 278 and the collar 276, all the remaining connection techniques and positioning of the components relative to one another may be similar to that described with respect to the connection assembly 74 described above with respect to FIGS. 9-11.

While FIG. 10 and FIG. 14 illustrate two examples of the collars 76/276 having specific shapes designed to mate with the second connection members 78/278 of the inner shafts 36/236. For example, the collar 76 may include an ovular shape while the collar 276 may include a hexagonal shape. However, it can be appreciated that the collars 76/276 and the distal end of the second connection member 78/278 for with which it is designed to mate, may include a variety of shapes. For example, the collar 76/276 and the distal end of the second connection member 78/278 for with which it is designed to mate, may include square, round, rectangular, star-shaped, triangular, polygonal, etc. shapes. In other instances, the collar 76/276 and the second connection member 78/278 may include mating circular shapes, with other means for coupling and/or limiting rotational movement therebetween.

Figure 15:
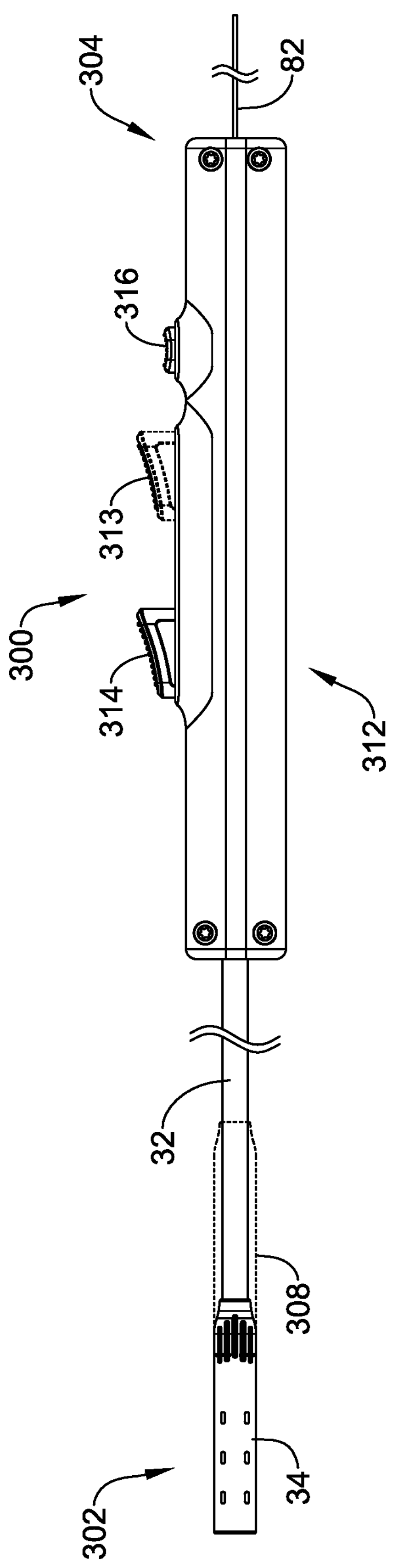
FIG. 15 is a side view of an example implant delivery system.

FIG. 15 illustrates an example implant delivery system 300. The example implant delivery system 300 may include a distal end region 302 and a proximal end region 304. The proximal end region 304 may include a handle 312. The distal end region 302 of the implant delivery system 300 may include a delivery sheath 34 to house the combination frame 46 and implant 12 as described above (the frame 46 and implant 12 are not visible in FIG. 15). FIG. 15 illustrates that the handle 312 may be attached to the delivery sheath 34 via an outer shaft 32.

As discussed above, the delivery sheath 34 may surround the frame 46 and implant 12 when in a delivery configuration. In other words, the frame 46 and implant 12 may be contained in a collapsed, folded delivery configuration within the lumen of the delivery sheath 34 during delivery to a treatment site. For example, it can be appreciated that in a delivery configuration, the implant 12 may be attached to the frame 46, whereby the implant 12 and frame 46 (together) may be folded and positioned within the delivery sheath 34.

Additionally, it can be appreciated that retraction of the outer shaft 32 may release (e.g., deploy) the implant 12 and frame 46 from the delivery sheath 34. In other words, the implant 12 and frame 46 may be positioned within the delivery sheath 34 as the outer shaft 32 is inserted into a patient's body and advanced toward a target delivery site. After being positioned at the delivery site, the outer shaft 32, and delivery sheath 34 secured thereto, may be retracted while the inner shaft 36 (not visible in FIG. 15, but described above) may be held stationary relative to the outer shaft 34. As discussed above, retraction of the outer shaft 32 relative to the inner shaft 36 and frame 46 may retract the delivery sheath 34 relative thereto, which uncovers (e.g., releases) and deploys the implant 12 and the frame 46.

Further, it can be appreciated from FIG. 15 that the outer shaft 32 may be retracted via actuation (e.g., retraction) of an actuation member 314. For example, FIG. illustrates the actuation member 314 may be fixedly secured to a proximal end of the outer shaft 32, while a proximal end of the inner shaft 36 may be fixedly secured to the housing of the handle 312. The actuation member 314 may be shifted from a position in which it is closer to the distal end 302 of the delivery system 300 to a position in which it is closer to the proximal end 304 of the delivery system 300. The dotted outline 313 shows the final position of the actuation member 314 after it has been retracted in a distal-to-proximal direction to effect deployment of the frame 46 and implant 12 therefrom. As discussed above, retraction of the outer shaft 32 relative to the inner shaft 36 may also retract the delivery sheath 34, thereby deploying the frame 46 and implant 12. The dotted outline 308 of the delivery sheath illustrates the final position of the delivery sheath 34 after being retracted in a distal-to-proximal direction.

In some examples, the delivery system 300 may include a mechanism which may clamp and secure the tether member 82, such as a proximal portion of the tether member 82 extending proximally from the lumen of the inner shaft 36. FIG. 15 illustrates the tether 82 which may extend from the tack member (not shown in FIG. 15) through the handle 312 to a position outside the handle 312 (e.g., through the handle 312 to a location proximal of the handle 312). As discussed above, the tether 82 may be secured to the frame 46 via a connection assembly, or otherwise secured to the frame 46, as described above. FIG. 15 illustrates that delivery system 300 may include a tether clamp mechanism 316. The tether clamp mechanism 316 will be discussed in greater detail below.

Figure 16:
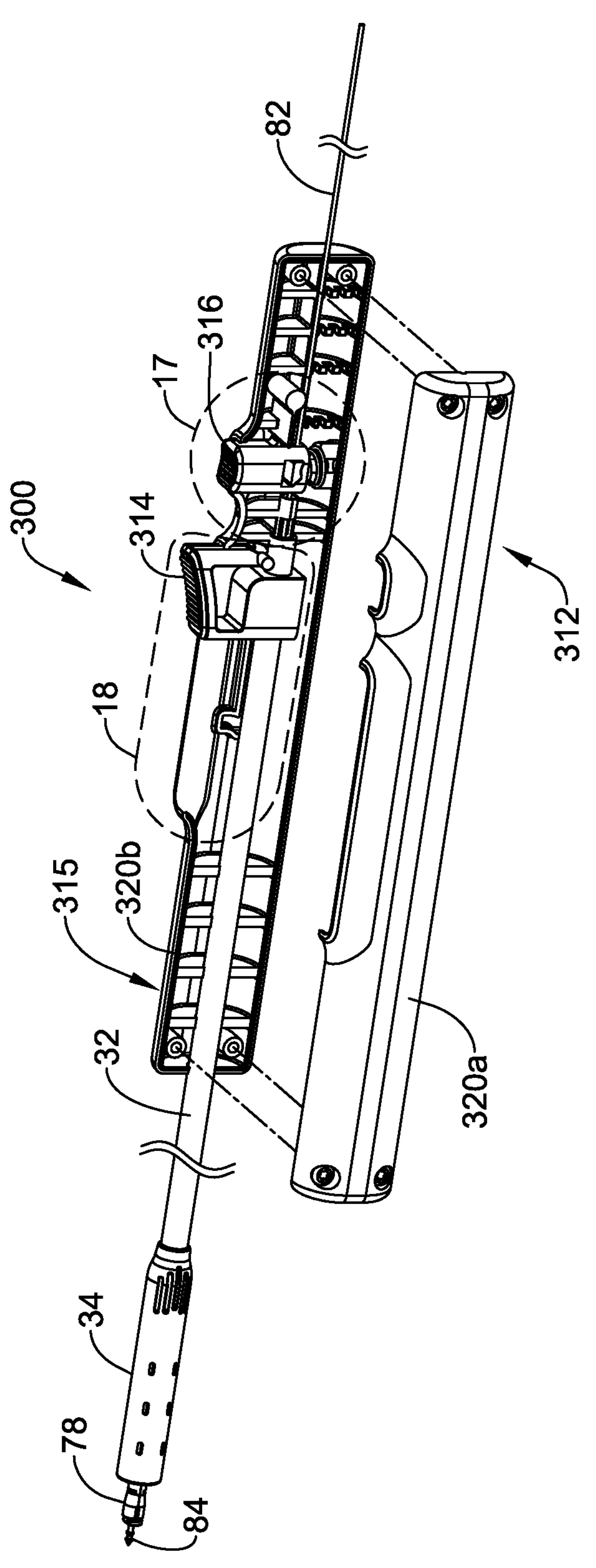
FIG. 16 is a perspective view of the implant delivery system shown in FIG. 15.

FIG. 16 further illustrates the implant delivery system 300 described above. In particular, FIG. 16 illustrates a partially exploded view of the handle 312 shown in FIG. 15. As illustrated in FIG. 16, the handle 312 may include a housing 315 having a first handle portion **320*a* and a second handle portion 320*b*. The first and second handle portions 320*a*/320*b* may be attached together in a clamshell configuration. In other words, the first handle portion 320*a* and the second handle portion 320*b* may be attached together via screws, a snap-fit, adhesive, etc. to form the housing 315**.

FIG. 16 further illustrates that the handle housing 315 may include the actuation member 314, the tether clamp 316 and a portion of the outer shaft 32 extending from the actuation member 314 to the delivery sheath 34. As discussed above, FIG. 16 further illustrates the tether 82 may extend from the tack member 84 (discussed above), through the lumen of the inner shaft 36 (not visible in FIG. 16) extending through the outer shaft 32, through the tether clamp mechanism 316 and thereafter exit the proximal end region of the housing 315. The tether clamp 316 may fixedly secure the tether 82 from relative longitudinal movement relative to the inner shaft 36 when in a locked position. It can be appreciated that FIG. 16 illustrates the actuation member 314 located in a retracted position, whereby the delivery sheath 34 has been retracted such that a portion of the second connection member 78 and the tack member 84 is visible. As discussed above, the retracted position of the delivery sheath 34 may be the position in which the implant 12 and frame 46 may be released from the delivery sheath 34.

Figure 17:
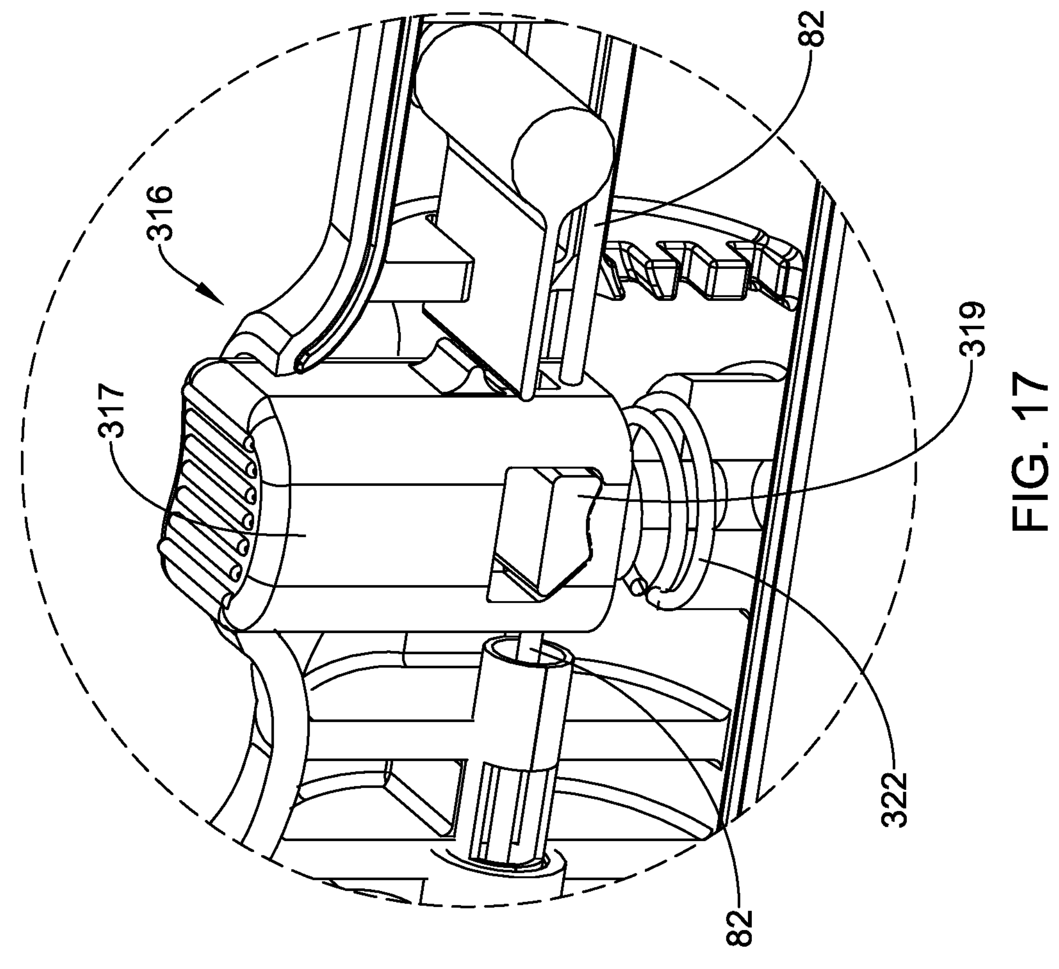
FIG. 17 is a detailed view of a portion of the implant delivery system shown in FIG. 16.

FIG. 17 illustrates a detailed view of the tether clamp mechanism 316 described above. The tether clamp mechanism 316 may include a button 317 which is designed to translate vertically within a portion of the second handle portion 320*b*. The button 317 may be biased to extend upward toward the "top" of the second handle portion 320*b* via a spring 322 positioned underneath the button 317. In other words, in order to actuate the button 317, a clinician may have to press the button 317 into the housing 315 to overcome the upward vertical force of the spring 322.

FIG. 17 further illustrates the tether 82 extending through an aperture in the button 317, whereby the tether 82 is effectively "pinched" between a portion of the button 317 and a tether stop member 319 in a locked or engaged configuration. In other words, while the tether 82 is positioned between the tether stop member 319 and the button 317, the spring 322 may exert a vertical force on the button 317 to pinch the tether 82 between the button 317 and the tether stop member 319. The force applied by the spring 322 prevents the tether 82 from shifting with respect to the housing 315. However, it can be appreciated that when the button 317 is depressed to an unlocked of disengaged configuration, the spring 322 is compressed and the pinching force applied to the tether 82 is removed, thereby permitting the tether 82 to shift with respect to the housing 315. It can be appreciated that a clinician may press and release the button 317 while manipulating the implant delivery device 300, thereby allowing the clinician to manipulate the tether 82 relative to the housing 315 and the delivery sheath 342.

Figure 18:
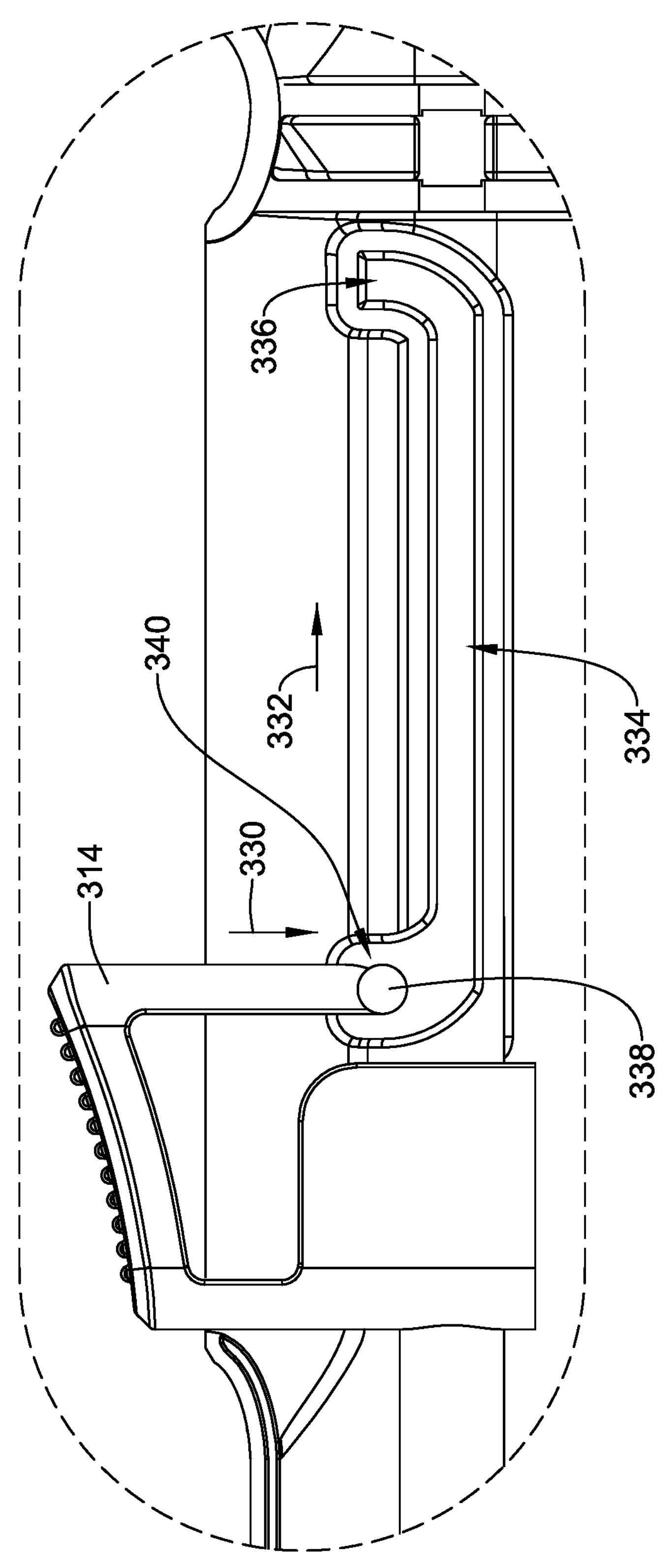
FIG. 18 is another detailed view of a portion of the implant delivery system shown in FIG. 17.

FIG. 18 illustrates a detailed view of the portion of the housing 315. Specifically, FIG. 18 illustrates an inner surface of the second handle portion 320*b*. FIG. 18 illustrates that the actuation member 314 may have a first end projection 338 positioned within a track 334 (e.g., groove, channel, etc.) formed in the inner surface of the second handle portion 320*b*. It can be appreciated that the first end projection 338 of the actuation member 314 may be engaged with the track 334 such that the first end projection 338 is restricted from traveling anywhere except along the path of the track 334.

It can be further appreciated that, to shift the actuation member 314 along the track 334 in a distal-to-proximal direction, the first end projection 338 may need to be initially translated vertically within a distal transverse portion of the track 334 defined by the reference numeral 340, followed by shifting longitudinally (e.g., horizontally) along the track 334, before translating the first end projection 338 vertically upward such that it comes to rest in the proximal transverse portion of the track defined by the reference numeral 336. It can be further appreciated that the actuation member 314 may be "locked" (e.g., prevented from longitudinal or horizontal translation) when the first end projection 338 is positioned in the transverse portions of the track 334 defined by the reference numerals 340 and 336.

Additionally, it can be appreciated that, in practice, a clinician may need to press down on the actuation member 314 (e.g., flex the "top" portion of the actuation member 314 downward) to translate the first end projection 338 in the transverse portion of the track 334 defined by the reference numeral 340 (the downward translation is depicted by the arrow 330), followed by pulling the actuation member 314 in a distal-to-proximal direction (the longitudinal or horizontal translation is depicted by the arrow 332), and then releasing the actuation member 314 to permit the first end 338 of the actuation member 314 to translate vertically upward within the transverse portion of the track 334 defined by the reference numeral 336. It can be further appreciated that to shift the actuation member 314 in a proximal-to-distal direction, the steps described above may be reversed.

Figure 19:
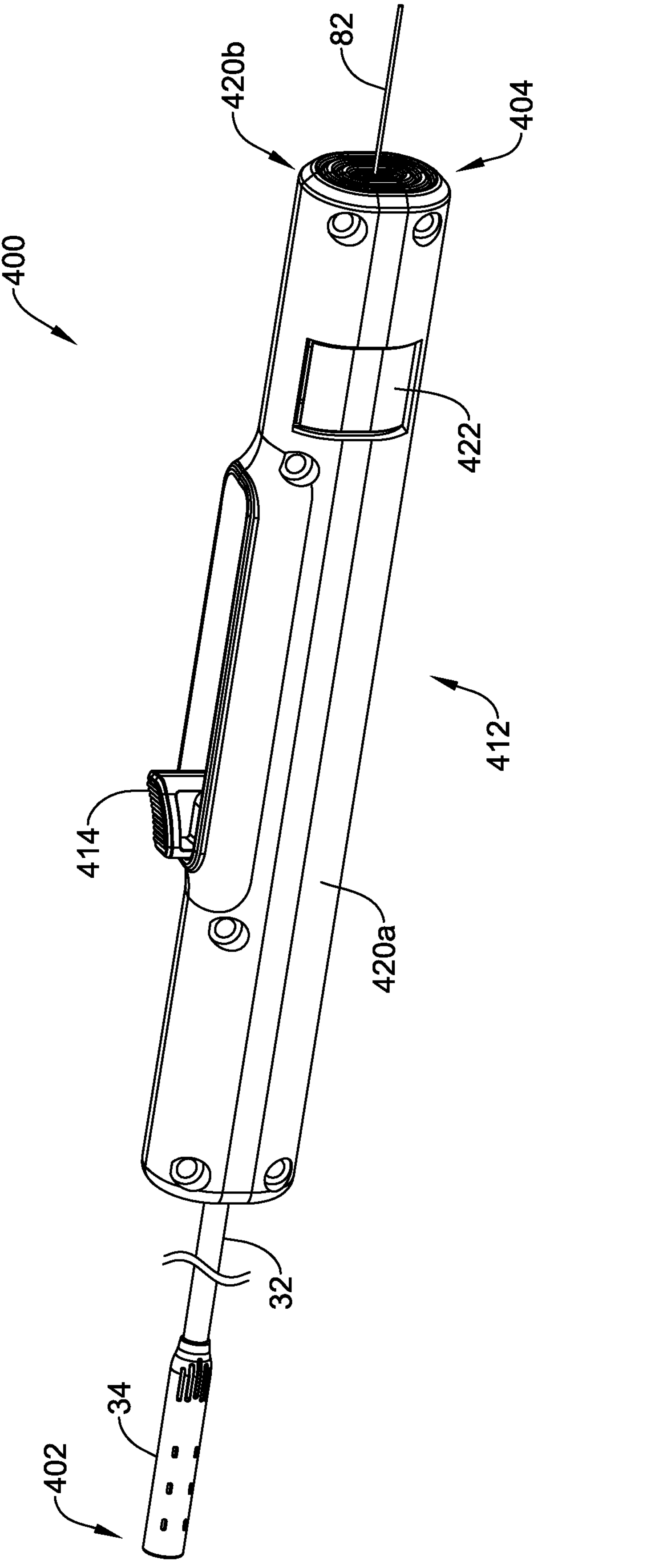
FIG. 19 is a perspective view of another example implant delivery system.

FIG. 19 illustrates another example implant delivery system 400. The example implant delivery system 400 may include a distal end region 402 and a proximal end region 404. The proximal end region 404 may include a handle 412. As described above, the distal end region 402 of the implant delivery system 400 may include a delivery sheath 34. FIG. 19 illustrates that the handle 412 may be attached to the delivery sheath 34 via an outer shaft 32.

It can be appreciated that the delivery sheath 34, the outer shaft 32, the inner shaft 36 (not visible in FIG. 19) and the tether 82 may be similar in form and function to the delivery sheath 34, the outer shaft 32, the inner shaft 36 (not visible in FIG. 19) and the tether 82 described above with respect to the other delivery systems described herein (e.g., the delivery system 300). For example, the retraction of the outer shaft 36, and delivery sheath 34 secured thereto, may release (e.g., deploy) the implant 12 and frame 46 from the delivery sheath 34. Similarly, the tether member 82 may extend through a lumen in the inner shaft 36 and be coupled to the frame 46.

Further, it can be appreciated from FIG. 19 that the outer shaft 32 may be retracted via actuation (e.g., retraction) of an actuation member 414. For example, the actuation member 414 may be fixedly secured to a proximal end of the outer shaft 32 while a proximal end of the inner shaft 36 may be fixedly secured to the housing of the handle 412. The actuation member 414 may be shifted from a position in which it is closer to the distal end 402 (shown in FIG. 19) of the delivery system 400 to a position in which it is closer to the proximal end 404 (shown in FIG. 20) of the delivery system 400. As discussed above, retraction of the outer shaft 32 relative to the inner shaft 36 may also retract the delivery sheath 34, thereby deploying the frame 46 and implant 12.

Figure 20:
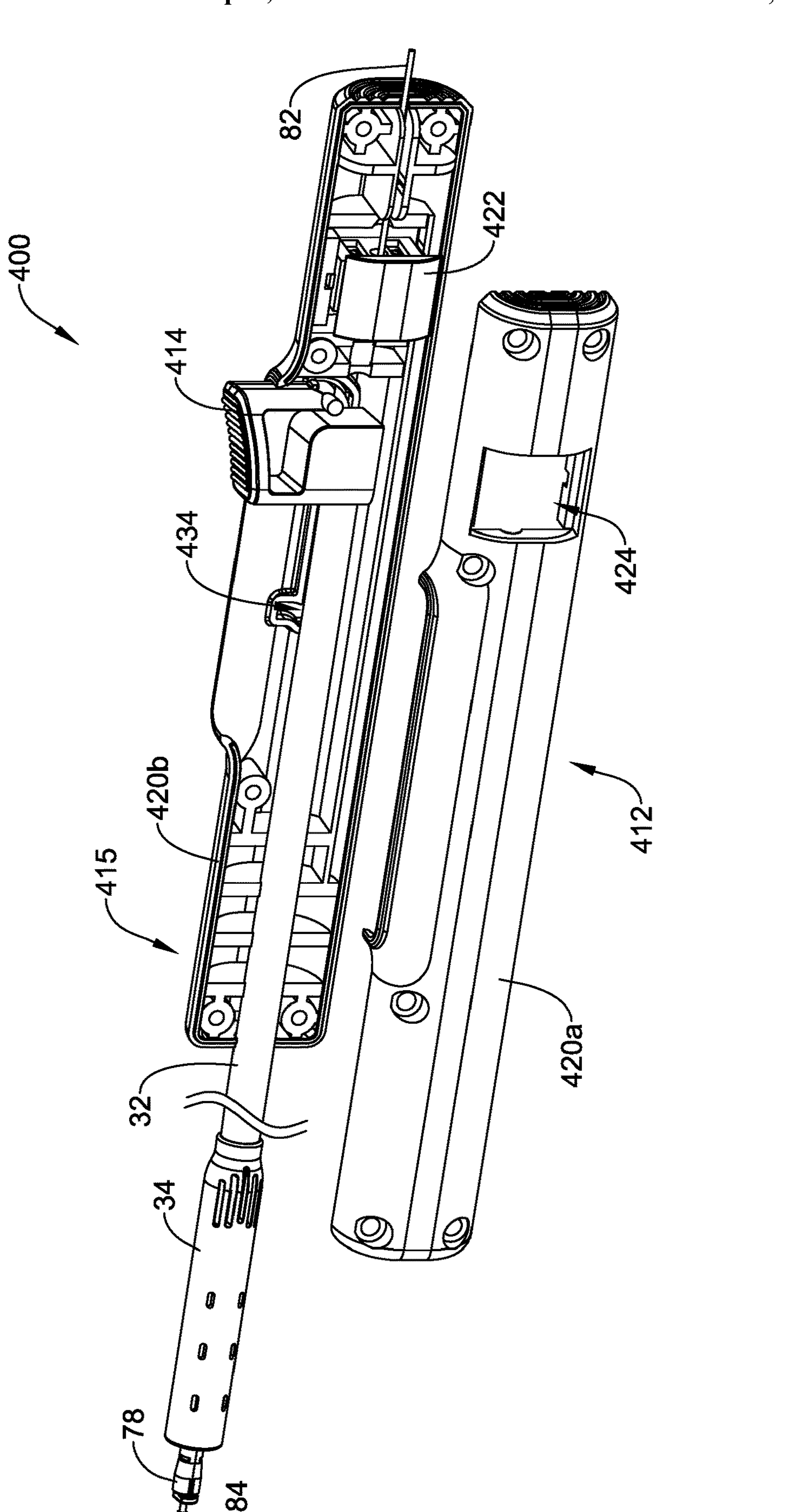
FIG. 20 is another perspective view of the implant delivery system shown in FIG. 19.

FIG. 20 illustrates the implant delivery system 400 described above. In particular, FIG. 20 illustrates a partially exploded view of the handle 412 shown in FIG. 19. As illustrated in FIG. 20, the handle 412 may include a housing 415 having a first handle portion 420*a* and a second handle portion 420*b*. The first and second handle portions 420*a*/420*b* may be attached together in a clamshell configuration. In other words, the first handle portion 420*a* and the second handle portion 420*b* may be attached together via screws, a snap-fit, etc. to form the housing 415.

FIG. 20 further illustrates that the handle housing 415 may include the actuation member 414, a tether clamp 422 and a portion of the outer shaft 32 extending from the actuation member 414 to the delivery sheath 34. As discussed above, FIG. 20 further illustrates the tether 82 may extend from the tack member 84 (discussed above), through the lumen of the inner shaft 36 (not visible in FIG. 20) extending through the outer shaft 32, through the tether clamp mechanism 422 and thereafter exit the proximal end region of the housing 415. It can be appreciated that FIG. 20 illustrates the actuation member 414 located in a retracted position as compared to its position shown in FIG. 19 (e.g., after having been translated in a distal-to-proximal direction). It can be further appreciated that when the actuation member 414 is in a retracted position, the delivery sheath 34 may been retracted such that a portion of the second connection member 78 and the tack member 84 are visible. As discussed above, the retracted position of the delivery sheath 34 may be the position in which the implant 12 and frame 46 may be released from the delivery sheath 34.

The tether clamp 422 shown in FIG. 20 may include a "push-button" style clamp which is designed to translate transversely relative to the longitudinal axis of the handle housing 415. For example, the tether clamp 422 is designed to be secured to a portion of the inner surface of the second handle portion 420*b* and extend through an aperture 424 in the first handle portion 420*a*. It can be appreciated that this configuration permits a user to push the tether clamp 422 transversely inward toward the longitudinal axis of the handle housing 415. In some examples, the tether clamp 422 may be coupled to a spring (not shown in FIG. 20) which biases the tether clamp 422 outward, away from the second handle portion 420*b* in a resting state. It can be appreciated that the first handle portion 420*a* may include one or more features which prevent the tether clamp 422 from passing all the way through the aperture 424 while in the resting state. Hence, in its resting state, the spring may effectively push the tether clamp 422 against the inside surface of the first handle portion 420*a*. However, as discussed above, a portion of the tether clamp 422 is accessible via aperture 424 while the tether clamp 422 is in the resting state.

Figure 21:
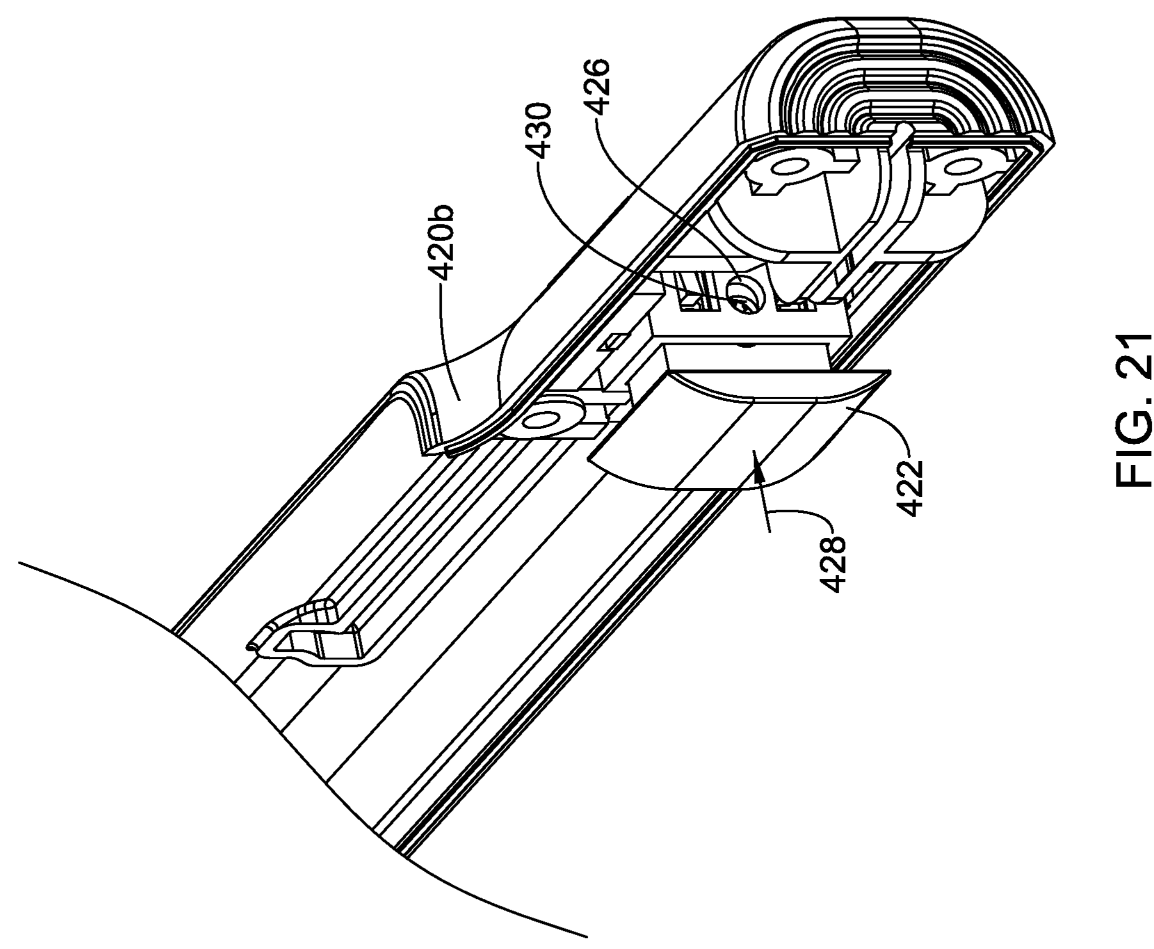
FIG. 21 is a detailed view of a portion of the implant delivery system shown in FIG. 20.

FIG. 21 illustrates a detailed view of the tether clamp 422 engaged with the second handle portion 420*b*. As described above, the tether clamp 422 may be designed to translate in a transverse direction relative to the longitudinal axis of the second handle portion 420*b*. As discussed above, the tether clamp 422 may be biased outward, away from the second handle member 420*b* via a spring (not visible in FIG. 21) positioned between the tether clamp 422 and the second handle member 420*b*. It can be appreciated that to actuate the tether clamp 422, a clinician may have to press the tether clamp 422 toward the second handle portion 420*b* to overcome the transverse force applied by the spring.

FIG. 21 further illustrates that the tether 82 (omitted from FIG. 21 for clarity) may extend through both a first aperture 426 located in the second handle portion 420*b* and a second aperture 430 located in the tether clamp 422. It can be appreciated that when the tether clamp 422 is in a resting state with the spring pushing the tether clamp 422 away from the second handle portion 420*b* (and therefore not be pushing inward toward the second handle portion 420*b*) the first aperture 426 and the second aperture 430 may not be longitudinally aligned, and therefore, may effectively "pinch" a portion of the tether 82 between the inner wall surfaces which define the first aperture 426 and the second aperture 430. In other words, the spring (not visible in FIG. 21) may effectively push the tether clamp 422 outward, thereby causing the second aperture 430 to slide outward relative to the first aperture 426, thereby pinching the tether 82 between the peripheral surface of the first aperture 426 and the peripheral surface of the second aperture 430. The force applied by the spring may prevent the tether 82 from shifting with respect to the housing 415.

It can be appreciated that when the tether clamp 422 is pushed inward (as shown by the arrow 428), the second aperture 430 may become longitudinally aligned with the first aperture 426, which releases the pinching force applied to the tether 82, and thereby permits the tether 82 to shift with respect to the housing 415. It can be appreciated that a clinician may press and release the tether clamp 422 while manipulating the implant delivery device 400, thereby allowing the clinician to manipulate the tether 82 relative to the housing 415 and the outer shaft 32.

Figure 22:
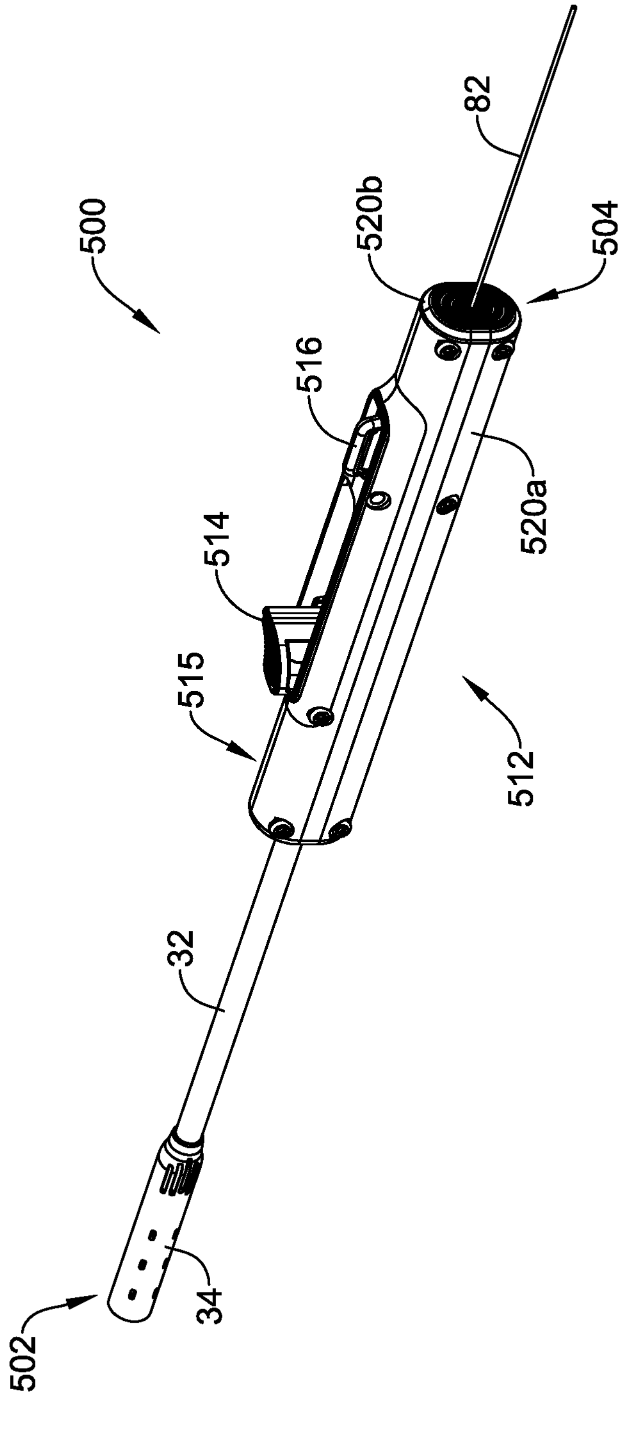
FIG. 22 is a perspective view of another example implant delivery system.

FIG. 22 illustrates another example implant delivery system 500. The example implant delivery system 500 may include a distal end region 502 and a proximal end region 504. The proximal end region 504 may include a handle 512. As described above, the distal end region 502 of the implant delivery system 500 may include a delivery sheath 34. FIG. 22 illustrates that the handle 512 may be attached to the delivery sheath 34 via an outer shaft 32.

It can be appreciated that the delivery sheath 34, the outer shaft 32, the inner shaft 36 (not visible in FIG. 22) and the tether 82 may be similar in form and function to the delivery sheath 34, the outer shaft 32, the inner shaft 36 (not visible in FIG. 22) and the tether 82 described above with respect to the other delivery systems described herein (e.g., the delivery systems 300/400). For example, the retraction of the outer shaft 32, and delivery sheath 34 secured thereto, may release (e.g., deploy) the implant 12 and frame 46 from the delivery sheath 34. Similarly, the tether member 82 may extend through a lumen in the inner shaft 36 and be coupled to the frame 46.

Further, it can be appreciated from FIG. 22 that the outer shaft 32 may be retracted via actuation (e.g., retraction) of an actuation member 514. For example, the actuation member 514 may be fixedly secured to a proximal end of the outer shaft 32 while a proximal end of the inner shaft 36 may be fixedly secured to the housing of the handle 512. The actuation member 514 may be shifted from a position in which it is closer to the distal end 502 of the delivery system 500 to a position in which it is closer to the proximal end 504 of the delivery system 500. As discussed above, retraction of the outer shaft 32 relative to the inner shaft 36 may also retract the delivery sheath 34, thereby deploying the frame 46 and implant 12.

Figure 23:
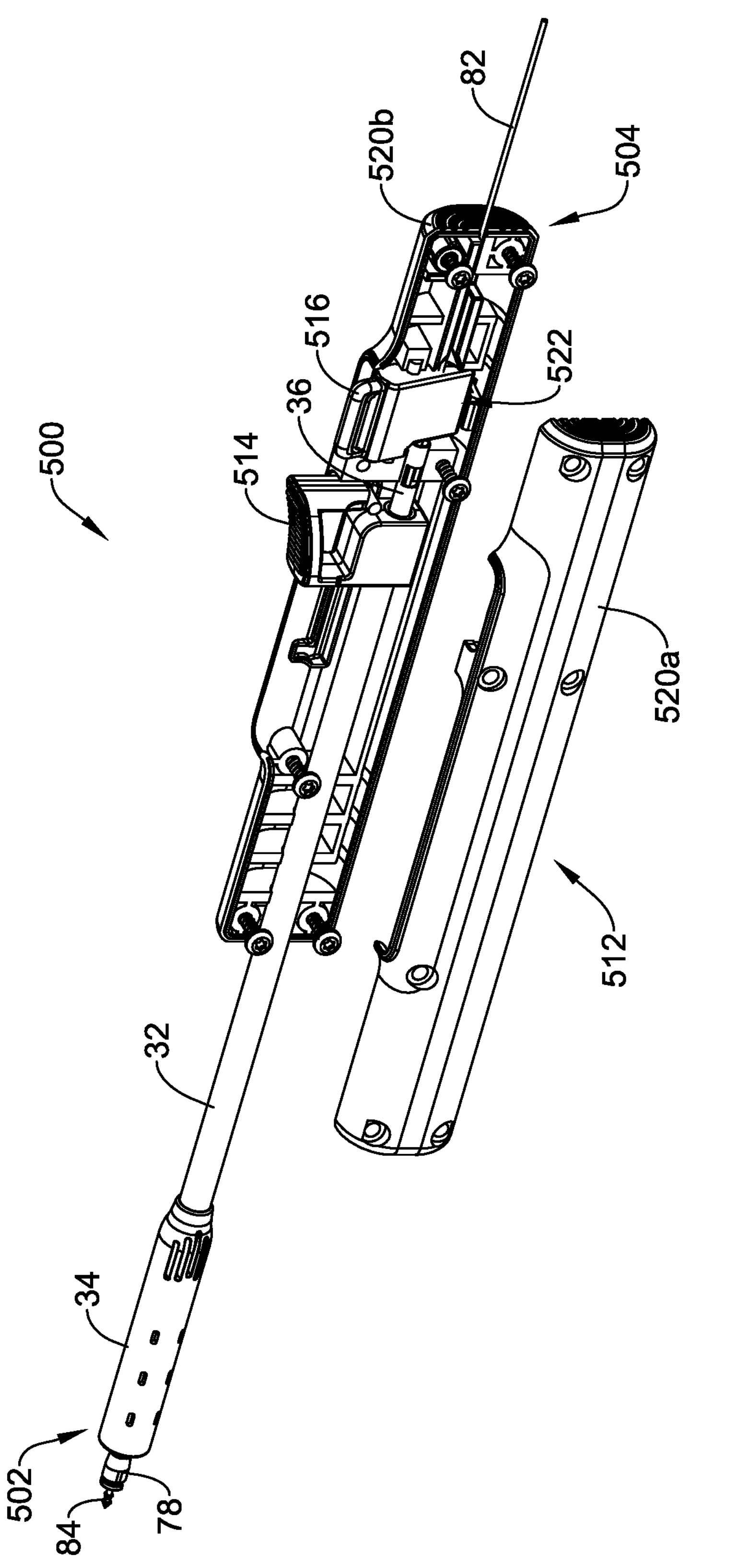
FIG. 23 is another perspective view of the implant delivery system shown in FIG. 22.

FIG. 23 illustrates the implant delivery system 500 described above. In particular, FIG. 23 illustrates a partially exploded view of the handle 512 shown in FIG. 22. As illustrated in FIG. 23, the handle 512 may include a housing 515 having a first handle portion 520*a* and a second handle portion 520*b*. The first and second handle portions 520*a*/520*b* may be attached together in a clamshell configuration. In other words, the first handle portion 520*a* and the second handle portion 520*b* may be attached together via screws, a snap-fit, etc. to form the housing 515.

FIG. 23 further illustrates that the handle housing 515 may include the actuation member 514, a tether clamp 522 and a portion of the outer shaft 32 extending from the actuation member 514 to the delivery sheath 34. The tether clamp 522 may further include a "toggle" style switch 516 which is designed to toggle across the longitudinal axis of the handle housing 515.

As discussed above, FIG. 23 further illustrates the tether 82 may extend from the tack member 84 (discussed above), through the lumen of the inner shaft 36 (not visible in FIG. 22) extending through the outer shaft 32, through the tether clamp 522 and thereafter exit the proximal end region of the housing 515. It can be appreciated that FIG. 23 illustrates the actuation member 514 located in a retracted position as compared to its position shown in FIG. 22 (e.g., after having been translated in a distal-to-proximal direction). It can be further appreciated that when the actuation member 514 is in a retracted position, the delivery sheath 34 may been retracted such that a portion of the second connection member 78 and the tack member 84 are visible. As discussed above, the retracted position of the delivery sheath 34 may be the position in which the implant 12 and frame 46 may be released from the delivery sheath 34.

Figure 24:
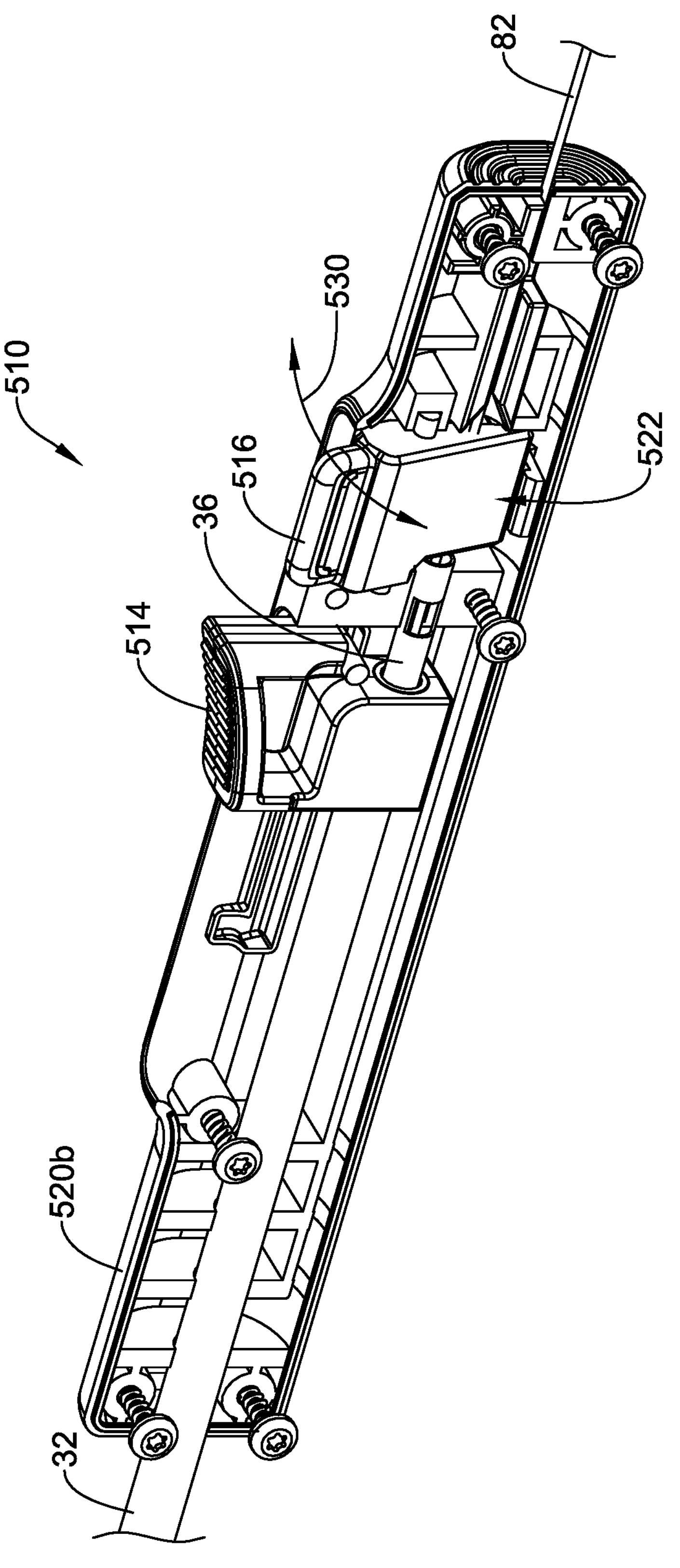
FIG. 24 is a detailed view of a portion of the implant delivery system shown in FIG. 23.

FIG. 24 illustrates a detailed view of the tether clamp 522 engaged with the second handle portion 520*b*. As described above, the tether clamp 522 may be designed to include a toggle switch 516. The toggle switch 516 may be designed to toggle across the longitudinal axis of the handle housing 515. For example, the toggle switch 516 may be designed to toggle from a first position in which it closer to the first handle portion 520*a* (not shown in FIG. 24) to a second position in which it is closer to the second handle portion 520*b*. The path through which the toggle switch 516 may follow when being actuated is shown by the arrow 530 in FIG. 24. It can be appreciated that placing the toggle switch 516 in a first position (e.g., a position closer to the first handle member 520*a*) may permit the tether 82 to shift with respect to the housing 515. Further, toggling the toggle switch 516 to a second position (e.g., a position closer to the second handle member 520*b*) through the path represented by the arrow 530, may secure the tether 82 within the tether clamp 522 such that the tether 82 cannot shift with respect to the housing 515. The toggle switch 516 may be movable across (i.e., cross over) the longitudinal axis of the outer shaft 32 and the inner shaft 34 between the first position and the second position. It can be appreciated that a clinician may toggle the toggle switch 516 (between the first position and the second position) while manipulating the implant delivery device 500 to selectively lock and unlock the tether 82, thereby allowing the clinician to manipulate the tether 82 relative to the housing 515 and the outer shaft 32.

Figure 25:
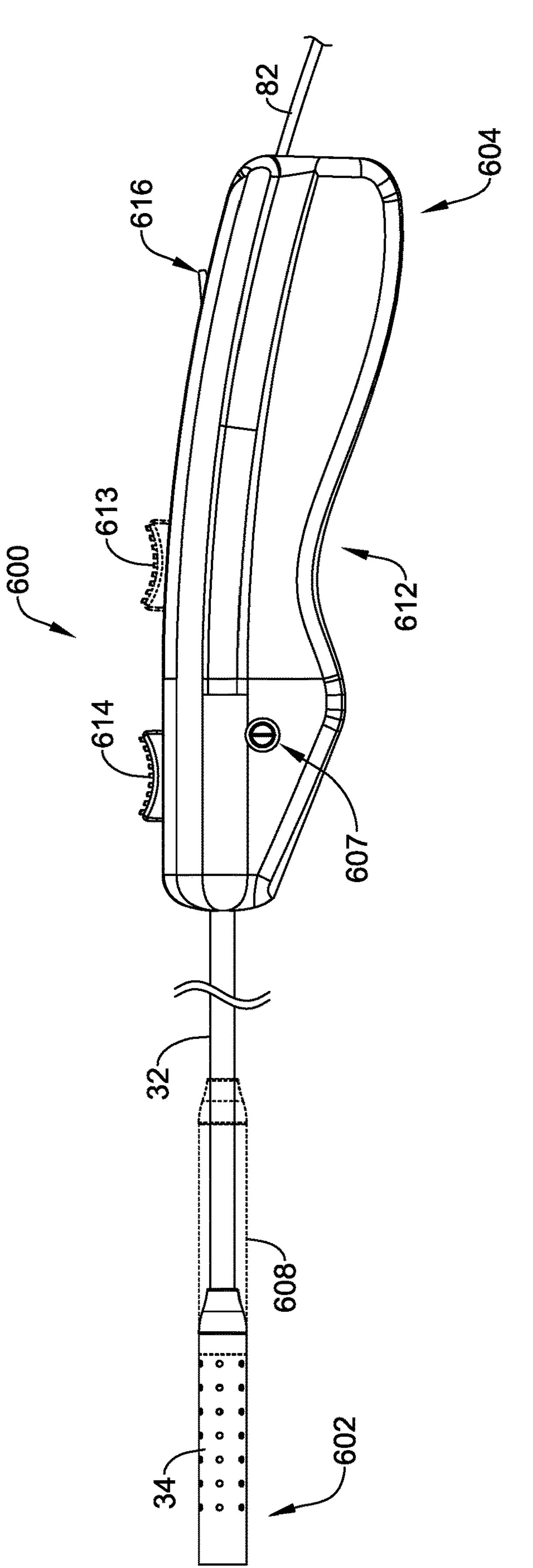
FIG. 25 is a side view of another example implant delivery system.

FIG. 25 illustrates another example implant delivery system 600. The example implant delivery system 600 may include a distal end region 602 and a proximal end region 604. The proximal end region 604 may include a handle 612. As described above, the distal end region 602 of the implant delivery system 600 may include a delivery sheath 34. FIG. 25 illustrates that the handle 612 may be attached to the delivery sheath 34 via an outer shaft 32.

It can be appreciated that the delivery sheath 34, the outer shaft 32, the inner shaft 36 (not visible in FIG. 25) and the tether 82 may be similar in form and function to the delivery sheath 34, the outer shaft 32, the inner shaft 36 (not visible in FIG. 25) and the tether 82 described above with respect to the other delivery systems (e.g., the implant delivery systems 300/400/500) described herein. For example, the retraction of the outer shaft 32 may release (e.g., deploy) the implant 12 and frame 46 from the delivery sheath 34. Similarly, the tether member 82 may extend through a lumen in the inner shaft 36 and be coupled to the frame 46.

Further, it can be appreciated from FIG. 25 that the outer shaft 32 may be retracted via retraction of an actuation member 614. For example, FIG. 25 illustrates the actuation member 614 may be fixedly secured to a proximal end of the outer shaft 32, while a proximal end of the inner shaft 36 may be fixedly secured to the housing of the handle 612. The actuation member 614 may be shifted from a position in which it is closer to the distal end 602 of the delivery system 600 to a position in which it is closer to the proximal end 604 of the delivery system 600. The final position of the actuation member 614 after it has been retracted in distal-to-proximal direction is shown by the dotted outline 613. As discussed above, retraction of the outer shaft 32 relative to the inner shaft 36 may also retract the delivery sheath 34, thereby deploying the frame 46 and implant 12. FIG. 25 illustrates the final position of the delivery sheath 34 after being retracted in a distal-to-proximal direction is shown by the dotted line 608.

FIG. 25 further illustrates that the handle 612 may further include a trigger lock 607. It can be appreciated that trigger lock 607 may be designed to lock the actuation member 614 in a position in which it is closer to the distal end 602 of the delivery system 300 (as shown in FIG. 25), while actuation of the trigger lock 607 may free the actuation member 614 to be retracted in distal-to-proximal direction (as discussed above, the retracted position of the actuation member 614 is shown by the dotted outline 613 in FIG. 25).

In some examples, the delivery system 600 may include a mechanism which may clamp and secure the tether 82, such as a proximal portion of the tether 82 extending proximally from the lumen of the inner shaft 36. FIG. 25 illustrates the tether 82 which may extend from the tack member (not visible in FIG. 25, but described above) through the handle 612 to a position outside the handle 612. As discussed above, the tether 82 may be secured to the frame 46 via a connection member, or otherwise secured to the frame 46, as described above. FIG. 25 illustrates that delivery system 600 may include a tether clamp mechanism 616. The tether clamp mechanism 616 will be discussed in greater detail below.

Figure 26:
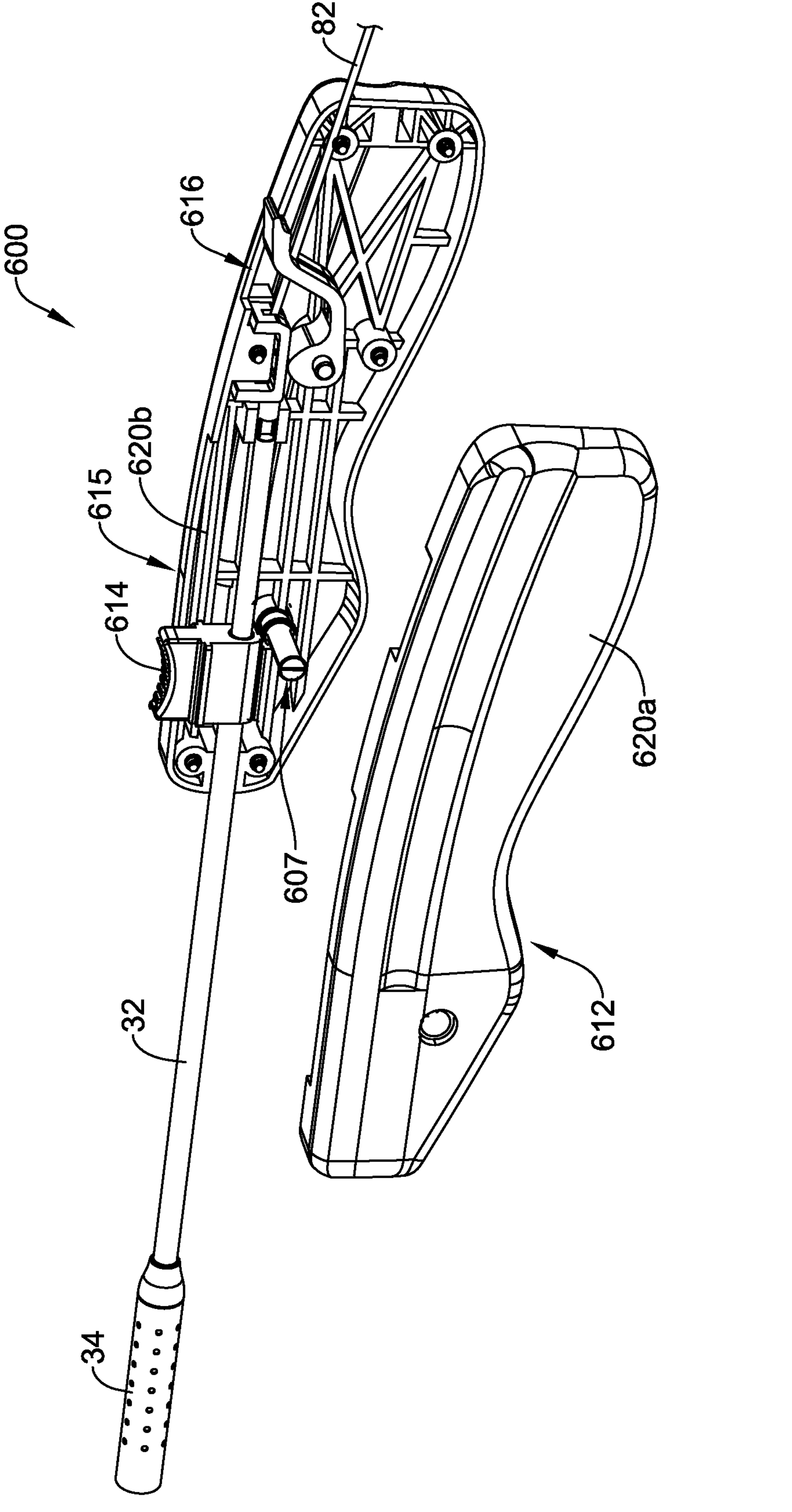
FIG. 26 is a perspective view of the implant delivery system shown in FIG. 25.

FIG. 26 illustrates the implant delivery system 600 described above. In particular, FIG. 26 shows an exploded view of the handle 612 shown in FIG. 25. As illustrated in FIG. 26, the handle 612 may include a housing 615 having a first handle portion 620*a* and a second handle portion 620*b*. The first and second handle portions 620*a*/620*b* may be attached together in a clamshell configuration. In other words, the first handle portion 620*a* and the second handle portion 620*b* may be attached together via screws, snap-fit, etc. to form the housing 615.

FIG. 26 further illustrates that the delivery system 600 may include the actuation member 614, the tether clamp mechanism 616 and a portion of the outer shaft 32 positioned within the handle housing 615, whereby a portion of the outer shaft 32 may extend from the actuation member 614 to the delivery sheath 34. As discussed above, FIG. 26 further illustrates the tether 82 may extend from the tack member 84 (not shown in FIG. 26, but discussed above), through the inner shaft 36 extending through the outer shaft 32, through the tether clamp mechanism 616 and thereafter exit the proximal end region of the housing 615. The tether clamp mechanism 616 may fixedly secure the tether 82 from relative longitudinal movement relative to the inner shaft 36 when in a locked position.

Figure 27:
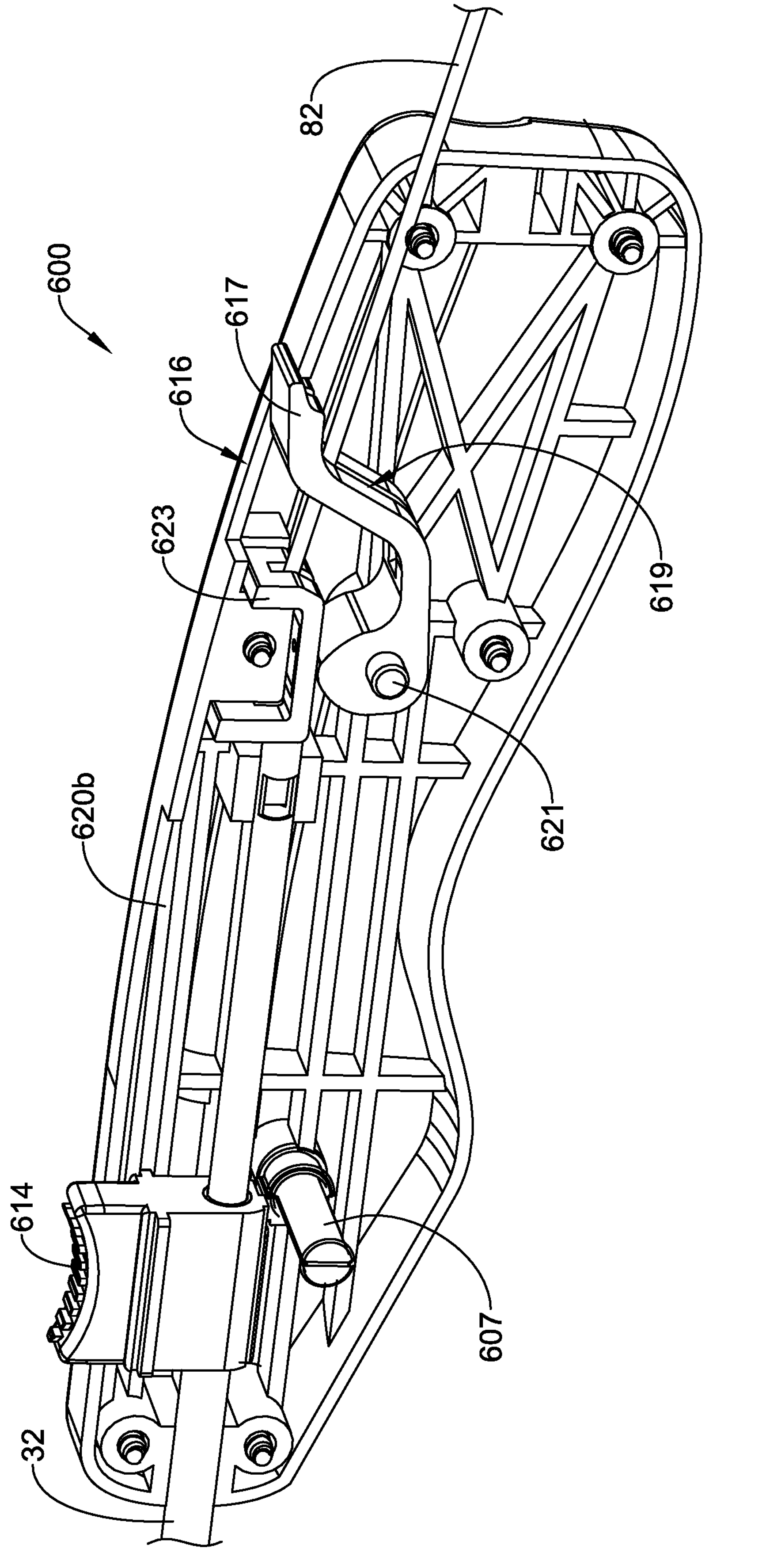
FIG. 27 is a detailed view of a portion of the implant delivery device shown in FIG. 26.
Figure 28:
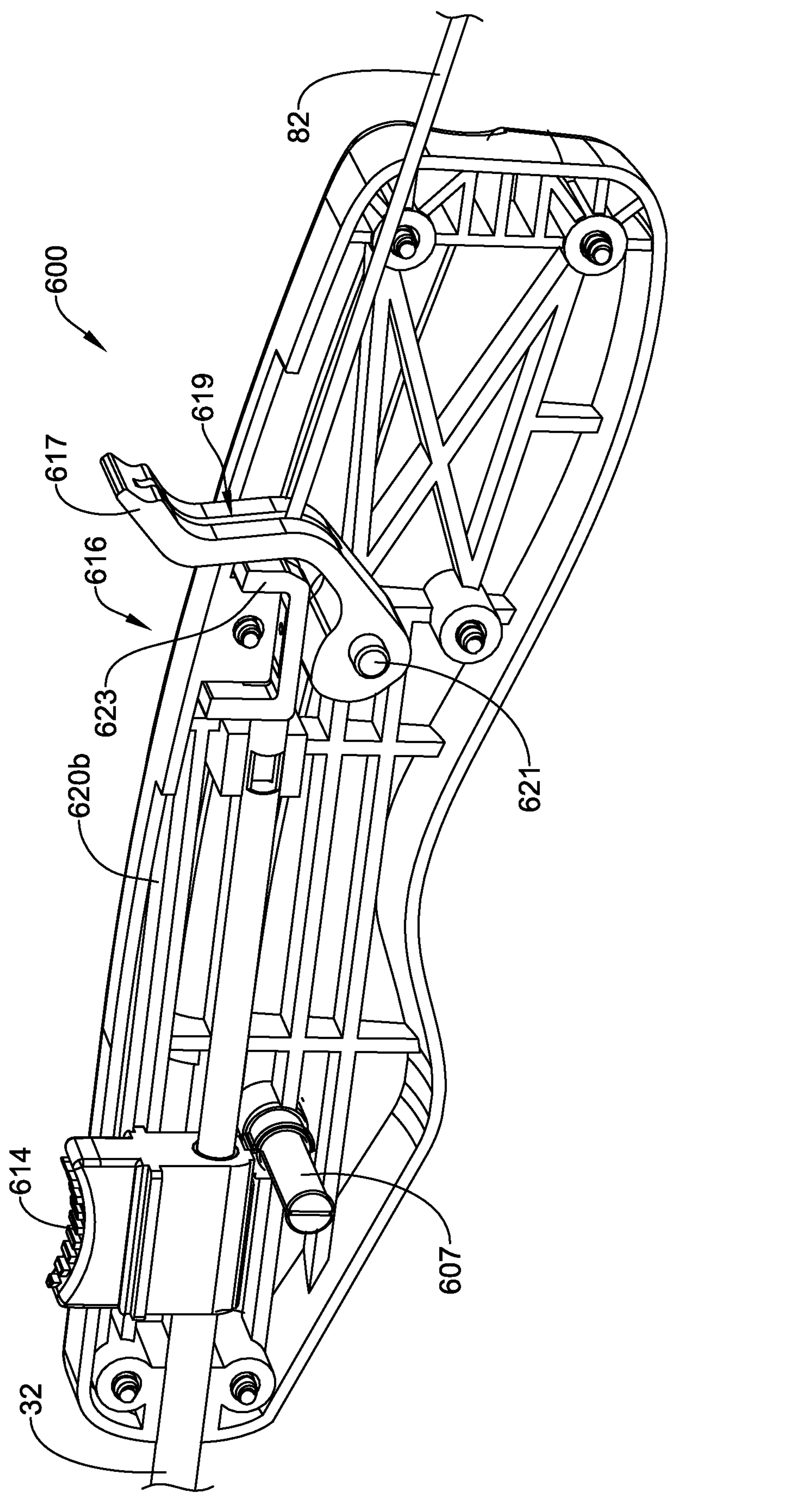
FIG. 28 is another detailed view of a portion of the implant delivery device shown in FIG. 26.

FIG. 27 illustrates a close up view of the tether clamp mechanism 616 described above. The tether clamp mechanism 616 may include a lever 617 which is designed to rotate around a pin 621 within a portion of the second handle portion 620*b*. Additionally, FIG. 27 illustrates that the lever 617 may include a slot 619 through which the tether member 82 may pass. Further, it can be appreciated that actuation of the lever 617 may shift the lever 617 between a first configuration (e.g., an unlocked or disengaged configuration) in which the lever 617 is spaced away from a clamping member 623 and a second configuration (e.g., a locked or engaged configuration) in which the lever 617 abuts the clamping member 623. It can be further appreciated that when the lever 617 is spaced away from the clamping member 623, the tether 82 may be free to translate (e.g., shift, slide, move, etc.) relative to the second housing member 620*b* (e.g., the tether can slide through the slot 619). However, FIG. 28 illustrates that when the lever 617 abuts the clamping member 623, the lever 617 may lift and pinch the tether 82 between the bottom portion of the slot 619 and the clamping member 623, thereby prohibiting the tether 82 from translating within the second housing member 620*b*. It can be appreciated that a clinician may actuate the lever 617 while manipulating the implant delivery device 600, thereby allowing the clinician to translate or, alternatively, clamp, the tether 82 relative to the housing 615 and the outer shaft 32.

Figure 29:
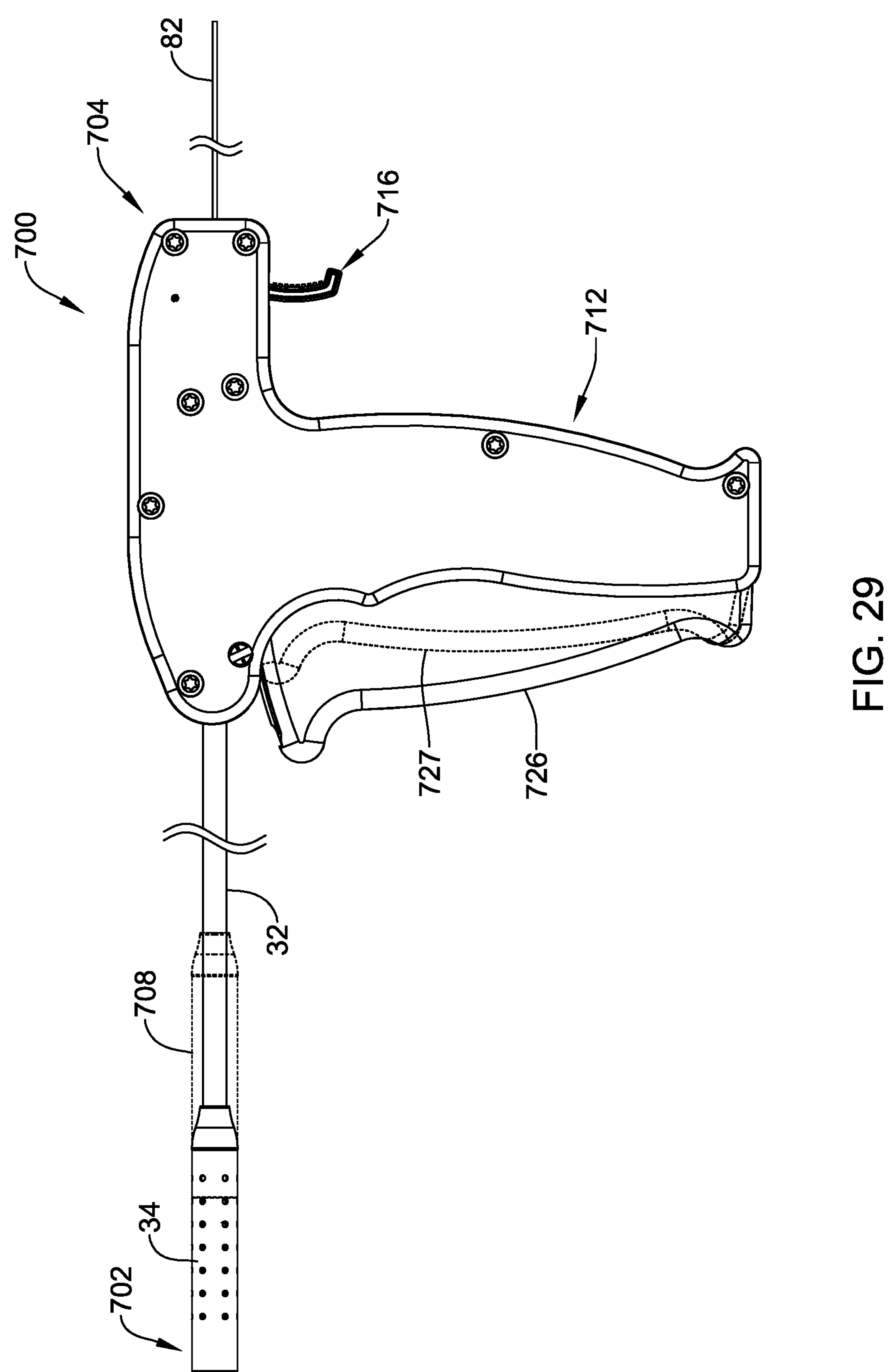
FIG. 29 is a side view of an example implant delivery device.

FIG. 29 illustrates another example implant delivery system 700. The example implant delivery system 700 may include a distal end region 702 and a proximal end region 704. The proximal end region 704 may include a handle 712. The distal end region 702 of the implant delivery system 700 may include an outer delivery sheath 34. FIG. 29 illustrates that the handle 712 may be attached to the delivery sheath 34 via an outer shaft 32.

It can be further appreciated that the delivery sheath 34 may surround the frame 46 and implant 12 when in a delivery configuration. For example, it can be appreciated that in a delivery configuration, the implant 12 may be attached to the frame 46, whereby the implant 12 and frame 46 (together) may be folded and positioned within the delivery sheath 34.

Additionally, it can be appreciated that retraction of the outer shaft 32 may release (e.g., deploy) the implant 12 and frame 46 from the delivery sheath 34. In other words, the implant 12 and frame 46 may be positioned within the delivery sheath 34 as the outer shaft 32 is inserted into a patient's body and advanced toward a target delivery site. After being positioned at the delivery site, the outer shaft 32 may be retracted while the inner shaft 36 (described above) may be held stationary relative to the outer shaft 32. As discussed above, retraction of the outer shaft 32 may retract the delivery sheath 34, which uncovers (e.g., releases) and deploys the implant 12 and the frame 46.

Further, it can be appreciated from FIG. 29 that the handle 712 of the delivery system 700 may include a trigger 726. Further, as will be discussed in greater detail below, the outer shaft 32 may be retracted via actuation of the trigger 726. For example, FIG. 29 illustrates the trigger 726 may be actuated (e.g., squeezed), thereby shifting it from a first position to a second position. The squeezing of the trigger 426 may retract the outer delivery sheath 442 in a distal-to-proximal direction relative to the inner shaft 36. The second position of the trigger 426 (e.g., after it has been squeezed) is shown by the dotted line 727. As discussed above, retraction of the outer shaft 32 (via squeezing of the trigger 726) may also retract the delivery sheath 34, thereby deploying the frame 46 and implant 12. FIG. 29 illustrates the final position of the delivery sheath 34 after being retracted in a distal-to-proximal direction by the dotted outline 708.

In some examples (such as those discussed above), the delivery system 700 may include a mechanism which may clamp and secure the tether member. FIG. 29 illustrates the tether 82 which may extend from the tack member (not shown in FIG. 29) through an aperture (not visible in FIG. 30) located along the side surface of the handle 712 to a position outside the handle 712. Namely, the tether 82 may be secured to the frame 46 via a connection member, or otherwise secured to the frame 46, as described above. FIG. 29 illustrates that delivery system 700 may include a tether clamp mechanism 716. The tether clamp mechanism 716 will be discussed in greater detail below.

Figure 30:
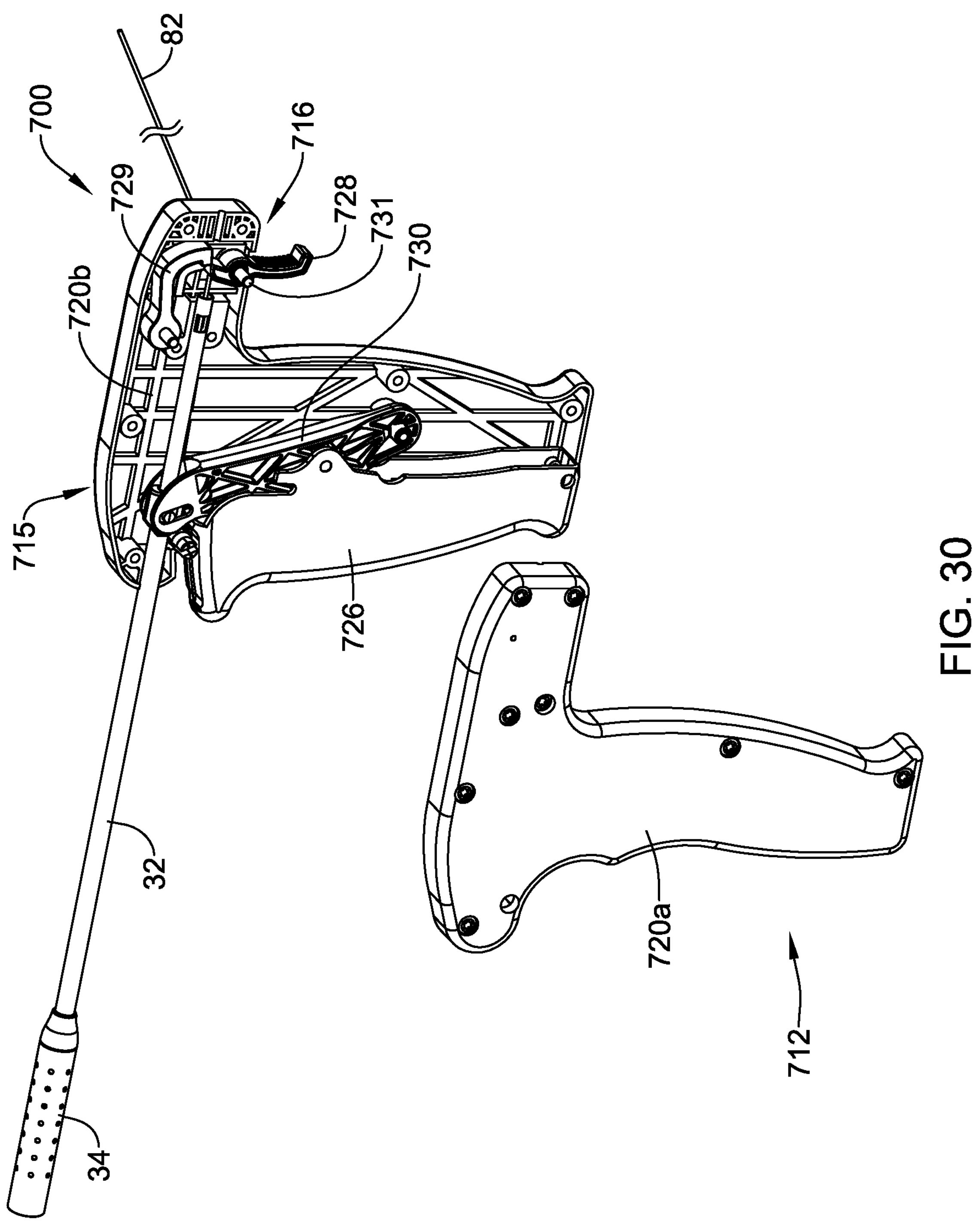
FIG. 30 is a perspective view of the implant delivery device shown in FIG. 29.

FIG. 30 illustrates the implant delivery system 700, as described above. In particular, FIG. 30 illustrates a partially exploded view of the handle 712 shown in FIG. 29. As illustrated in FIG. 30, the handle 712 may include a housing 715 having a first handle portion **720*a* and a second handle portion 720*b*. The first and second handle portions 720*a*/720*b* may be attached together in a clamshell configuration. In other words, the first handle portion 720*a* and the second handle portion 720*b* may be attached together via screws, a snap-fit, etc. to form the housing 715**.

FIG. 30 further illustrates that the delivery system 700 may include the trigger 726, the tether clamp mechanism 716 and a portion of the outer shaft 32 positioned within the housing 715, whereby a portion of the outer shaft 32 extends from the trigger 726 to the delivery sheath 34. It can be appreciated from FIG. 30 that the trigger 726 may be coupled to the outer shaft 32 via a linkage 730. As discussed above, FIG. 30 further illustrates the tether 82 may extend from the tack member 84 (discussed above), through the inner shaft 36 extending through the outer shaft 32, through the tether clamp mechanism 716 and thereafter exit an aperture located in the side surface of the second handle portion **720*b*. The tether clamp mechanism 716 may fixedly secure the tether 82 from relative longitudinal movement relative to the inner shaft 36** when in a locked position.

FIG. 30 further illustrates a detailed view of the tether clamp mechanism 716 described above. The tether clamp mechanism 716 may include a first lever 728 which is designed to rotate around a pin 731. The tether clamp mechanism 716 may also include a second lever 729 which is designed to rotate around a pin 732. Further, it can be appreciated that the first lever 728 is designed to be actuated from a first position to a second position.

Figure 31:
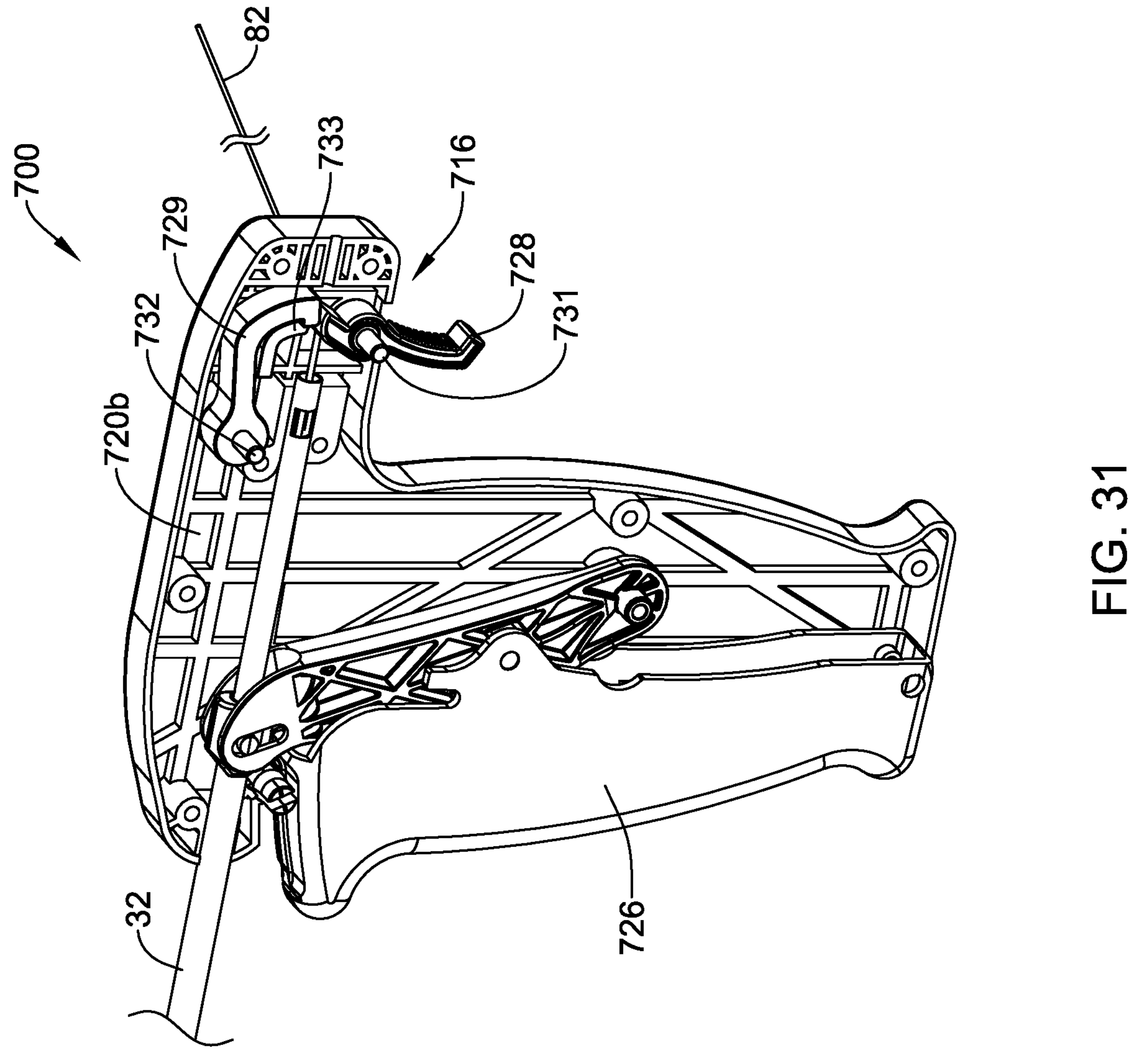
FIG. 31 is a detailed view of a portion of the implant delivery device shown in FIG. 29.

Additionally, the second handle portion **720*b* may include a rib member 733. In some examples, the tether 82 may be "pinched" between the rib member 733 and the second lever 729. When pinched, the tether 82 may be prevented from shifting relative to the outer shaft 32. However, when actuated from a first position (e.g., a locked or engaged configuration) to a second position (e.g., an unlocked or disengaged configuration), as shown in FIG. 31, the first lever 728 may force the second lever 729 to flex off the rib member 733, thereby permitting the tether 82 to be free to shift relative to the housing 715 and the outer shaft 32 It can be appreciated that a clinician may actuate the first lever 728 while manipulating the implant delivery device 700, thereby allowing the clinician to manipulate the tether 82 relative to the housing 715 and the outer shaft 32**.

Figure 32:
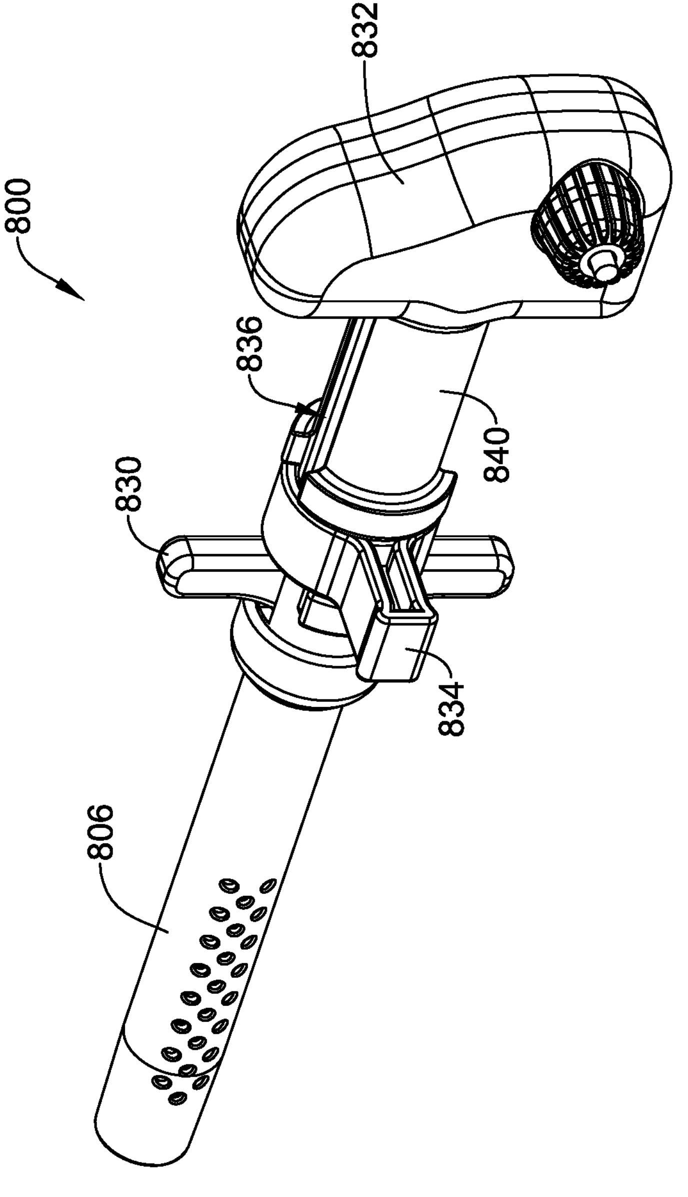
FIG. 32 is perspective view of another example implant delivery device.

FIG. 32 illustrates another implant delivery system 800. The implant delivery system 800 may include an outer delivery sheath 806 coupled to a handle 832 via an actuation shaft 840. The actuation shaft 840 may include a channel 836 extending along the longitudinal axis of the actuation shaft 840. Further, the delivery system 800 may further include an actuation member 830 which is attached to both the outer delivery sheath 806 and the actuation shaft 840. It can be appreciated that the actuation member 830 may be designed to translate within the channel 836. Further yet, FIG. 32 illustrates that the delivery system 800 may also include a removable safety lock 834 which is designed to prevent inadvertent actuation of the actuation member 830.

Figure 33:
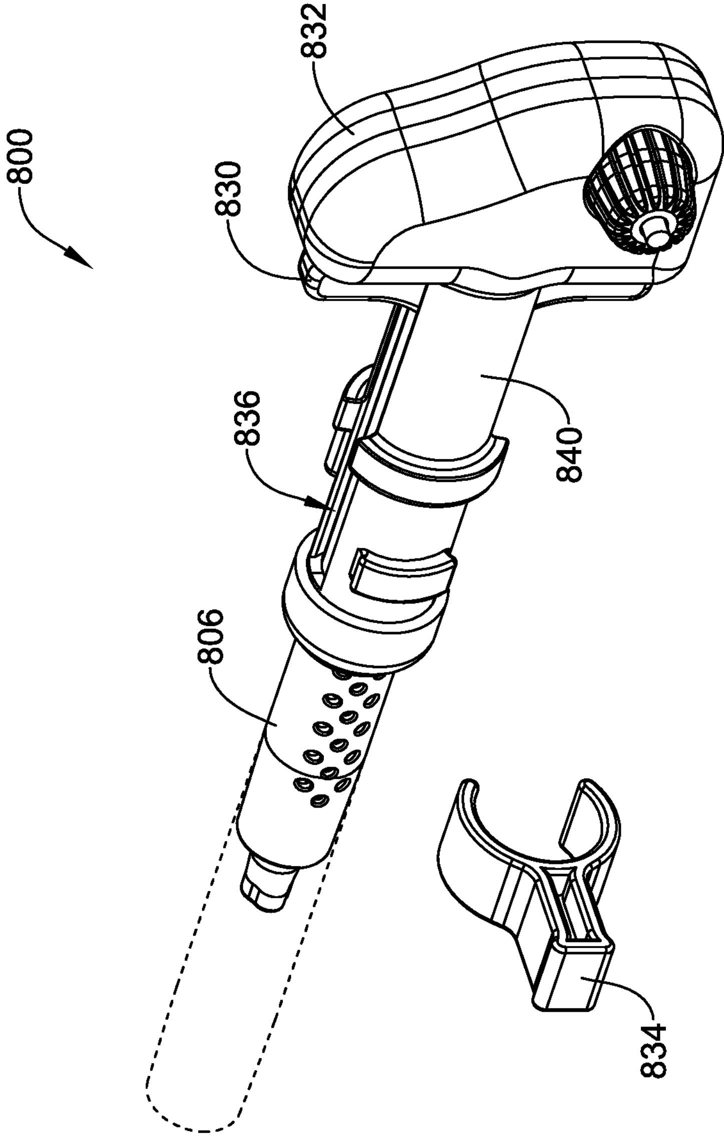
FIG. 33 is another perspective view of the implant delivery device shown in FIG. 32.

FIG. 33 illustrates the implant delivery system 800 after the actuation member 830 has been translated in a distal-to-proximal direction along the longitudinal axis of the actuation shaft 840. It is noted that in order for the actuation member 830 to be shifted along the actuation shaft 840, the safety lock 834 had to have been removed from the actuation shaft 840 (as shown in FIG. 33). It can be further appreciated from FIG. 33 that as the actuation member 830 is translated proximally (within the channel 836), the outer delivery sheath 806 may be retracted proximally. The proximal retraction of the outer delivery sheath 806 may uncover, and thereby deploy, the implant 12 and frame 46 (discussed above) from the lumen of the outer delivery sheath 806. It can further be appreciated that the delivery system 800 may be designed such that a clinician may be able to deploy the implant 12 and frame 46 with one hand.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An implant delivery system, the implant delivery system comprising:

a delivery shaft including a proximal portion and a distal portion; and a detachable frame coupled to the distal portion of the delivery shaft, wherein the detachable frame includes a body portion and a plurality of attachment arms extending away from the body portion;

wherein the body portion further includes a first support strut positioned adjacent to a second support strut, and wherein the first support strut converges with the second support strut at a first convergence region, and wherein a first attachment arm of the plurality of attachment arms extends away from the first convergence region;

a connection assembly coupled to the delivery shaft, the connection assembly including a tack member attached to a tack disk, wherein the tack disk is further attached to a collar, and wherein the collar is configured to extend into and engage the distal portion of the delivery shaft; and wherein the detachable frame includes a plurality of connector legs, wherein at least one of the plurality of connector legs is disposed between the tack disk and the collar.

2. The implant delivery system of claim 1, wherein the first support strut and the second support strut are arranged in a substantially triangular geometry.

3. The implant delivery system of claim 1, wherein the body portion further includes a third support strut positioned adjacent to a fourth support strut, and wherein the third support strut converges with the fourth support strut at a second convergence region, and wherein a second attachment arm of the plurality of attachment arms extends away from the second convergence region.

4. The implant delivery system of claim 3, wherein the second support strut converges with the fourth support strut.

5. The implant delivery system of claim 3, wherein the first attachment arm and the second attachment arm extend away from one another.

6. The implant delivery system of claim 1, wherein the plurality of attachment arms are configured to be attached to an implant.

7. The implant delivery system of claim 1, further comprising:

a handle attached to the proximal portion of the delivery shaft; and a tether secured to the frame and extending proximally through a lumen of the delivery shaft to the handle;

wherein the handle further includes a tether clamp configured to lock the tether to the handle.

* * * * *